United States Patent
Adams et al.

[11] Patent Number: 5,861,298
[45] Date of Patent: Jan. 19, 1999

[54] CATHEPSIN K GENE

[75] Inventors: Mark D. Adams, North Potomac; Judith A. Blake, Laurel, both of Md.; Christine M. Debouck, Wayne; Fred H. Drake, Glenmoore, both of Pa.; Lisa M. Fitzgerald, Germantown; Claire M. Fraser, North Potomac, both of Md.; Maxine Gowen, Valley Forge, Pa.; Gregg A. Hastings, Thousand Oaks, Calif.; Ewen F. Kirkness, Olney; Norman H. Lee, Woodstock, both of Md.; Julie Rood, Lansdowne, Pa.

[73] Assignees: SmithKline Beecham Corporation, Philadelphia, Pa.; Human Genome SciencesInc, Rockville, Md.

[21] Appl. No.: 852,807

[22] Filed: May 7, 1997

Related U.S. Application Data

[60] Provisional application Nos. 60/019,942 Jun. 14, 1996, 60/020,273 Jun. 17, 1996 and 60/026,083 Aug. 26, 1996.

[51] Int. Cl.$^6$ .......... C12N 15/11; C12N 15/57; C12N 15/63; C12P 21/02
[52] U.S. Cl. .......... 435/226; 435/320.1; 435/325; 536/23.2; 536/23.5; 536/24.31
[58] Field of Search .......... 536/23.2, 23.5, 536/24.31; 435/320.1, 325, 226

[56] References Cited

U.S. PATENT DOCUMENTS 5,501,969 3/1996 Hastings et al. .......... 435/325

OTHER PUBLICATIONS

Inaoka et al., Biochem. Biophys. Res. Comm. 206:89–96, Jan. 1995.
Bromme et al., Biol. Chem. Hoppe–Seyler 376:379–384, Jun. 1995.

*Primary Examiner*—Eric Grimes
*Attorney, Agent, or Firm*—William T. Han; William T. King

[57] ABSTRACT

The invention relates to cathepsin K polypeptides, polynucleotides encoding the polypeptides, methods for producing the polypeptides, in particular by expressing the polynucleotides, and agonists and antagonists of the polypeptides. The invention further relates to methods for utilizing such polynucleotides, polypeptides, agonists and antagonists for applications, which relate, in part, to research, diagnostic and clinical arts.

22 Claims, 31 Drawing Sheets

| No. | cDNA (bp) | Donor | Acceptor | Intron size (bp) | Amino Acid interrupted |
|---|---|---|---|---|---|
| 1 | 48 | GCAGgtaacgtttgcaact | ctacattcttctcagGATG | 1427 | Noncoding |
| 2 | 169 | CAAGgtgcctggggtcctg | ctatgctttgtttagGTGG | 462 | Lys40/Val41 |
| 3 | 292 | CATGgcaagtatagcttca | tcttctttgtcttagACCA | 85 | Met81/Thr82 |
| 4 | 448 | TCAGgtactctcctttctt | ctgtatccctttcagGGTC | 1624 | Gln133/Gly134 |
| 5 | 667 | ACAGgtgagtgagattgct | gtttcttccagccagGAAG | 4326 | Gln206/Gly207 |
| 6 | 833 | AAAGgtaagaagctgctga | tagtttgtattctagGTGT | 270 | Gly262 |
| 7 | 939 | ACAGgtaatgatgggaaca | tgattggtcttacagCTGG | 2270 | Ser297 |

Exon and intron sequences are designated by upper and lower case letters respectively.

[SEQ ID NO. 1]

```
GCTTTGGCTCCCAAAGGCCTGGGATTACAGGCGTGAACCACTGCGCCTAG
CCTGTTAGCAGCTCTTAAAATCCAGAGGCATAAGCCTGTATTTTTGAGGG
TTTATGCATGGAATCCAGCTAGAAACTGAGTCTATTACAGATCCCATTTA
TTATCCTTTCTATTCCAAGAAGCCTTTTTTTCTCCTTCCCCACATCTGTT
TATGGAAGAAAATGAAGTTTGGGGTGTGGTTTGAGGAATCAGCTAGATTC
TTATGATCTGTCACATGCTTGGATGTTGGGGAAGCATTTGGAGAAGCTCA
TGTGACTTGTCCTAGATTGGGGATTTTAATTGAGACAGATGATGTTTATC
GGGCATCCACCACCTGAGAGTTTTAGCAACAGAGTCACATGTGAGTCCA
TCAGAACTTACGGCATTGATTCAAGTGCTGTCATAAATAACCAGGACTGC
TGTTTTTGGTTACTTTTAAAGACAGTTTCATCTGGACTTTCTGGGCATAT
CCTCCTTCAGCAAAACCACATTAGGCTGGGAAAACTATTCTGCCTGGAAG
TAATGACAACTTGCAACCAACAAGCTTATAAAAATACAAAGAATTCTGGA
GCCTATGGCTTCCATTACATTATTCTTTTATAGCCTTTTATGTTCATTAC
CGCATCCCAGAGGTGAGAGTCAGACACAAATATGAAAATAGGTTTCAATG
TTGGAGAGGTAAATCCTAACAGGAAGGGGTAGGAAAGATATAATCCCC
CAATATTAAAATAAAGATATTGAAGAAGAAGGATGGGAGAGACTAGGGCT
GTGTCCTTCCTTTTACTCACCAAAAGAGAAAGTAAGCTCCTATTTGAGTC
AATAGATATTGAGGTCTTGTTATTTGCCACCAAAGACAGTCTTGTGAGAC
TAAATAGCTAGTAATTCCCTACCCTGGCACACATGCTGCATACACACAGA
AACACTGCAAATCCACTGCCTCCTTCCCTCCTCCCTACCCTTCCTTCTCT
CAGCATTTCTATCCCCGCCTCCTCCTCTTACCCAAATTTTCCAGCCGATC
ACTGGAGCTGACTTCCGCAATCCCGATGGAATAAATCTAGCACCCCTGAT
GGTGTGCCCACACTTTGCTGCCGAAACGAAGCCAGACAACAGATTTCCAT
CAGCAGgtaacgtttg caacttccta gatcttttag cttttcattcc
tgtcaattctctgagtattagggatgtagtgacttgaggatcacaataaa
cttttagcctctgcagatgaaacagagatgcacttcttaggtcattccc
tggctaaataaaatctgcctggaaatctgtagaattccttgtatgattta
tatatatacatacatgattgttagtaaaagcaaagtatatagggaatcat
ttccccatccttcaagagtggcctttctgcagtgttttctactttggcca
acaaggatcaaaacggttaactccttagtgaggaggaggagagtggtatg
gggaggtagtagctcagtgcttcctgttcactgagacatctcaaagccct
taacactctagttttaaatgtcctactggacattttgccagtttgcaaa
attacatgtaaatggactataagcaattgtgtaagccatatgtcatgctg
caggctgcaaattgttcttaaaatggaggatttgtaattaagaaagccaa
tgcaagaaatgagtgaagctaactagagtaaacttatgaaaagctgtgaa
tttcatcatcatagaacattgcttttcagtctgaacattcttctaacaaa
ccttggatctgaggcttcttgtcctttgcggcagccacagtgggttttttg
ttgttagggggaaaataaaaaaccttgcccgcagcatctggttaagattag
ggcagttcctgcctaaggagggaagggagagaaaaaggaagaagaaatg
cataaggagaatgaggagatacaatgtctcagaaaacaggaaacattg
tcctattttcccttgtcctcttctgacaagatctgggaaagtaccagaat
ttaggcacgaaagagaagaacgcctcgaagaaatgatcaggaagcaaaac
ttagacggaaatctctcctttgtgtattctgaacccactaccaccttgc
tatttgtctg tctccaagcc tgctagggac cctggaggaa acgcactgag
cccattctga ttgtccagtt tctatccccc atttctggtt gtgtacgtgt
gtgtgtgtgt gtgtgtgtgt gtgtgtgtgt gtgtgtgtgt gagagagaga
```

FIG. 1A gagacagaga gagaaacaga gagagtgtgt gttgcctaaa tctcccgaga
gagagagaga gagagagaga gagagagaga gagagaaaag agagaaatgg
ctaaatcccc ctagatcaaa gtccttggaa ccagatgtac cagcatccta
tctaaacaca ggcccctcct gactatcatt gttttatcac ccttttccg
tctacctttc tcttcctcat aaagcctagt tttcctctgt ttccctgcca
aatggaagag ttttccctaa ctacattctt ctgcag<u>GATG TGGGGCTCA
AGGTTCTGCT GCTACCTGTG GTGAGCTTTG CTCTGTACCC TGAGGAGATA
CTGGACACCC ACTGGGAGCT ATGGAAGAAG ACCCACAGGA AGCAATATAA
CAACAAG</u>gtg cctggggtcc tggagggggc atggcaggaa ggctgag
acctgagctc tctcatctta gcttccagac tcccttcttc aatccaaatg
ctttattcca agcaaatcag tccctcttcc ctaactcatg ttaacatacg
gttttcattc ctatgcttca atcatcctct tgtcaaactt gtattccttc
cctttggttt tataagtgtg taacattcct cttttgggaa gagtcccaag
attaatgctg ttaatccata agcaattttt ctgtctctcc agagcttgtg
tggttgttta catattatct ctcttcttgc aggctcttaa ttccatggtt
agttccccaa ctaaactgta aacttttatg attgtgagtt tcctttattc
tcctaaaacc cttcacaata ttacatatga actgtagaca gtctatacaa
gtactgactatgctttgtttag<u>GTGGATGAAATCTCTCGGCGTTTAATTTGGA
AAAAAACCTGAAGTATATTTCCATCCATAACCTTGAGGCTTCTCTTGGTGTCCA
TACATATGAACTGGCTATGAACCACCTGGGGGACATG</u>gcaagtatagcttcagc
tcctgtcccacctgcaccatttgctttagttccctgctgatgcctggcctcttt
cttctttgtcttag<u>ACCAGTGAAGAGGTGGTTCAGAAGATGACTGGACTCAAAGTA
CCCCTGTCTCATTCCCGCAGTAATGACACCCTTTATATCCCAGAATGGGAAGGTAG
AGCCCCAGACTCTGTCGACTATCGAAAGAAAGGATATGTTACTCCTGTCAAAAATC
AG</u>gt actctccttt cttctgggtg tgcatatgta atctggca
tgaccttttc cttttctgc tgctttgttc ttgaggtgaa agggcaccag
gaaagaggg caaggaatta aggtacatct ccccattccc attctgttat
ttaacctcat ttgtttctgt acatttgggt tgtttctggt ttttcttttt
cttttccctt tttttttttt ttttttttt gagatagagt ctcactctgt
cgcccaggat ggagtgcagt ggtgcaatct tggctcactg caacctacac
ctcccgggtt caagcgattc tcctgcctca gcctcctgag tagctgagat

FIG. 1B

```
tacaggcacg  cgccactacg  cctggctaat  ttttctattt  ttatagagat
gcgttttcac  catgttggcc  aggctggtct  tgaactgacc  tcaggtgatc
cacctgcctc  agcctcccaa  agtgctggga  ttagagtcat  gagccatcgc
ggcctggttt  ttctttatta  caaatagtgt  tgcaataagc  acccttgtgc
atatgttttt  gtgcacatgt  acaaatattt  atgcaaaata  agtcctaaaa
ttggaattgt  taggtcacaa  ataatccttt  ccccccccccc aaatttttt
ttttttttg   agacagcgtc  tctgtcaccc  aggctggagt  ccagtggcgc
aatcatggct  cactgcagcc  tcaacgtctc  aggctcaagt  gattctccaa
cctcagcctc  cctagtagct  gggaattaga  agcacatgcc  accacaccca
gctaatttta  aaaattttt   tgttagagac  agggttttgc  catgctaccc
aagctggtct  caaattcctg  ggctcaagca  atctgcccgc  ttcggcctcc
caaagtgcta  ggattacaga  catgagccac  catgcccagc  ccaaaaagt
ttttgcaatc  ttacattctt  actagcatga  gaatgtcagt  tttttcacaa
cccaaacaac  acaggattgt  atcagcaaga  taaacaattg  atttaacgtt
catttaacaa  acactttttg  accccagaa   cctaccagat  gcagtgttag
gcagcagaga  ctcaagatga  ctaagacaca  acctgtgtcc  tcaggaaatc
tcaatctaaa  aaaatagaac  aggaaagaaa  gaaaaatcta  caatctagct
gcacaaacaa  taatagctaa  tactttttga  gattttattg  tttgtcagga
acttcttaac  tctttacatg  agtttaaata  tttaatccct  tataacaata
ttttatgcat  agagaaactg  agacacaggc  aaatttagta  acttacccgg
ggtcacatag  ctactgggtg  gcaaagtcag  ggttagctcc  caggacaaat
gcctccacag  ctggtactgt  gctctgcttt  actgtagcta  atagtaaaaa
tggtagcaaa  aatcaatagc  agtagaacag  tgcaacagat  attaagcgga
agaggaagac  tcacaacaat  gacaacattt  gtgctgaaat  ttttaagaac
acatggaatt  tccttcagcc  gggtagagag  aagatataga  aatgtaaaca
ccaaagattc  atagtttctc  tgtatccctt  tcagGGTCAGTGTGGTTCCTG
TTGGGCTTTTAGCTCTGTGGGTGCCCTGGAGGGCCAACTCAAGAAGAAAACTGG
CAAACTCTTAAATCTGAGTCCCCAGAACCTAGTGGATTGTGTGTCTGAGAATGA
```

FIG. 1C

TGGCTGTGGAGGGGGCTACATGACCAATGCCTTCCAATATGTGCAGAAGAACCGGG
GTATTGACTCTGAAGATGCCTACCCATATGTGGGACAGgtg        agattgctcc
acacaattat   acagctctgt   tggctcctcc   ttccccagca   tgatgtt
ttgtactgga   aacaattcca   gaaatactgt   tttctgttat   cctatcctgc
tttcttgatg   gaataatttc   ccacagaagg   ccaagaagat   ttccacaatc
tggggaatt    tagggagctt   aagctactat   agctcctatt   tgcatctctg
ccatggagag   aaaacagagg   ctaggctacc   tacccatag    acttccgagc
tgggttctat   aaccctctgc   tcaattcctc   actcccacaa   caaacccaca
aacccaccat   gctattttca   caaattgtgt   ggctttattt   tatatgatct
cagtgtgagt   tttcagaaca   tttcagcaaa   ttatgtaagt   ttacatgcta
acatctataa   aatgagagaa   aaaacaagtt   gcttcatata   agagataagg
gattaactca   gttcctcctg   catgatcctc   tagtcatagg   aaggaaatca
tatctgaaag   ggaggcaacc   tgagggggtt  tttatacaca   tagggctggg
tctgatagac   aatataatgt   agggccttca   caacagaaac   ctctgaaaca
gggacagcaa   gtttgagaat   aaaaatgatg   gctactgtgt   tctaagccgt
gtccttagtg   cattttttct   ttttcttttt   ttcatttaat   ctcataacaa
ctctgttagg   tagacttatc   ttgaatgtat   aggtgaggaa   atggacactt
aaggagataa   gacagtataa   ttcataccac   tagtatgtaa   caatgtaaga
tgtatctacc   agggatgttt   atcttctgca   aacattccta   ggtatatctc
ccatgcacat   gtgcaagaat   ttcttactag   gatataatgc   cttggaactg
aattgtctgg   gtcttagggt   atgtctgtct   tcaactttac   tacacaatgt
caaattgttt   gccaaaatat   ttggaaaaat   ttatacctgc   aatgtgtaag
aaatccctt    caatcacctt   tttatcagta   tgtttatctg   gccatttgca
tttcttcttc   agtgaattaa   ctgttttat   ctcttgctca   tttgttttc
tttttatttt   tttgaaatag   ggtcttactc   tgttgcccaa   ggctggagtg
tggtgataca   gtcatagctc   actgcagcct   ccacttccgg   gctcaagcaa
tcctctcgcc   tcagcctccc   aaatagctag   gatataggtg   catgccatca
tgcccaccaa   tttcaaaaaa   cctttgaaat   ttttttttg    taaaagctag
gcatggtggc   tcatgcctgt   aatcccagca   ctttgggagg   ctgaggtggg

FIG. 1D

```
aggatcgctt gagcccagga attggaggtc ggcctgatac aacatagcaa
gacctcatct ctacagaaaa aattttaaa  agtagccagg tatgatggcg
tgcatagttc tagctactcc ggaagctggt tgggaggaca acttgagcct
gggagttcaa ggctgctgtg aactgtgatc atgtcactgc tctctagcct
gggtgacaga gtgagaccct gtccccaaaa acaacaaccg ttttttttgg
tagagacatt gtctcgctat gttgccaagg ctagtctcaa actcctgggc
tcaagcaatc ctcccacctc ccaaagtgct gggattatag atgtaagcca
ccatgcctgg cctacccttt ttttttttt  ttgaaatgga agttttgctt
ttgtcaccta ggcttgagtg cagtggcgcg atcttggctc actgcaacct
ccacctcctg gattcaagca attctcctgc ctcagcctcc tgaatagctg
ggattatagg cacccgcaac cacgcccggc tagttttgt  atttttagta
cagacagggt ttcaccatgt tggccagctg gtcttgaacc cctgacctca
ggtggtccgc ccgcctcggc ctcccaaaat gctgggatta aaagtgtgag
ccaccatgcc ccacccctta ctcattttta attggattgt ttttctctt
tcttagcgat tcttaaaagt ttaaagagaa tatttggata caatactatg
tatttaaaag ttgaggtctg tctttccatt cttctcacga tgtctttcaa
tctagaaaag ttaattttaa taggcctggc gcggtggctc acgcttgtaa
tcccagcact tgggaggct  gagatgggtg gatcacaagg tcaggagatg
aagaccatcc tggctaacat gggtgaaacc ctgtttctac taaaaataca
aaaaattag  ctgggcgtgg tggcaggtgc ctgtagttcc agctactcgg
gaggctgagg caggagaatg gcgtgaaccc gggaggtgga gcttgcagtg
agccgagatt gcaccactgc actccagcct gggcaactga gcaagactgc
gtttcaaaaa aaaaaaagt  taatttaat  atagtaaat  tagtaaaagg
attaattttc cctttgcaat ttttgtaatg tgttttattc gtttatgaat
ggagaaaggt aagaaaaat  aaaatttaaa aaagaagaga tgtggccagg
tacggtggct cacacctata atcccagtag tttgggaggc tgaggcaggc
agatcacttg aggtcaggag tttgagacca gctgggataa catggtgaaa
ccccatctct actaaaaata caaaaattag ccaggtgtga ttgcgcacgc
ttgtaatccc agcaggctga ggcaggagaa ttgctcgaac tcaggaggca
```

FIG. 1E

```
gaggttgcag  tgagccaaga  tcatgccatt  gcactccagc  ctgggtaaca
gagactctgt  ttcaaaaaaa  taaaaagata  aaaaaggaag  agatctgata
gggcggccag  ataaacattt  taaaggggat  ggtattataa  gtttgttccc
agcataatgc  caggttattc  tgactttaaa  gtatcatcac  ataatatctt
tttgagtcaa  tttccaagat  attctgtttc  acttgtaatt  ctgtgtaatt
tttggcacca  ggaggcatca  gggatttgga  gcacatggca  gaaacaaagg
catcttgaaa  aatatcaagg  cagtagacca  ctgtaatctt  aaaatggcat
atcaaatgct  gctattgctg  ttaatattta  gataatgtta  gataatgtat
tttttagag   ggtatctcac  tatcttgcac  aggctggagt  agagtggcta
ttcacagcat  gatcacagta  cactaaaggc  tcaaactcct  gggcacaaac
aatcctcctg  cctcagcctg  ctgagtagta  gataataagt  tcttgtggat
gcaaccttag  ggttctgaag  gggtagtctg  taggaaaatg  aattgctgaa
aagaatacac  caccttaaca  tgggctatta  ttcgattcca  taattgtggc
ttgccaatga  aacattgcta  actacctgta  aaatatagtg  ttggaagtca
taggctaaat  tgctaagttc  tttaatctat  tttagtgtct  tgttatgtac
tttatattt  tgtctttgat  gagagcacaa  ggatcacacc  agttccctg
ataggtgc   agagggccca  ggtcttccct  ctagctaagc  cttggccttg
gcctcctacc  cacacagcag  ctggtgcctt  cctgccccct  gaggctaata
catactatgt  ggccagaaga  tggtttatgc  tttttaaaaa  aatcttattt
cagaaatctt  tccctactgt  tttcctccca  catttatgtc  ttaaaacacc
tgtaggggat  ttttttttt   ttttttttt   tgagatggag  tctcgctctc
gcccaggctg  gagtgcaatg  gcgcgatctt  ggctcactgc  aaggtctgcc
tcccaggttc  acgccattct  cctgcctcag  cctccccagt  agctgggact
acaggcgccc  gctaccacgc  ctggctaatt  ttttgcatt   tttagtagag
acagggtttc  actgttagcc  aggatggtct  cgatctcctg  acctcgtgat
ccaccctcct  cagcctccaa  agtgctggga  ttaacaggca  tggagcccca
ccgcactggc  ctgtatttgt  gaggaagaac  agaccctctt  tagaagccct
agactgctgc  ctctgttagt  tcactggcat  cactcaaaat  attggttgag
tttcttactc  actgagttgg  ttttatgtg   tggtggaagg  cgggaatcct
```

FIG. 1F cttttcatat tcgttctcat tgcctattgc tttgtcctag tcctattaca
atcttgtttcttccagGAAGAGAGTTGTATGTACAACCCAACAGGCAAGGCAGCTA
AATGCAGAGGGTACAGAGAGATCCCCGAGGGGAATGAGAAAGCCCTGAAGAGGGCA
GTGGCCCGAGTGGGACCTGTCTCTGTGGCCATTGATGCAAGCCTGACCTC
CTTCCAGTTTTACAGCAAAG gtaagaagct gctgatccta tacagcactg
tcttttatga tacaaacttg atggtttctc gaaggacctt gggtattttc
agtacttagt ttttgtattc acatggaggt ggccagagag aaattaacaa
ctgctgcagt atggagcagc atctctgtgg taaaccctcc tgacacggat
ggaattcttc aaacagtctc ctagactggg agatcccaca gggtgaccct
tggattgcat agagcctcac gctggtagtt tgtattctag GTGTGTATTA
TGATGAAAGCTGCAATAGCGATAATCTGAACCATGCGGTTTTGGCAGTGGGAT
ATGGAATCCA GAAGGGAAACAAGCACTGGATAATTAAAAACAGgtaatgatg
ggaacactac ttttgttatt cagtcaccct tttaacactc aacctcacct
ccagcttccc gatattcctt tctctgtccc aaatcaagaa aaaattatct
cagagttctc acttctatct tctcagtcag aggctcttaa ttctcagtct
gacacttaat ggccagtgtg ttagtccatt ttgcattgcc acaaaagaat
acccgagact gggtagttta taaagaaacg aggtttgttt ggctatacaa
agcgtggcac tagtatctgc tcagcctctg atgaggcctc agagctttta
ctcatggcag aaggcaaaag agggagcagg catgtcacat agtgagagag
ggagcaagag agagagggag gtgccgactc tttaaagaac cagctcttgc
atgaactaat agagtgagaa ctcactcatc accaaggcga tggcaccaag
ccattccatg aggaatccac tctcataacc caaacacctc ccactatgcc
ccacctccca cattggggat cacatttcag catgagactg ggaggggaca
cacatccaaa ccatatccgc cagacaatag tgctcaatta tgtgctgggc
agatgctccc tgtgtgcaag gtgcttagtg acatacataa accaacgagc
agatgacacc ttcagtgagc tcagagccca ataagacaga cctaactaac
catgagataa agcagtacaa agaaccagca ggagctttgg aattacgtat
ttttactttc ttttgtctct aatgtgatca gtttcttaga tggtttccat
tagcaatctg tctttaacag taggggagca gcgttaaagg tttaatattc

FIG. 1G

```
cttttgaaca gttttttttcc ttcaaaatac acttaagata cacgtatata
agaacttgcc aaagattgtg aagagaaaca tttttagaa ataagatata
aacaaaaaaa gttagtgtta ctttcctatg ttggggaaca aagaaaactc
cagggtacct tgcttcccat ttctctttag caccttgtga cttttgggga
ggggcagatt gataacaatt atagttttcc tttcctggct gatcaccatt
aacctggcag cagcactggc taaatctcct gtccttagtg ccctccaagg
agcaggagcc ctagactctg ggtcgctgac agactcacgc agtggtgttg
ttcaaacctg aagcaacttt ttatatcaca gttccaactc aaggtgaacc
tgagcatctt cccaagtctc ccacagcttc tgtcctgtgt tgtcccttct
cttgactccc aggtccaagc acttaccctg ttctttcatg atcaggtacc
atgtgtggag atagcttcca agagagctgg gaggaagaaa ggacacaccc
gggcaggatc aggaacactg ggggcccctg gagaagggga gagtggggga
gggtacaggt tttaaataaa atgtgttggt aattagagaa ttgctggttg
gggaaagagg tctgaaaaca attcaggaag ataaacaaga caatctctcc
tctctcctct ttctcacgtc gtctctcttg tcttctagtc tcgctactca
tttccttagt aatctcatcc actctcatag tttcatccat ctctcctatg
gggtttaccc ccaaatcaag atcaccagct tcagcctcct tcttatgctc
taaactcaca ttttcaagat taatattccc caaatacagc tctgatcata
tcactctccc actcaaaatc cctcactggc tcctcacgat gatgggtcac
agagtaaagg tgaagctttt taaccttgca gtaaaggtaa ttcaacctga
tctcaatctg cctttccaga catctctccc actacaccct gttaggcaca
ctgcttttca gctacatgat cctaacagtg ccccacactt tcctgcctct
gttgttcatt tcacacccttt ccactggcat cccccttccca caggtcgaaa
ttctacttag ccttttggct cagctcaaat gccacctctt acatcaagcc
tctaagattc     tcttgatc''''''ag  aaggaatctt  tccctccttt
gatacctaca gtattatgcc ttctccctat ttcttgactt taaactcttt
aaagttaaaa aacatcatat tcattttgt gtaccatcag tacctcgcac
aatactcagt
aaatatttta atgaataaat aaactgagag tactaagtat tttcttgat
tggtcttacagCTGGGGAGAAAACTGGGGAAACAAAGGATATATCCTCATGGCT
```

FIG. 1H

CGAAATAAGAACAACGCCTGTGGCATTGCCAACCTGGCCAGCTTCCCCAAGATGTG
ACTCCAGCCAGCCCAAATCCATCCTGCTCTTCCATTTCCTTCCACGATGGTGCAGT
GTAACGATGCACTTTGGAAGGGAGTTGGTGTGCTATTTTTGAAGCAGATG
TGGTGATACTGAGATTGTCTGTTCAGTTTCCCCATTTGTTTGTGCTTCAAATGA
TCCTTCCTACTTTGCTTCTCTCCACCCATGACCTTTTTCCACTGTGGCCATCAGGA
CTTTCCCCTGACAGCTGTGTACTCTTAGGCTAAGAGATGTGACTACAGCCTGCCCC
TGACTGTGTTGTCCCAGGGCTGATGCTGTACAGGTACAGGCTGGAGATTTTCACAT
AGGTTAGATTCTCATTCACGGGACTAGTTAGCTTTAAGCACCCTAGAGGACTAGGG
TAATCTGACTTCTCACTTCCTAAGTTCCCTTCTATATCCTCAAGGTAGAAATGTCT
ATGTTTTCTACTCCAATTCATAAATCTATTCATAAGTCTTTGGTACAAGTTTACAT
GATAAAAAGAAATGTGATTTGTCTTCCCTTCTTTGCACTTTTGAAATAAAGTATTT
ATCTCCTGTCTACAGTTTAATAAATAGCATCTAGTACACATTCATTTTGTGTTGGA
TACTGTGTTAGGTGCTGGAGGAAAAAGATGAATAGAACATCTTCTATGTACTTGA
TGCGCTCACAGTCTGGTTGTAGAGACTGTCACATAAACATTTCATCCCAATTCATT
TATTTGTTCATTCCTTCAGCCAATATATATTGAGTTCTTACTCTGTGCCAAGAACT
GTACTACATTTCTGGGATTAAGTGGATATAAG
GAGATCTCAGTGTTTAATCTGCCTGAGGGGAGACTAAATTAAGTGACATGGAAACT
TGGGTCTTGAAAACATTTTAAGGTTATTTTTTCTTTTCTCTCTCTCGCT
        CTGTCTTTCTC
TCTCTTTCGTCAGGGTCTCCCTCTGTTGCCCAGGCTGGAGTC
AGTGGCACTCATAGCTCACTGCAGCCTTGATCTCCTGGGCTCAAGAGTTCTTCCCA
CCTCAGTCTCCTAAGTAGCTTGGACTACGG

FIG. 1I

```
intron 1
cDNA
CACACTTTGCTGCCGAAACGAAGCCAGACAACAGATTTCCATCAGCAG↑G
49
                              ─────────────────────→1F
ATGTGGGGGCTCAAGGTTCTGCTGCTACCTGTGGTGAGCTTTGCTCTGTACCCTGAG
GAG     109
 M  W  G  L  K  V  L  L  L  P  V  V  S  F  A  L  Y  P  E
 E
                                      ─────────────────→2F
 1R←────── intron 2
ATA↑CTGGACACCCACTGGGAGCTATGGAAGAAGACCCACAGGAAGCAATATAACAAC
AAG↑       169
 I  L  D  T  H  W  E  L  W  K  K  T  H  R  K  Q  Y  N  N
 K
─────────────────────
GTGGATGAAATCTCTCGGCGTTTAATTTGGGAAAAAAACCTGAAGTATATTTCCATC
CAT     229
 V  D  E  I  S  R  R  L  I  W  E  K  N  L  K  Y  I  S  I
 H
              2R←──────────────────→3F
AACCTTGAGGCTTCTCTTGGTGTCCATACATATGAACTGGCTATGAACCACCTGGGG
GAC     289
 N  L  E  A  S  L  G  V  H  T  Y  E  L  A  M  N  H  L  G
 D
intron 3
ATG↑ACCAGTGAAGAGGTGGTTCAGAAGATGACTGGACTCAAAGTACCCCTGTCTCA
TTCC    349
 M  T  S  E  E  V  V  Q  K  M  T  G  L  K  V  P  L  S  H
 S
                   3R←──────────────────
CGCAGTAATGACAC↑CTTTATATCCCAGAATGGGAAGGTAGAGCCCCAGACTCTGTC
GAC     409
 R  S  N  D  T  L  Y  I  P  E  W  E  G  R  A  P  D  S  V
 D
                                        intron 4
─────────────────────
TATCGAAAGAAGGATATGTTACTCCTGTCAAAAATCAG↑GGTCAGTGTGGTTCCTG
TTGG    469
 Y  R  K  K  G  Y  V  T  P  V  K  N  Q  G  Q  C  G  S  C
 W
─────→4F
GCTTTTAGCTCTGTGGGTGCCCTGGAGGGCCAACTCAAGAAGAAAACTGGCAAACTC
TTA     529
 A  F  S  S  V  G  A  L  E  G  Q  L  K  K  K  T  G  K  L
 L
```

FIG. 2A

```
AATCTGAGTCCCCAGAACCTAGTGGATTGTGTGTCTGAGAATGATGGCTGTGGAGGG
GGC    589
N   L   S   P   Q   N   L   V   D   C   V   S   E   N   D   G   C   G   G
G

TACATGACCAATGCCTTCCAATATGTGCAGAAGAACCGGGGTATTGACTCTGAAGAT
GCC    649
Y   M   T   N   A   F   Q   Y   V   Q   K   N   R   G   I   D   S   E   D
A
                    intron 5
4R←̄̄̄̄̄̄̄̄̄̄
TACCCATATGTGGGACAG↑GAAGAGAGTTGTATGTACAACCCAACAGGCAAGGCAGC
TAAA   709
Y   P   Y   V   G   Q   E   E   S   C   M   Y   N   P   T   G   K   A   A
K
          ————————→5&6F
TGCAGAGGGTACAGAGAGATCCCCGAGGGGAATGAGAAAGCCCTGAAGAGGGCAGTG
GCC    769
C   R   G   Y   R   E   I   P   E   G   N   E   K   A   L   K   R   A   V
A CGAGTGGGACCTGTCTCTGTGGCCATTGATGCAAGCCTGACCTCCTTCCAGTTTTAC
AGC    829
R   V   G   P   V   S   V   A   I   D   A   S   L   T   S   F   Q   F   Y
S
  intron 6
AAAG↑GTGTGTATTATGATGAAAGCTGCAATAGCGATAATCTGAACCATGCGGTTTT
GGCA   889
K   G   V   Y   Y   D   E   S   C   N   S   D   N   L   N   H   A   V   L
A
     7F—————————————————→←——————————————5&6R
intron 7
```

FIG. 2B

```
GTGGGATATGGAATCCAGAAGGGAAACAAGCACTGGATAATTAAAAACAG↑CTGGGG
AGAA  949
 V  G  Y  G  I  Q  K  G  N  K  H  W  I  I  K  N  S  W  G
 E

AACTGGGGAAACAAAGGATATATCCTCATGGCTCGAAATAAGAACAACGCCTGTGGC
ATT  1009
 N  W  G  N  K  G  Y  I  L  M  A  R  N  K  N  N  A  C  G
 I

7R←─────────────────────→8F
GCCAACCTGGCCAGCTTCCCCAAGATGTGACTCCAGCCAGCCCAAATCCATCCTGCT
CTT  1069
 A  N  L  A  S  F  P  K  M
CCATTTCCTTCCACGATGGTGCAGTGTAACGATGCACTTTGGAAGGGAGTTGGTGTG
CTA  1129

TTTTTGAAGCAGATGTGGTGATACTGAGATTGTCTGTTCAGTTTCCCCATTTGTTTG
TGC  1189

TTCAAATGATCCTTCCTACTTTGCTTCTCTCCACCCATGACCTTTTTCCACTGTGGC
CAT  1249

8R←─────────
CAGGACTTTCCCCTGACAGCTGTGTACTCTTAGGCTAAGAGATGTGACTACAGCCTG
CCC  1309
─────────→9F
CTGACTGTGTTGTCCCAGGGCTGATGCTGTACAGGTACAGGCTGGAGATTTTCACAT
AGG  1369

TTAGATTCTCATTCACGGGACTAGTTAGCTTTAAGCACCCTAGAGGACTAGGGTAAT
CTG  1429

ACTTCTCACTTCCTAAGTTCCCTTCTATATCCTCAAGGTAGAAATGTCTATGTTTTC
TAC  1489

TCCAATTCATAAATCTATTCATAAGTCTTTGGTACAAGTTTACATGATAAAAAGAAA
TGT  1549

GATTTGTCTTCCCTTCTTTGCACTTTTGAAATAAAGTATTTATCTCCTGTCTACAGT
TTA  1609

ATAAATAGCATCTAGTACACATTCA

1634

---

3'UTR

TTTTGTGTTGGATACTGTGTTAGGTGCTGGAGGAAAAAAGATGAATAGAACATC

1688

TTCTATGTACTTGATGCGCTCACAGTCTGGTTGTAGAGACTGTCACATAAACATTTC

ATC 1748

CCAATTCATTTATTTGTTCATTCCTTCAGCCAATATATATTGAGTTCTTACTCTGTG

CCA 1808

AGAACTGTACTACATTTCTGGGATTAAGTGGATATAAGGAGATCTCAGTGTTTAATC

TGC 1868

CTGAGGGGAGACTAAATTAAGTGACATGGAAACTTGGGTCTTGAAAAACATTTTAAG

GTT 1928

ATTTTTTCTTTTCTCTCTCTCTCGCTCTGTCTTTCTCTCTCTTTCGTCAGGGTCTCC

CTC 1988

TGTTGCCCAGGCTGGAGTCAGTGGCACTCATAGCTCACTGCAGCCTTGATCTCCTGG

GCT 2048

CAAGAGTTCTTCCCACCTCAGTCTCCTAAGTAGCTTGGACTACGG

Cathepsin-K Sequence: Exon-Intron Boundaries

(A) 5' Untranslated sequence [SEQ ID NO. 2]

```
GCTTTGGCTC CCAAAGGCCT GGGATTACAG GCGTGAACCA CTGCGCCTAG
CCTGTTAGCA GCTCTTAAAA TCCAGAGGCA TAAGCCTGTA TTTTTGAGGG
TTTATGCATG GAATCCAGCT AGAAACTGAG TCTATTACAG ATCCCATTTA
TTATCCTTTC TATTCCAAGA AGCCTTTTTT TCTCCTTCCC CACATCTGTT
TATGGAAGAA AATGAAGTTT GGGGTGTGGT TTGAGGAATC AGCTAGATTC
TTATGATCTG TCACATGCTT GGATGTTGGG AAGCATTTG GAGAAGCTCA
TGTGACTTGT CCTAGATTGG GGATTTTAAT TGAGACAGAT GATGTTTATC
GGGCATCCCA CCACCTGAGA GTTTTAGCAA CAGAGTCACA TGTGAGTCCA
TCAGAACTTA CGGCATTGAT TCAAGTGCTG TCATAAATAA CCAGGACTGC
TGTTTTTGGT TACTTTTAAA GACAGTTTCA TCTGGACTTT CTGGGCATAT
CCTCCTTCAG CAAAACCACA TTAGGCTGGG AAAACTATTC TGCCTGGAAG
TAATGACAAC TTGCAACCAA CAAGCTTATA AAATACAAA GAATTCTGGA
GCCTATGGCT TCCATTACAT TATTCTTTTA TAGCCTTTTA TGTTCATTAC
CGCATCCAG AGGTGAGAGT CAGACACAAA TATGAAAATA GGTTTCAATG
TTGGAGAGGT AAATCCTAAC AGGAAGGGG TAGGAAAAGA TATAATCCCC
CAATATTAAA ATAAAGATAT TGAAGAAGAA GGATGGGAGA GACTAGGGCT
GTGTCCTTCC TTTTACTCAC CAAAAGAGAA AGTAAGCTCC TATTTGAGTC
AATAGATATT GAGGTCTTGT TATTTGCCAC CAAAGACAGT CTTGTGAGAC
TAAATAGCTA GTAATTCCCT ACCCTGGCAC ACATGCTGCA TACACACAGA
AACACTGCAA ATCCACTGCC TCCTTCCCTC CTCCCTACCC TTCCTTCTCT
CAGCATTTCT ATCCCCGCCT CCTCCTCTTA CCCAAATTTT CCAGCCGATC
ACTGGAGCTG ACTTCCGCAA TCCCGATGGA ATAAATCTAG CACCCCTGAT
GGTGTGCC
```

FIG. 3A

(B) Exon 1 [SEQ ID NO. 3]

CACACTTTGCTGCCGAAACGAAGCCAGACAACAGATTTCCATCAGCAG (C) Intron 1 [SEQ ID NO. 4]

gtaacgtttg caacttccta gatcttttag cttttcattc ctgtcaattc
tctgagtatt agggatgtag tgacttgagg atcacaataa acttttagcc
tctgcagatg aaaacagaga tgcacttctt aggtcattcc ctggctaaat
aaaatctgcc tggaaatctg tagaattcct tgtatgattt atatatatac
atacatgatt gttagtaaaa gcaaagtata tagggaatca tttccccatc
cttcaagagt ggcctttctg cagtgttttc tactttggcc aacaaggatc
aaaacggtta actccttagt gaggaggagg agagtggtat ggggaggtag
tagctcagtg cttcctgttc actgagacat ctcaaagccc ttaacactct
agttttaaa tgtcctactg gacatttgc cagtttgcaa aattacatgt
aaatggacta taagcaattg tgtaagccat atgtcatgct gcaggctgca
aattgttctt aaaatggagg atttgtaatt aagaaagcca atgcaagaaa
tgagtgaagc taactagagt aaacttatga aaagctgtga atttcatcat
catagaacat tgcttttcag tctgaacatt cttctaacaa accttggatc
tgaggcttct tgtcctttgc ggcagccaca gtgggttttt gttgttaggg
gaaaataaaa aaccttgccc gcagcatctg gttaagatta gggcagtttc
ctgcctaagg agggaaggga gagaaaaagg aagaagaaat gcataaggag
aatgaggaga tatacaatgt ctcagaaaac aggaaacatt gtcctatttt
cccttgtcct cttctgacaa gatctgggaa agtaccagaa tttaggcacg
aaagagaaga acgcctcgaa gaaatgatca ggaagcaaaa cttagacgga
aatctctcct ttgtgtattc tgaacccac taccaccttg ctatttgtct
gtctccaagc ctgctaggga ccctggagga aacgcactga gcccattctg
attgtccagt ttctatcccc catttctggt tgtgtacgtg tgtgtgtgtg
tgtgtgtgtg tgtgtgtgtg tgtgtgtgtg tgagagagag agagacagag
agagaaacag agagagtgtg tgttgcctaa atctcccgag agagagagag
agagagagag agagagagag agagagaaaa gagagaaatg gctaaatccc
cctagatcaa agtccttgga accagatgta ccagcatcct atctaaacac
aggcccctcc tgactatcat tgttttatca cccttttcc gtctaccttt
ctcttcctca taaagcctag ttttcctctg tttccctgcc aaatggaaga
gttttcccta actacattct tctgcag

FIG. 3B (D) Exon 2 [SEQ ID NO. 5]

GATGTGGGGGCTCAAGGTTCTGCTGCTACCTGTGGTGAGCTTTGCTCTGTA
CCCTGAGGAGATACTGGACACCCACTGGGAGCTATGGAAGAAGACCCACA
GGAAGCAATATAACAACAAG (E) Intron 2 [SEQ ID NO. 6]

*gtgcc*tggggg   tcctggaggg   ggcatggcag   gaaggctgag   acctgagctc
tctcatctta   gcttccagac   tcccttcttc   aatccaaatg   ctttattcca
agcaaatcag   tccctcttcc   ctaactcatg   ttaacatacg   gttttcattc
ctatgcttca   atcatcctct   tgtcaaactt   gtattccttc   cctttggttt
tataagtgtg   taacattcct   cttttgggaa   gagtcccaag   attaatgctg
ttaatccata   agcaattttt   ctgtctctcc   agagcttgtg   tggttgttta
catattatct   ctcttcttgc   aggctcttaa   ttccatggtt   agttccccaa
ctaaactgta   aacttttatg   attgtgagtt   tcctttattc   tcctaaaacc
cttcacaata   ttacatatga   actgtagaca   gtctatacaa   gtactgacta
tgctttgttt   ag

(F) Exon 3 [SEQ ID NO. 7]

GTGGATGAAATCTCTCGGCGTTTAATTTGGGAAAAAAACCTGAAGTATATTTCCAT
CCATAACCTTGAGGCTTCTCTTGGTGTCCATACATATGAACTGGCTATGAACCACC
TGGGGGACATG (G) Intron 3 [SEQ ID NO. 8]

*gc*aagtatag   cttcagctcc   tgtcccacct   gcaccatttg   ctttagttcc
ctgctgatgc   ctggcctctt   tcttctttgt   cttag

FIG. 3C (H) Exon 4 [SEQ ID NO. 9]

ACCAGTGAAGAGGTGGTTCAGAAGATGACTGGACTCAAAGTACCCCTGTCTCATTC
CCGCAGTAATGACACCCTTTATATCCCAGAATGGGAAGGTAGAGCCCCAGACTCTG
TCGACTATCGAAAGAAAGGATATGTTACTCCTGTCAAAAATCAG (I) Intron 4 [SEQ ID NO. 10]

*gtac*tctcct ttcttctggg tgtgcatatg taatctggca tgaccttttc
cttttctgc tgctttgttc ttgaggtgaa agggcaccag gaaaagaggg
caaggaatta aggtacatct ccccattccc attctgttat ttaacctcat
ttgtttctgt acatttgggt tgtttctggt ttttctttt cttttccctt
tttttttt tttttttt gagatagagt ctcactctgt cgcccaggat
ggagtgcagt ggtgcaatct tggctcactg caacctacac ctcccggtt
caagcgattc tcctgcctca gcctcctgag tagctgagat tacaggcacg
cgccactacg cctggctaat ttttctattt ttatagagat gcgttttcac
catgttggcc aggctggtct tgaactgacc tcaggtgatc cacctgcctc
agcctcccaa agtgctggga ttagagtcat gagccatcgc ggcctggttt
ttctttatta caaatagtgt tgcaataagc accttgtgc atatgttttt
gtgcacatgt acaaatattt atgcaaaata agtcctaaaa ttggaattgt
taggtcacaa ataatccttt ccccccccc aaattttttt tttttttg
agacagcgtc tctgtcaccc aggctggagt ccagtggcgc aatcatggct
cactgcagcc tcaacgtctc aggctcaagt gattctccaa cctcagcctc
cctagtagct gggaattaga agcacatgcc accacaccca gctaatttta
aaaaatttt tgttagagac agggtttgc catgctaccc aagctggtct
caaattcctg ggctcaagca atctgcccgc ttcggcctcc caaagtgcta
ggattacaga catgagccac catgcccagc ccaaaaaagt ttttgcaatc
ttacattctt actagcatga gaatgtcagt tttttcacaa cccaaacaac
acaggattgt atcagcaaga taaacaattg atttaacgtt catttaacaa
acacttttg accccagaa cctaccagat gcagtgttag gcagcagaga

FIG. 3D ctcaagatga ctaagacaca acctgtgtcc tcaggaaatc tcaatctaaa
aaaatagaac aggaaagaaa gaaaaatcta caatctagct gcacaaacaa
taatagctaa tacttttttga gattttattg tttgtcagga acttcttaac
tctttacatg agtttaaata tttaatccct tataacaata ttttatgcat
agagaaactg agacacaggc aaatttagta acttacccgg ggtcacatag
ctactgggtg gcaaagtcag ggttagctcc caggacaaat gcctccacag
ctggtactgt gctctgcttt actgtagcta atagtaaaaa tggtagcaaa
aatcaatagc agtagaacag tgcaacagat attaagcgga agaggaagac
tcacaacaat gacaacattt gtgctgaaat ttttaagaac acatggaatt
tccttcagcc gggtagagag aagatataga aatgtaaaca ccaaagattc
atagtttctc tgtatccctt tcag

(J) Exon 5 [SEQ ID NO. 11]

GGTCAGTGTGGTTCCTGTTGGGCTTTTAGCTCTGTGGGTGCCCTGGAGGGCCAA
CTCAAGAAGAAAACTGGCAAACTCTTAAATCTGAGTCCCCAGAACCTAGTGGATTG
TGTGTCTGAGAATGATGGCTGTGGAGGGGCTACATGACCAATGCCTTCCAATATG
TGCAGAAGAACCGGGGTATTGACTCTGAAGATGCCTACCCATATGTGGGACAG (K) Intron 5 [SEQ ID NO. 12]

gtgagattgc tccacacaat tatacagctc tgttggctcc tccttcccca
gcatgatgtt ttgtactgga acaattcca gaaatactgt tttctgttat
cctatcctgc tttcttgatg gaataatttc ccacagaagg ccaagaagat
ttccacaatc tgggggaatt tagggagctt aagctactat agctcctatt
tgcatctctg ccatggagag aaaacagagg ctaggctacc tacccatag
acttccgagc tgggttctat aaccctctgc tcaattcctc actcccacaa
caaacccaca aaccaccat gctattttca caaattgtgt ggctttattt
tatatgatct cagtgtgagt tttcagaaca tttcagcaaa ttatgtaagt
ttacatgcta acatctataa aatgagagaa aaaacaagtt gcttcatata

FIG. 3E agagataagg gattaactca gttcctcctg catgatcctc tagtcatagg
aaggaaatca tatctgaaag ggaggcaacc tgagggggttt tttatacaca
tagggctggg tctgatagac aatataatgt agggccttca caacagaaac
ctctgaaaca gggacagcaa gtttgagaat aaaaatgatg gctactgtgt
tctaagccgt gtccttagtg cattttttct ttttcttttt ttcatttaat
ctcataacaa ctctgttagg tagacttatc ttgaatgtat aggtgaggaa
atggacactt aaggagataa gacagtataa ttcataccac tagtatgtaa
caatgtaaga tgtatctacc agggatgttt atcttctgca aacattccta
ggtatatctc ccatgcacat gtgcaagaat ttcttactag gatataatgc
cttggaactg aattgtctgg gtcttagggt atgtctgtct tcaactttac
tacacaatgt caaattgttt gccaaaatat ttggaaaaat ttatacctgc
aatgtgtaag aaatcccctt caatcacctt tttatcagta tgtttatctg
gccatttgca tttcttcttc agtgaattaa ctgtttttat ctcttgctca
tttgttttc ttttatttt tttgaaatag ggtcttactc tgttgcccaa
ggctggagtg tggtgataca gtcatagctc actgcagcct ccacttccgg
gctcaagcaa tcctctcgcc tcagcctccc aaatagctag gatataggtg
catgccatca tgcccaccaa tttcaaaaaa cctttgaaat tttttttttg
taaaagctag gcatggtggc tcatgcctgt aatcccagca ctttgggagg
ctgaggtggg aggatcgctt gagcccagga attggaggtc ggcctgatac
aacatagcaa gacctcatct ctacagaaaa aatttttaaa agtagccagg
tatgatggcg tgcatagttc tagctactcc ggaagctggt tgggaggaca
acttgagcct gggagttcaa ggctgctgtg aactgtgatc atgtcactgc
tctctagcct gggtgacaga gtgagaccct gtccccaaaa acaacaaccg
ttttttttgg tagagacatt gtctcgctat gttgccaagg ctagtctcaa
actcctgggc tcaagcaatc ctcccacctc ccaaagtgct gggattatag
atgtaagcca ccatgcctgg cctacccttt tttttttttt ttgaaatgga
agttttgctt ttgtcaccta ggcttgagtg cagtggcgcg atcttggctc
actgcaacct ccacctcctg gattcaagca attctcctgc ctcagcctcc
tgaatagctg ggattatagg cacccgcaac cacgcccggc tagttttgt
atttttagta cagacagggt ttcaccatgt tggccagctg gtcttgaacc
cctgacctca ggtggtccgc ccgcctcggc ctcccaaaat gctgggatta

FIG. 3F

```
aaagtgtgag ccaccatgcc ccaccccttas ctcattttta attggattgt
ttttctctt  tcttagcgat tcttaaaagt  ttaaagagaa tatttggata
caatactatg tatttaaaag ttgaggtctg  tctttccatt cttctcacga
tgtcttcaa  tctagaaaag ttaattttaa  taggcctggc gcggtggctc
acgcttgtaa tcccagcact ttgggaggct  gagatgggtg gatcacaagg
tcaggagatg aagaccatcc tggctaacat  gggtgaaacc ctgtttctac
taaaaataca aaaaattag  ctgggcgtgg  tggcaggtgc ctgtagttcc
agctactcgg gaggctgagg caggagaatg  gcgtgaaccc gggaggtgga
gcttgcagtg agccgagatt gcaccactgc  actccagcct gggcaactga
gcaagactgc gtttcaaaaa aaaaaaaagt  taattttaat atagtaaaat
tagtaaaagg attaattttc cctttgcaat  ttttgtaatg tgtttattc
gtttatgaat ggagaaaggt aagaaaaaat  aaaatttaaa aagaagaga
tgtggccagg tacggtggct cacacctata  atcccagtag tttgggaggc
tgaggcaggc agatcacttg aggtcaggag  tttgagacca gctgggataa
catggtgaaa ccccatctct actaaaaata  caaaaattag ccaggtgtga
ttgcgcacgc ttgtaatccc agcaggctga  ggcaggagaa ttgctcgaac
tcaggaggca gaggttgcag tgagccaaga  tcatgccatt gcactccagc
ctgggtaaca gagactctgt ttcaaaaaaa  taaaaagata aaaaaggaag
agatctgata gggcggccag ataaacattt  taaaggggat ggtattataa
gtttgttccc agcataatgc caggttattc  tgactttaaa gtatcatcac
ataatatctt tttgagtcaa tttccaagat  attctgtttc acttgtaatt
ctgtgtaatt tttggcacca ggaggcatca  gggatttgga gcacatggca
gaaacaaagg catcttgaaa aatatcaagg  cagtagacca ctgtaatctt
aaaatggcat atcaaatgct gctattgctg  ttaatattta gataatgtta
gataatgtat ttttttagag ggtatctcac  tatcttgcac aggctggagt
agagtggcta ttcacagcat gatcacagta  cactaaaggc tcaaactcct
gggcacaaac aatcctcctg cctcagcctg  ctgagtagta gataataagt
tcttgtggat gcaaccttag ggttctgaag  gggtagtctg taggaaaatg
aattgctgaa aagaatacac caccttaaca  tgggctatta ttcgattcca
taattgtggc ttgccaatga aacattgcta  actacctgta aaatatagtg
ttggaagtca taggctaaat tgctaagttc  tttaatctat tttagtgtct
```

FIG. 3G tgttatgtac ttttatattt tgtctttgat gagagcacaa ggatcacacc
agttcccctg atataggtgc agagggccca ggtcttccct ctagctaagc
cttggccttg gcctcctacc cacacagcag ctggtgcctt cctgccccct
gaggctaata catactatgt ggccagaaga tggtttatgc tttttaaaaa
aatcttattt cagaaatctt tccctactgt tttcctccca catttatgtc
ttaaaacacc tgtaggggat tttttttttt tttttttttt tgagatggag
tctcgctctc gcccaggctg gagtgcaatg gcgcgatctt ggctcactgc
aaggtctgcc tcccaggttc acgccattct cctgcctcag cctcccagt
agctgggact acaggcgccc gctaccacgc ctggctaatt ttttgcatt
tttagtagag acagggtttc actgttagcc aggatggtct cgatctcctg
acctcgtgat ccacctcct cagcctccaa agtgctggga ttaacaggca
tggagcccca ccgcactggc ctgtatttgt gaggaagaac agaccctctt
tagaagccct agactgctgc ctctgttagt tcactggcat cactcaaaat
attggttgag tttcttactc actgagttgg tttttatgtg tggtggaagg
cgggaatcct cttttcatat tcgttctcat tgcctattgc tttgtcctag
tcctattaca atcttgtttc ttccag

(L) Exon 6 [SEQ ID NO. 13]

GAAGAGAGTTGTATGTACAACCCAACAGGCAAGGCAGCTAAATGCAGAGGGTACAG
AGAGATCCCCGAGGGGAATGAGAAAGCCCTGAAGAGGGCAGTGGCCCGAGTGGGAC
CTGTCTCTGTGGCCATTGATGCAAGCCTGACCTCCTTCCAGTTTTACAGCAAAG (M) Intron 6 [SEQ ID NO. 14]

gtaagaagct gctgatccta tacagcactg tcttttatga tacaaacttg
atggtttctc gaaggacctt gggtattttc agtacttagt ttttgtattc
acatggaggt ggccagagag aaattaacaa ctgctgcagt atggagcagc
atctctgtgg taaaccctcc tgacacggat ggaattcttc aaacagtctc
ctagactggg agatcccaca gggtgaccct tggattgcat agagcctcac
gctggtagtt tgtattctag

FIG. 3H (N) Exon 7 [SEQ ID NO. 15]

GTGTGTATTATGATGAAAGCTGCAATAGCGATAATCTGAACCATGCGGTTTTGGCA
GTGGGATATGGAATCCAGAAGGGAAACAAGCACTGGATAATTAAAAACAG (O) Intron 7 [SEQ ID NO. 16]

```
gtaatgatgg gaacactact tttgttattc agtcaccctt ttaacactca
acctcacctc cagcttcccg atattccttt ctctgtccca aatcaagaaa
aaattatct  cagagttctc acttctatct tctcagtcag aggctcttaa
ttctcagtct gacacttaat ggccagtgtg ttagtccatt ttgcattgcc
acaaaagaat acccgagact gggtagttta taaagaaacg aggtttgttt
ggctatacaa agcgtggcac tagtatctgc tcagcctctg atgaggcctc
agagctttta ctcatggcag aaggcaaaag agggagcagg catgtcacat
agtgagagag ggagcaagag agagagggag gtgccgactc tttaaagaac
cagctcttgc atgaactaat agagtgagaa ctcactcatc accaaggcga
tggcaccaag ccattccatg aggaatccac tctcataacc caaacacctc
ccactatgcc ccacctccca cattggggat cacatttcag catgagactg
ggaggggaca cacatccaaa ccatatccgc cagacaatag tgctcaatta
tgtgctgggc agatgctccc tgtgtgcaag gtgcttagtg acatacataa
accaacgagc agatgacacc ttcagtgagc tcagagccca ataagacaga
cctaactaac catgagataa agcagtacaa agaaccagca ggagctttgg
aattacgtat ttttactttc ttttgtctct aatgtgatca gtttcttaga
tggtttccat tagcaatctg tctttaacag taggggagca gcgttaaagg
tttaatattc cttttgaaca gttttttttcc ttcaaaatac acttaagata
cacgtatata agaacttgcc aaagattgtg aagagaaaca tttttttagaa
ataagatata aacaaaaaaa gttagtgtta ctttcctatg ttggggaaca
aagaaaactc cagggtacct tgcttcccat ttctctttag caccttgtga
cttttgggga ggggcagatt gataacaatt atagttttcc tttcctggct
gatcaccatt aacctggcag cagcactggc taaatctcct gtccttagtg
ccctccaagg agcaggagcc ctagactctg ggtcgctgac agactcacgc
```

FIG. 3I agtggtgttg ttcaaacctg aagcaacttt ttatatcaca gttccaactc
aaggtgaacc tgagcatctt cccaagtctc ccacagcttc tgtcctgtgt
tgtcccttct cttgactccc aggtccaagc acttaccctg ttctttcatg
atcaggtacc atgtgtggag atagcttcca agagagctgg gaggaagaaa
ggacacaccc gggcaggatc aggaacactg ggggcccctg gagaagggga
gagtggggga gggtacaggt tttaaataaa atgtgttggt aattagagaa
ttgctggttg gggaagagg tctgaaaaca attcaggaag ataaacaaga
caatctctcc tctctcctct ttctcacgtc gtctctcttg tcttctagtc
tcgctactca tttccttagt aatctcatcc actctcatag tttcatccat
ctctcctatg gggtttaccc ccaaatcaag atcaccagct tcagcctcct
tcttatgctc taaactcaca ttttcaagat taatattccc caaatacagc
tctgatcata tcactctccc actcaaaatc cctcactggc tcctcacgat
gatgggtcac agagtaaagg tgaagctttt taaccttgca gtaaaggtaa
ttcaacctga tctcaatctg cctttccaga catctctccc actacaccct
gttaggcaca ctgcttttca gctacatgat cctaacagtg ccccacactt
tcctgcctct gttgttcatt tcacaccctt ccactggcat ccccttccca
caggtcgaaa ttctacttag cctttggct cagctcaaat gccacctctt
acatcaagcc tctaagattc tcttgatcag aaggaatctt tccctccttt
gatacctaca gtattatgcc ttctccctat ttcttgactt taaactcttt
aaagttaaaa aacatcatat tcatttttgt gtaccatcag tacctcgcac
aatactcagt aaatatttta atgaataaat aaactgagag tactaagtat
ttttcttgat tggtcttaca g (P) Exon 8 [SEQ ID NO. 17]

**CTGGGGAGAAAACTGGGGAAACAAAGGATATATCCTCATGGCTCGAAATAAGAACA
ACGCCTGTGGCATTGCCAACCTGGCCAGCTTCCCCAAGATG** End Coding

FIG. 3J (Q) 3' Untranslated sequence cDNA [SEQ ID NO. 18]

TGACTCCAGCCAGCCCAAATCCATCCTGCTCTTCCATTTCCTTCCACGATGGTG
CAGTGTAACGATGCACTTTGGAAGGGAGTTGGTGTGCTATTTTTGAAGCAGATGTG
GTGATACTGAGATTGTCTGTTCAGTTTCCCCATTTGTTTGTGCTTCAAATGATCCT
TCCTACTTTGCTTCTCTCCACCCATGACCTTTTTCCACTGTGGCCATCAGGACTTT
CCCCTGACAGCTGTGTACTCTTAGGCTAAGAGATGTGACTACAGCCTGCCCCTGAC
TGTGTTGTCCCAGGGCTGATGCTGTACAGGTACAGGCTGGAGATTTTCACATAGGT
TAGATTCTCATTCACGGGACTAGTTAGCTTTAAGCACCCTAGAGGACTAGGGTAAT
CTGACTTCTCACTTCCTAAGTTCCCTTCTATATCCTCAAGGTAGAAATGTCTATGT
TTTCTACTCCAATTCATAAATCTATTCATAAGTCTTTGGTACAAGTTTACATGATA
AAAAGAAATGTGATTTGTCTTCCCTTCTTTGCACTTTTGAAATAAAGTATTTATCT
CCTGTCTACAGTTTAATAAATAGCATCTAGTACACATTCA (R) 3' untranslated sequence beyond cDNA [SEQ ID NO. 19]

| | | | | |
|---|---|---|---|---|
| TTTTGTGTTG | GATACTGTGT | TAGGTGCTGG | AGGAAAAAAG | ATGAATAGAA |
| CATCTTCTAT | GTACTTCATG | CGCTCACAGT | CTGGTTGTAG | AGACTGTCAC |
| ATAAACATTT | CATCCCAATT | CATTTATTTG | TTCATTCCTT | CAGCCAATAT |
| ATATTGAGTT | CTTACTCTGT | GCCAAGAACT | GTACTACATT | TCTGGGATTA |
| AGTGGATATA | AGGAGATCTC | AGTGTTTAAT | CTGCCTGAGG | GGAGACTAAA |
| TTAAGTGACA | TGGAAACTTG | GGTCTTGAAA | AACATTTTAA | GGTTATTTTT |
| TCTTTTCTCT | CTCTCTCGCT | CTGTCTTTCT | CTCTCTTTCG | TCAGGGTCTC |
| CCTCTGTTGC | CCAGGCTGGA | GTCAGTGGCA | CTCATAGCTC | ACTGCAGCCT |
| TGATCTCCTG | GGCTCAAGAG | TTCTTCCCAC | CTCAGTCTCC | TAAGTAGCTT |
| GGACTACGG |

FIG. 3K

```
-1108  GCTTTGGCTC CCAAAGGCCT GGGATTACAG GCGTGAACCA CTGCGCCTAG CCTGTTAGCA GCTCTTAAAA TCCAGAGGCA  -1029
-1028  TAAGCCTGTA TTTTGAGGG  TTTATGCATG GAATCCAGCT AGAAACTGAG TCTATTACAG ATCCCATTTA TTATCCTTTC  -949
-948   TATTCCAAGA AGCCTTTTTT TCTCCTTCCC CACATCTGTT TATGGAAGAA AATGAAGTTT GGGGTGTGGT TTGAGAATC   -869
                                                                    AP3        Pu.1
-868   AGCTAGATTC TTATGATCTG TCACATGCTT GGATGTGTGG GAAGCATTTG GAGAAGCTCA TGTGACTTGT CCTAGATTGG  -789
-788   GGATTTTAAT TGAGACAGAT GATGTTTATC GGGCATCCCA CCACCTGAGA GTTTTAGCAA CAGAGTCACA TGTGAGTCCA  -709
-708   TCAGAACTTA CGGCATTGAT TCAAGTGCTG TCATAAATAA CCAGGACTGC TGTTTTTGGT TACTTTTAAA GACAGTTTCA  -629
-628   TCTGGACTTT CTGGGCATAT CCTCCTTCAG CAAAACCACA TTAGGCTGGG AAAACTATTC TGCCTGGAAG TAATGACAAC  -549
                                              AP3-Rv     SP1/H-APF-1
-548   TTGCAACCAA CAAGCTTATA AAAATACAAA GAATTCTGGA GCCTATGGCT TCCATTACAT TATTCTTTTA TAGCCTTTTA  -469
-468   TGTTCATTAC CGCATCCCAG AGGTGAGAGT CAGACACAAA TATGAAAATA GGTTTCAATG TTGGAGAGGT AAATCCTAAC  -389
-388   AGGAAAGGGG TAGGAAAAGA TATAATCCCC CAATATTAAA ATAAAGATAT TGAAGAAGAA GGATGGGAGA GACTAGGGCT  -309
       PEA3        PEA3
-308   GTGTCCTTCC TTTTACTCAC CAAAAGAGAA AGTAAGCTCC TATTTGAGTC AATAGATATT GAGGTCTTGT TATTTGCCAC  -228
       PEA3-Rv AP1-Rv                                      AP1
-227   CAAAGACAGT CTTGTGAGAC TAAATAGCTA GTAATTCCCT ACCCTGGCAC ACATGCTGCA TACACACAGA AACACTGCAA  -149
```

FIG. 3L

-148  ATCCACTGCC TCCTTCCCTC CTCCCTACCC TTCCTTCTCT CAGCATTTCT ATCCCGCCCT CCTCCTCTTA CCCAAATTTT  -69
                                                    PEA3-Rv                    SP1-Rv

-68   CCAGCCGATC ACTGGAGCTG ACTTCCGCAA TCCCGATGGA ATAAATCTAG CACCCCTGAT GGTGTGCCCA CACTTTGCTG  +12
       H-APF-1              Ets-1Rv              AT-Rich Motif                              Exon 1 →

FIG. 3M

| No. | cDNA (bp) | Donor | Acceptor | Intron size (bp) | Amino Acid interrupted |
|---|---|---|---|---|---|
| 1 | 48 | GCAGgtaacgtttgcaact | ...ctacattcttctcagGATG | 1427 | Noncoding |
| 2 | 169 | CAAGgtgcctgggtcctg | ...ctatgcttttgttagGTGG | 462 | Lys40/Val41 |
| 3 | 292 | CATGgcaagtatagcttca | ...tcttcttgtcttagACCA | 85 | Met81/Thr82 |
| 4 | 448 | TCAGgtactctcctttctt | ...ctgtatcccttcagGGTC | 1624 | Gln133/Gly134 |
| 5 | 667 | ACAGgtgagtgagattgct | ...gtttcttccagccagGAAG | 4326 | Gln206/Gly207 |
| 6 | 833 | AAAGgtaagaagctgctga | ...tagtttgtattctagGTGT | 270 | Gly262 |
| 7 | 939 | ACAGgtaatgatgggaaca | ...tgattggtcttacagCTGG | 2270 | Ser297 |

Exon and intron sequences are designated by upper and lower case letters respectively.

FIG. 4

```
          1                                                              50
HumcatK   ........MW GLKVLLLPVV SFA.LYPEEI LDTHWELWKK THRKQYNNKV
RabOC-2   ........MW GLKVLLLPVV SFA.LHPEEI LDTQWELWKK TYSKQYNSKV
HumcatS   .......MKR LVCVLLVCSS AVAQLHKDPT LDHHWHLWKK TYGKQYKEKN
HumcatL   .....MNPTL ILAAFCLGIA S.ATLTFDHS LEAQWTKWKA MHNRLY.GMN
HumcatH   MWATLPLLCA GAWLLGVPVC GAAELSVNSL EKFHFKSWMS KHRKTYST..
HumcatB   .......... .......... .......... ...MWQLWAS LCCLLVLAHA
HumcatD   .......MQP SSLLPLALCL LAAPASALVR IPLHKFTSIR RTMSEVGGSV
HumcatE   .......MKT LLLLLLVLLE LGEAQGSLHR VPLRRHPSLK KKLRARSQ.L
HumcatG   .......MQP LLLLLAFLLP TGAEAGEI.. .......... .....IGGRE 51                                                             100
HumcatK   DEISRRL.IW EKNLKYISIH NLEASLGVHT YELAMNHLGD MTSEEVVQKM
RabOC-2   DEISRRL.IW EKNLKHISIH NLEASLGVHT YELAMNHLGD MTSEEVVQKM
HumcatS   EEAVRRL.IW EKNLKFVMLH NLEHSMGMHS YDLGMNHLGD MTSEEVHSLM
HuncatL   EEGWRRA.VW EKNMKMIELH NQEYREGKHS FTMAMNAFGD MTSEEFRQVM
HumcatH   EEYHHRLQTF ASNWRKINAH N....NGNHT FKMALNQFSD MSFAEIKHEY
HumcatB   RSRPSFHPVS DELVNYVNKR NTTWQAGHNF YNVDMSYLKR LCGTFL....
HumcatD   EDLIAKGPVS KYSQAVPAVT EGPIPEVLKN Y.MDAQYYGE IGIGTPPQCF
HumcatE   SEFWKSHNLD MIQFTESCSM DQSAKEPLIN Y.LDMEYFGT ISIGSPPQNF
HumcatG   SRPHSRPYMA YLQIQSPAGQ SRCG.....G F.LVREDFVL TAAHCWGSNI 101                                                            150
HumcatK   TGLKVPLSHS RSNDTLYPIE WEGRAP.DSV DYRKKG.YVT PVKNQGQCGS
RabOC-2   TGLKVPPSRS HSNDTLYIPD WEGRTP.DSI DYRKKG.YVT PVKNQGQCGS
HumcatS   SSLRVP.SQW QRNIT.YKSN PNRILP.DSV DWREKG.CVT EVKYQGSCGA
HumcatL   NGFQ...NRK PRKGKVFQEP LFYEAP.RSV DWREKG.YVT PVKNQGQCGS
HumcatH   L.WSEPQNCS ATKSNYLRGT ..GPYP.PSV DWRKKGNFVS PVKNQGACGS
HumcatB   ......GGPK PPQRVMFTED LKLPASFDAR EQWPQCPTIK EIRDQGSCGS
HumcatD   TVVFDTGSSN LWVPSIHCKL LDIACWIHHK YNSDKS..ST YVKNGTSFDI
HumcatE   TVIFDTGSSN LWVPSVYCT. .SPACKTHSR FQPSQS..ST YSQPGQSFSI
HumcatG   NVTLG..... .......... ...AHNIQRR ENTQQH..IT ARRAIR..HP 151                                                            200
HumcatK   CWAFSSVGAL EGQLKKKTGK LLN..LSPQN LVDCVSE... ND..GCGGGY
RabOC-2   CWAFSSVGAL EGQLKKKTGK LLN..LSPQN LVDCVSE... NY..GCGGGY
HumcatS   CWAFSAVGAL EAQLKLKTGK LVS..LSAQN LVDCSTEKYG NK..GCNGGF
HumcatL   CWAFSATGAL EGQMFRKTGR LIS..LSEQN LVDC.SGPQG NE..GCNGGL
HumcatH   CWTFSTTGAL ESAIAIATGK MLS..LAEQQ LVDC.AQDFN NY..GCQGGL
HumcatB   CWAFGAVEAI SDRICIHTNA HVSVEVSAED LLTCCGSMCG D...GCNGGY
HumcatD   HYGSGSLSGY LSQDTVSVPC QSASSASALG GVKVERQVFG EATKQPGITF
HumcatE   QYGTGSLSGI IGADQVSV.. ........E GLTVVGQQFG ESVTEPGQTF
HumcatG   QYNQRTIQND IMLLQLSRR. .......... .VRRNRNVNP VALPRAQEGL 201                                                            250
HumcatK   MTNAFQYVQK NRGIDSEDAY .......... .......... ...PYVGQEE
RabOC-2   MTNAFQYVQR NRGIDSEDAY .......... .......... ...PYVGQDE
HumcatS   MTTAFQYIID NKGIDSDASY .......... .......... ...PYKAMDL
HumcatL   MDYAFQYVQD NGGLDSEESY .......... .......... ...PYEATEE
HumcatH   PSQAFEYILY NKGIMGEDTY .......... .......... ...PYQGKDG
HumcatB   PAEAWNF.WT RKGLVSGGLY ESHVGCRPYS IPPCEHHVNG SRPPCTGEGD
HumcatD   IAAKFDGIL. ..GMAYPRIS VNNVLPVFDN LMQQKLVDQN IFSFYLSRDP
HumcatE   VDAEFDGIL. ..GLGYPSLA VGGVTPVFDN MMAQNLVDLP MFSVYMSSNP
HumcatG   RPGTLCTVA. ...G..WGRVS MRRGTDTLRE VQLRVQRDRQ CLRIFGSYDP
```

FIG. 5A

```
              251                                                                    300
HumcatK   SCM....... .YNPTGKAAK CRGYREIPEG N.EKALKRAV ARVGPVSVAI
RabOC-2   SCM....... .YNPTGKAAK CRGYREIPEG N.EKALKRAV ARVGPVSVAI
HumcatS   KCQ....... .YDSKYRAAT CSKYTELPYG R.EDVLKEAV ANKGPVSVGV
HumcatL   SCK....... .YNPKYSVAN DTGFVDIPK. Q.EKALMKAV ATVGPISVAI
HumcatH   YCK....... .FQPGKAIGF VKDVANITIY D.EEAMVEAV ALYNPVSFAF
HumcatB   TPKCSKICEP GYSPTYKQDK HYGYNSYSVS NSEKDIMAEI YKNGPVEGAF
HumcatD   DAQPGGELML GGTDSKYYKG SLSYLNVTRK AYWQVHLDQV EVASGLTLCK
HumcatE   EGGAGSELIF GGYDHSHFSG SLNWVPVTKQ AYWQIALDNI QVGGTVMFCS
HumcatG   RRQ....... .......... ....ICVGDR RERKAAFK.. GDSGGPLLCN 301                                                                    350
HumcatK   DASLTSFQFY SKGVYYDESC ..NSDNLNHA VLAVGYGIQ. ...KGNKHWI
RabOC-2   DASLTSFQFY SKGVYYDENC ..SSDNVNHA VLAVGYGIQ. ...KGNKHWI
HumcatS   DARHPSFFLY RSGVYYEPSC ...TQNVNHG VLVVGYGDL. ...NGKEYWL
HumcatL   DAGHESFLFY KEGIYFEPDC ..SSEDMDHG VLVVGYGFES TESDNHKYWL
HumcatH   EVTQD.FMMY RTGIYSSTSC HKTPDKVNHA VLAVGYG... .EKNGIPYWI
HumcatB   SV.YSDFLLY KSGVYQHVTG EMMGG...HA IRILGWGVE. ...NGTRYW.
HumcatD   EGCEA...IV DTGTSLMVGP VDEVRELQKA IGAVPLIQGE YMIPCEKVST
HumcatE   EGCQA...IV DTGTSLITGP SDKIKQLQNA IGAAP.VDGE YAVECANLNV
HumcatG   NVAHG...IV SYGKSSGVPP ....EVFTRV SSFLPWIRTT MR....SFKL 351                                                                    400
HumcatK   IK......NS WGENWGNKGY ILMARNKNNA CGIAN..LAS FPKM......
RabOC-2   IK......NS WGESWGNKGY ILMARNKNNA CGIAN..LAS FPKM......
HumcatS   VK......NS WGHNFGEEGY IRMARNKGNH CGIAS..FPS YPEI......
HumcatL   VK......NS WGEEWGMGGY VKMAKDRRNH CGIAS..AAS YPTV......
HumcatH   VK......NS WGPQWGMNGY FLIERGK.NM CGLAA..CAS YPIPLV....
HumcatB   VA......NS WNTDWGDNGF FKILRGQ.DH CGIESEVVAG IPRTDQYWEK
HumcatD   LPAITLKLGG KGYKLSPEDY TLKVSQAGKT LCLSGFMGMD IPPPSGPLWI
HumcatE   MPDVTFTING VPYTLSPTAY TLLDFVDGMQ FCSSGFQGLD IHPPAGPLWI
HumcatG   LDQMETPL.. .......... .......... .......... ..........

401                            428
HumcatK   .......... .......... ........
RabOC-2   .......... .......... ........
HumcatS   .......... .......... ........
HumcatL   .......... .......... ........
HumcatH   .......... .......... ........
HumcatB   I......... .......... ........
HumcatD   LGDVFIGRYY TVFDRDNNRV GFAEAARL
HumcatE   LGDVFIRQFY SVFDRGNNRV GLAPAVP.
HumcatG   .......... .......... ........
```

FIG. 5B

[SEQ ID NO: 20]

| Intron(s) Amplified | Oligonucleotide Sequence (5' to 3') | cDNA Location | |
|---|---|---|---|
| 1 | CCGAAACGAAGCCAGACAAC(S) | exon 1 | SEQ ID NO.:21 |
|   | GCTCACCACAGGTAGCAGCAG(AS) | exon 2 | SEQ ID NO.:22 |
| 2 | CTGCTGCTACCTGTGGTGAGC(S) | exon 2 | SEQ ID NO.:23 |
|   | CCCAAATTAAACGCCGAGAG(AS) | exon 3 | SEQ ID NO.:24 |
| 3 | CTCTCGGCGTTTAATTTGGG(S) | exon 3 | SEQ ID NO.:25 |
|   | GGTACTTTGAGTCCAGTCATC(AS) | exon 4 | SEQ ID NO.:26 |
| 4 | CCAGACTCTGTCGACTATCG(S) | exon 4 | SEQ ID NO.:27 |
|   | CACATATGGGTAGGCATCTTC(AS) | exon 5 | SEQ ID NO.:28 |
| 5&6 | GAAGATGCCTACCCATATGTG(S) | exon 5 | SEQ ID NO.:29 |
|   | GTTACATTATCGCTATTGCAC(AS) | exon 7 | SEQ ID NO.:30 |
| 7 | GCAAAGGTGTGTATTATGATG(S) | exon 7 | SEQ ID NO.:31 |
|   | GCCGTTGTTCTTATTTCGAGC(AS) | exon 8 | SEQ ID NO.:32 |

FIG. 7

CATHEPSIN K GENE

RELATED APPLICATIONS

This application claims the benefit of U.S. application No. 60/019,942 filed Jun. 14, 1996, U.S. Provisional Application No. 60/020,273 filed Jun. 17, 1996 and U.S. Provisional Application No. 60/026,083 filed Aug. 26, 1996.

This invention relates, in part, to newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to polynucleotides and polypeptides of human cathepsin K, especially genomic sequences of cathepsin K, and most especially promoter and intronic sequences.

BACKGROUND OF THE INVENTION

Bone resorption involves the simultaneous removal of both the mineral and the organic constituents of the extracellular matrix. This occurs mainly in an acidic phagolysosome-like extracellular compartment covered by the ruffled border of osteoclasts. Barron, et al., J. Cell Biol., 101:2210–22, (1985). Osteoclasts are multinucleate giant cells that play key roles in bone resorption. Attached to the bone surface, osteoclasts produce an acidic microenvironment between osteoclasts and bone matrix. In this acidic microenvironment, bone minerals and organic components are solubilized. Organic components, mainly type-I collagen, are thought to be solubilized by protease digestion. There is evidence that cysteine proteinases may play an important role in the degradation of organic components of bone. Among cysteine proteinases, cathepsins B, L, H, and S can degrade type-I collagen in the acidic condition. Etherington, D. J. Biochem. J., 127, 685–692 (1972). Cathepsin L is the most active of the lysosomal cysteine proteases with regard to its ability to hydrolyze azocasein, elastin, and collagen.

Cathepsins are proteases that function in the normal physiological as well as pathological degradation of connective tissue. Cathepsins play a major role in intracellular protein degradation and turnover, bone remodeling, and prohormone activation. Marx, J. L., Science. 235:285–286 (1987). Cathepsin B, H, L and S are ubiquitously expressed lysosomal cysteine proteinases that belong to the papain superfamily. They are found at constitutive levels in many tissues in the human including kidney, liver, lung and spleen. Some pathological roles of cathepsins include an involvement in glomerulonephritis, arthritis, and cancer metastasis. Sloan, B. F., and Honn, K. V., Cancer Metastasis Rev., 3:249–263 (1984). Greatly elevated levels of cathepsin L and B mRNA and protein are seen in tumor cells. Cathepsin L mRNA is also induced in fibroblasts treated with tumor promoting agents and growth factors. Kane, S. E. and Gottesman, M. M. Cancer Biology, 1:127–136 (1990).

The gene expression and cellular content of a noncysteine protease, cathepsin D, in Alzheimer's disease brain showed evidence for early up-regulation of the endosomallysosomal system. Cataldo A. M., et al., Neuron, 1995, 14 (3), 671–680).

In vitro studies on bone resorption have shown that cathepsins L and B may be involved in the remodelling of this tissue. These lysosomal cysteine proteases digest extracellular matrix proteins such as elastin, laminin, and type I collagen under acidic conditions. Osteoclast cells require this activity to degrade the organic matrix prior to bone regeneration accomplished by osteoblasts. Several natural and synthetic inhibitors of cysteine proteinases have been effective in inhibiting the degradation of this matrix.

The isolation of cathepsins and their role in bone resorption has been the subject of an intensive study. OC-2 has recently been isolated from pure osteoclasts from rabbit bones. The OC-2 was found to encode a possible cysteine proteinase structurally related to cathepsins L and S. Tezuka, K., et al., J. Biol. Chem., 269:1106–1109, (1994).

An inhibitor of cysteine proteinases and collagenase, Z-Phe-Ala-CHN$_2$ has been studied for its effect on the resorptive activity of isolated osteoclasts and has been found to inhibit resorption pits in dentine. Delaisse, J. M. et al., Bone, 8:305–313 (1987). Also, the effect of human recombinant cystatin C, a cysteine proteinase inhibitor, on bone resorption in vitro has been evaluated, and has been shown to significantly inhibit bone resorption which has been stimulated by parathyroid hormone. Lerner, U. H. and Grubb Anders, Journal of Bone and Mineral Research, 7:433–439, (1989). Further, a cDNA clone encoding the human cysteine protease cathepsin L has been recombinantly manufactured and expressed at high levels in $E.$ $coli$ in a T7 expression system. Recombinant human procathepsin L was successfully expressed at high levels and purified as both procathepsin L and active processed cathepsin L forms. Information about the possible function of the propeptide in cathepsin L folding and/or processing and about the necessity for the light chain of the enzyme for protease activity was obtained by expressing and purifying mutant enzymes carrying structural alterations in these regions. Smith, S. M. and Gottesman, M. M., J. Bio Chem., 264:20487–20495, (1989). There has also been reported the expression of a functional human cathepsin S in $Saccharomyces$ $cerevisiae$ and the characterization of the recombinant enzyme. Bromme, D. et al., J. Biol. Chem., 268:4832–4838 (1993).

SUMMARY OF THE INVENTION

Toward these ends, and others, it is an object of the present invention to provide polypeptides, inter alia, that have been identified as novel cathepsin K by homology between the amino acid sequence set out in FIG. 5 and known amino acid sequences of other proteins such as rabbit OC-2 and human cathepsin O cDNA. Tezuka, K., et al., J. Biol. Chem., 269:1106–1109, (1994).

It is a further object of the invention, moreover, to provide polynucleotides that encode cathepsin K, particularly polynucleotides that encode the polypeptide herein designated cathepsin K.

In a particularly preferred embodiment of this aspect of the invention the polynucleotide comprises the region encoding human cathepsin K in the sequence set out in FIG. 1 [SEQ ID NO: 1] or in the genomic DNA (herein "gDNA") in ATCC deposit No. 98035 (referred to herein as the deposited clone).

In accordance with this aspect of the invention there are provided isolated nucleic acid molecules encoding human cathepsin K, including mRNAs, cDNAs, genomic DNAs and, in further embodiments of this aspect of the invention, biologically, diagnostically, clinically or therapeutically useful variants, analogs or derivatives thereof, or fragments thereof, including fragments of the variants, analogs and derivatives.

Among the particularly preferred embodiments of this aspect of the invention are naturally occurring allelic variants of human cathepsin K.

It also is an object of the invention to provide cathepsin K polypeptides, particularly human cathepsin K polypeptides, that cause or are associated with disease, for example, osteoporosis, Paget's disease, Gaucher's disease, CNS inflammation, Alzheimer's disease, hyperparathyroidism, bone degradation, metastatic tumors, rhemuatoid arthritis, osteoarthritis, peridontal disease and degradation of bone implants and bone protheses, particularly dental implants.

In accordance with this aspect of the invention there are provided novel polypeptides of human origin referred to herein as cathepsin K as well as biologically, diagnostically or therapeutically useful fragments, variants and derivatives thereof, variants and derivatives of the fragments, and analogs of the foregoing.

Among the particularly preferred embodiments of this aspect of the invention are variants of human cathepsin K encoded by naturally occurring alleles of the human cathepsin K gene.

It is another object of the invention to provide a process for producing the aforementioned polypeptides, polypeptide fragments, variants and derivatives, fragments of the variants and derivatives, and analogs of the foregoing.

In a preferred embodiment of this aspect of the invention there are provided methods for producing the aforementioned cathepsin K polypeptides comprising culturing host cells having expressibly incorporated therein an exogenously-derived human cathepsin K-encoding polynucleotide under conditions for expression of human cathepsin K in the host and then recovering the expressed polypeptide.

In accordance with yet another object of the invention there are methods to determine drug responsiveness of individuals having or suspected of having a defect in the cathepsin K gene.

In accordance with yet another object the invention there are provided products, compositions, processes and methods that utilize the aforementioned polypeptides and polynucleotides for research, biological, clinical and therapeutic purposes, inter alia.

In accordance with certain preferred embodiments of this aspect of the invention, there are provided products, compositions and methods, inter alia, for, among other things: assessing cathepsin K expression in cells by determining cathepsin K polypeptides of cathepsin K-encoding mRNA or hnRNA in vitro, ex vivo or in vivo by exposing cells to cathepsin K polypeptides, polynucleotides or antibodies as disclosed herein; assaying genetic variation and aberrations, such as defects, in cathepsin K polynucleotides, genes and gene control sequences; and administering a cathepsin K polypeptide or polynucleotide to an organism to augment cathepsin K function or remediate cathepsin K dysfunction.

In accordance with certain preferred embodiments of this and other aspects of the invention there are provided probes that hybridize specifically to human cathepsin K sequences.

In certain additional preferred embodiments of this aspect of the invention there are provided antibodies against cathepsin K polypeptides. In certain particularly preferred embodiments in this regard, the antibodies are highly selective for human cathepsin K.

In accordance with another aspect of the present invention, there are provided cathepsin K agonists. Among preferred agonists are molecules that mimic cathepsin K, that bind to cathepsin K-binding molecules or receptor molecules, and that elicit or augment cathepsin K-induced responses. Also among preferred agonists are molecules that interact with cathepsin K or cathepsin K polypeptides, or with other modulators of cathepsin K activities, and thereby potentiate or augment an effect of cathepsin K or more than one effect of cathepsin K.

In accordance with yet another aspect of the present invention, there are provided cathepsin K antagonists. Among preferred antagonists are those which mimic cathepsin K so as to bind to cathepsin K receptor or binding molecules but not elicit a cathepsin K-induced response or more than one cathepsin K-induced response. Also among preferred antagonists are molecules that bind to or interact with cathepsin K so as to inhibit an effect of cathepsin K or more than one effect of cathepsin K.

The agonists and antagonists may be used to mimic, augment or inhibit the action of cathepsin K polypeptides. They may be used, for instance, to treat osteoporosis, Paget's disease, Gaucher's disease, CNS inflammation, Alzheimer's disease, hyperparathyroidism, bone degradation, metastatic tumors, and degradation of bone implants and bone protheses, particularly dental implants. Such antagonists may be particularly useful to treat osteoporosis, Paget's disease, Gaucher's disease, Alzheimer's disease, hyperparathyroidism, bone degradation, metastatic tumors, CNS inflammation, rhemuatoid arthritis, osteoarthritis, periodontal disease and degradation of bone implants and bone protheses, particularly dental implants.

In a further aspect of the invention there are provided compositions comprising a cathepsin K polynucleotide or a cathepsin K polypeptide for administration to cells in vitro, to cells ex vivo and to cells in vivo, or to a multicellular organism. In certain particularly preferred embodiments of this aspect of the invention, the compositions comprise a cathepsin K polynucleotide for expression of a cathepsin K polypeptide in a host organism for treatment of disease. Particularly preferred in this regard is expression in a human patient for treatment of a dysfunction associated with aberrant endogenous activity of cathepsin K or to provide therapeutic.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIG. 1 shows the genomic nucleotide sequence of human cathepsin K. [SEQ ID NO: 1]. Exons are capitalized and underlined. Intron sequence is in lower case letters.

FIG. 2 shows the nucleotide, exon-intron boundaries and deduced amino acid sequence of human cathepsin K.

FIG. 3 (A–M) shows structural features of cathepsin K [SEQ ID NO: 2–19].

FIG. 4 shows the intron-exon junctions.

FIG. 5 shows the regions of similarity between amino acid sequences of cathepsin K, human cathepsins S, L, H, B, D, E, G and rabbit OC2 polypeptides.

FIG. 6 shows the deduced amino acid sequence of human cathepsin K.

FIG. 7 shows the PCR primers to amplify genomic DNA.

GLOSSARY

The following illustrative explanations are provided to facilitate understanding of certain terms used frequently herein, particularly in the examples. The explanations are provided as a convenience and are not limitative of the invention.

DIGESTION of DNA refers to catalytic cleavage of the DNA with a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 $\mu$g of plasmid or DNA fragment is digested with about 2 units of enzyme in about 20 ml of reaction buffer. For the purpose of isolating DNA fragments for plasmid construction, typically 5 to 50 $\mu$g of DNA are digested with 20 to 250 units of enzyme in proportionately larger volumes.

Appropriate buffers and substrate amounts for particular restriction enzymes are described in standard laboratory manuals, such as those referenced below, and they are specified by commercial suppliers.

Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well known methods that are routine for those skilled in the art.

GENETIC ELEMENT generally means a polynucleotide comprising a region that encodes a polypeptide or a region that regulates transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome; not in their natural state but, rather, following manipulation such as isolation, cloning and introduction into a host cell in the form of purified DNA or in a vector, among others.

IDENTITY means the degree of sequence relatedness between two polypeptide or two polynucleotides sequences as determined by the identity of the match between two strings of such sequences. Identity can be readily calculated. While there exist a number of methods to measure identity between two polynucleotide or polypeptide sequences, the term "identity" is well known to skilled artisans (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). Methods commonly employed to determine identity between two sequences include, but are not limited to disclosed in Guide to Huge Computers, Martin J. Bishop, ed., Academic Press, San Diego, 1994, and Carillo, H., and Lipman, D., SIAM J. Applied Math., 48:1073 (1988). Preferred methods to determine identity are designed to give the largest match between the two sequences tested. Such methods are codified in computer programs. Preferred computer program methods to determine identity between two sequences include, but are not limited to, GCG program package (Devereux, J., et al., *Nucleic Acids Research* 12(1):387 (1984)), BLASTP, BLASTN, FASTA (Atschul, S. F. et al., *J. Molec. Biol.* 215:403 (1990)).

ISOLATED means altered "by the hand of man" from its natural state; i.e., that, if it occurs in nature, it has been changed or removed from its original environment, or both.

For example, a naturally occurring polynucleotide or a polypeptide naturally present in a living animal in its natural state is not "isolated," but the same polynucleotide or polypeptide separated from some or all of the coexisting materials of its natural is "isolated", as the term is employed herein.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

LIGATION refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, New York (1989) and Maniatis et al., pg. 146, as cited below.

OLIGONUCLEOTIDE(S) refers to relatively short polynucleotides. Often the term refers to single-stranded deoxyribonucleotides, but it can refer as well to single-, double-, or triple-stranded ribonucleotides, antisense polynucleotides, RNA:DNA hybrids and double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

PLASMIDS generally are designated herein by a lower case letter p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single-and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS—STRUCTURE AND MOLECULAR PROPERTIES, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York (1983); Seifter et al., Analysis for protein modifications and nonprotein cofactors, Meth. Enzymol. 182:626–646 (1990) and Rattan et al., Protein Synthesis: Posttranslational Modifications and Aging, Ann. N.Y. Acad. Sci. 663:48–62 (1992).

It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as *E. coli*. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to express efficiently mammalian proteins having native patterns of glycosylation, inter alia. Similar considerations apply to other modifications.

It will be appreciated that the same type of modification may be present in the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

VARIANT(S) of polynucleotides or polypeptides, as the term is used herein, are polynucleotides or polypeptides that differ from a reference polynucleotide or polypeptide, respectively. Variants in this sense are described below and elsewhere in the present disclosure in greater detail.

(1) A polynucleotide that differs in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

(2) A polypeptide that differs in amino acid sequence from another, reference polypeptide. Generally, differences are limited so that the sequences of the reference and the variant are closely similar overall and, in many region, identical.

A variant and reference polypeptide may differ in amino acid sequence by one or more substitutions, additions, deletions, fusions and truncations, which may be present in any combination.

RECEPTOR MOLECULE, as used herein, refers to molecules which bind or interact specifically with cathepsin K polypeptides of the present invention, including not only classic receptors and enzymatic substrates, both of which are preferred, but also other molecules that specifically bind to or interact with polypeptides of the invention (which also may be referred to as "binding molecules" and "interaction molecules," respectively and as "cathepsin K binding molecules" and "cathepsin K interaction molecules." These cathepsin K binding molecules also include, for example, cathepsin K substrate analogs. Binding between polypeptides of the invention and such molecules, including receptor or binding or interaction molecules may be exclusive to polypeptides of the invention, which is very highly preferred, or it may be highly specific for polypeptides of the invention, which is highly preferred, or it may be highly specific to a group of proteins that includes polypeptides of the invention, which is preferred, or it may be specific to several groups of proteins at least one of which includes polypeptides of the invention.

Receptors also may be non-naturally occurring, such as antibodies and antibody-derived reagents that bind specifically to polypeptides of the invention.

DESCRIPTION OF THE INVENTION

The present invention relates to novel cathepsin K polypeptides and polynucleotides, among other things, as described in greater detail below. In particular, the invention relates to polypeptides and polynucleotides of a novel human cathepsin K, which is related by amino acid sequence homology to rabbit OC-2 and human cathepsin O cDNA. Tezuka, K., et al., J. Biol. Chem., 269:1106–1109, (1994). The invention relates especially to cathepsin K having the nucleotide sequences set out in FIG. 1 [SEQ ID NO: 1], and to the cathepsin K nucleotide sequences of the gDNA in ATCC Deposit No. 98035, which is herein referred to as "the deposited clone" or as the "gDNA of the deposited clone." It will be appreciated that the nucleotide sequences set out in FIG. 1 [SEQ ID NO: 1] were obtained by sequencing the gDNA of the deposited clone, as more specifically set forth elsewhere herein. Hence, the sequence of the deposited clone is controlling as to any discrepancies between the two.

Polynucleotides

In accordance with one aspect of the present invention, there are provided isolated polynucleotides which encode the cathepsin K polypeptide having the deduced amino acid sequence of FIG. 2 [SEQ ID NO: 20] (see also FIG. 6 for the deduced amino acid sequence) or the cathepsin K polypeptide encoded by the gDNA in the deposited clone.

Using the information provided herein, such as the polynucleotide sequence set out in FIG. 1 [SEQ ID NO: 1], a polynucleotide of the present invention encoding human cathepsin K polypeptide may be obtained using standard cloning and screening procedures, such as those for cloning gDNAs using DNA from cells of a human as starting material. Illustrative of the invention, the polynucleotide set out in FIG. 1 [SEQ ID NO: 1] was discovered in a human gDNA library as described in Example 1.

Human cathepsin K of the invention is structurally related to other proteins of the cathepsin family, as shown by the results of sequencing the gDNA encoding human cathepsin K in the deposited clone. The gDNA sequence thus obtained is set out in FIG. 1 [SEQ ID NO: 1]. It contains a non-contiguous open reading frame encoding, after intron removal, but including all exons, a protein of about 329 amino acid residues.

Polynucleotides of the present invention may be in the form of RNA, such as mRNA or hnRNA, or in the form of DNA, including, for instance, cDNA and gDNA obtained by cloning or produced by chemical synthetic techniques or by a combination thereof. The DNA may be triple-stranded, double-stranded or single-stranded.

Single-stranded DNA may be the coding strand, also known as the sense strand, or it may be the non-coding strand, also referred to as the anti-sense strand.

The coding sequence which encodes the polypeptide may be identical to the exon sequence of the polynucleotide shown in FIG. 1 [SEQ ID NO: 1 ] or that of the deposited clone. It also may be a polynucleotide with a different sequence, which, as a result of the redundancy (degeneracy) of the genetic code, encodes the polypeptide of the DNA of FIG. 2 [SEQ ID NO: 20] or of the deposited gDNA, including, but not limited to, splice variants transcribed from such gDNA.

Polynucleotides of the present invention which encode the polypeptide of FIG. 1 [SEQ ID NO: 1] or the polypeptide encoded by the deposited gDNA may include, but are not limited to the coding sequence for the mature polypeptide, by itself; the coding sequence for the mature polypeptide and additional coding sequences, such as those encoding a leader or secretory sequence, such as a pre-, or pro- or prepro-protein sequence;

the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in the vector pQE-9, among others, many of which are commercially available. As described in Gentz et al., Proc. Natl. Acad. Sci., USA 86:821–824 (1989), for instance, hexa-histidine provides for convenient purification of the fusion protein. The HA tag corresponds to an epitope derived of influenza hemagglutinin protein, which has been described by Wilson et al., Cell 37:767 (1984), for instance.

In accordance with the foregoing, the term "polynucleotide encoding a polypeptide" as used herein encompasses polynucleotides which include a sequence encoding a polypeptide of the present invention, particularly the human cathepsin K having the amino acid sequence set out in FIG. 2 [SEQ ID NO: 20] or the amino acid sequence of the human cathepsin K encoded by the gDNA of the deposited clone. The term encompasses polynucleotides that include a single continuous region or discontinuous regions encoding the polypeptide (for example, interrupted by introns) together with additional regions, that also may contain coding and/or non-coding sequences.

The present invention further relates to variants of the herein above described polynucleotides which encode for fragments, analogs and derivatives of the polypeptide having the deduced amino acid sequence of FIG. 2 [SEQ ID NO: 20] or the polypeptide encoded by the exons of the gDNA of the deposited clone, including, but not limited to, splice variants transcribed from such gDNA. A variant of the polynucleotide may be a naturally occurring variant such as a naturally occurring allelic variant or splice variant, or it may be a variant that is not known to occur naturally. Such non-naturally occurring variants of the polynucleotide may be made by mutagenesis techniques, including those applied to polynucleotides, cells or organisms. Such non-naturally occurring variants of the polynucleotide may be made by modifying splice acceptor, donor and/or branch sites, or by expressing the gDNA in cells where it is not naturally expressed, or cell extracts made from such cells.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotide sequence of cathepsin K set out in FIG. 1 [SEQ ID NO: 1] or the polynucleotide sequence of cathepsin K of the gDNA of the deposited clone; variants, analogs, derivatives and fragments thereof, and fragments of the variants, analogs and derivatives.

Further particularly preferred in this regard are polynucleotides encoding cathepsin K variants, analogs, derivatives and fragments, and variants, analogs and derivatives of the fragments, which have the amino acid sequence of the cathepsin K polypeptide of FIG. 2 [SEQ ID NO: 20] or of the deposit in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the cathepsin K. Also especially preferred in this regard are conservative substitutions. Most highly preferred are polypeptides having the amino acid sequence of FIG. 2 [SEQ ID NO: 20] or of the deposit, without substitutions.

Further preferred embodiments of the invention are polynucleotides that are at least 70% identical to a polynucleotide encoding the cathepsin K polypeptide having the amino acid sequence set out in FIG. 2 [SEQ ID NO: 20], or variants, close homologs, derivatives and analogs thereof, as described above, and polynucleotides which are complementary to such polynucleotides. Alternatively, most highly preferred are polynucleotides that comprise a region that is at least 80% identical to a polynucleotide encoding the cathepsin K polypeptide of the gDNA of the deposited clone and polynucleotides complementary thereto. In this regard, polynucleotides at least 90% identical to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Still further preferred embodiments of the invention are polynucleotides comprising cathepsin K intron polynucleotide sequences, particularly polynucleotides comprising intron 1 [SEQ ID NO: 4], 2 [SEQ ID NO: 6], 3 [SEQ ID NO: 8], 4[SEQ ID NO: 10], 5 [SEQ ID NO: 12], 6 [SEQ ID NO: 14] or 7[SEQ ID NO: 16], having the intron polynucleotide sequence set out in FIGS. 1 [SEQ ID NO: 1] and 3 [SEQ ID NO: 2–19], or variants, close homologs, derivatives and analogs thereof, as described above, and polynucleotides which are complementary to such polynucleotides. Other preferred embodiments of the invention are polynucleotides comprising cathepsin K intron 1[SEQ ID NO: 4], 2 [SEQ ID NO: 6], 3 [SEQ ID NO: 8], 4 [SEQ ID NO: 10], 5 [SEQ ID NO: 12], 6 [SEQ ID NO: 14] or 7[SEQ ID NO: 16], operatively linked to the exon of a gene other than cathepsin K, or joining a cathepsin K exon and an exon of another gene.

Still other preferred embodiments of the invention are polynucleotides comprising cathepsin K exon polynucleotide sequences, particularly polynucleotides comprising exon 1 [SEQ ID NO: 3], 2 [SEQ ID NO: 5], 3 [SEQ ID NO: 7], 4 [SEQ ID NO: 9], 5 [SEQ 11], 6 [SEQ ID NO: 13], 7 [SEQ ID NO: 15] or 8 [SEQ ID NO: 17], having the exon polynucleotide sequence set out in FIGS. 1 [SEQ ID NO: 1] and 3 [SEQ ID NO: 2–19], or variants, close homologs, derivatives and analogs thereof, as described above, and polynucleotides which are complementary to such polynucleotides. Other preferred embodiments of the invention are polynucleotides comprising cathepsin K exon 1 [SEQ ID NO: 3], 2 [SEQ ID NO: 5], 3 [SEQ ID NO: 7], 4 [SEQ ID NO: 9], 5 [SEQ ID NO: 11], 6 [SEQ ID NO: 13], 7 [SEQ ID NO: 15] or 8 [SEQ ID NO: 17], operatively linked to the intron of a gene other than cathepsin K.

More preferred embodiments of the invention are differentially spliced polynucleotides, particularly those comprising any one or more of the following exon-exon pairs:1-3, 1-4, 1-5, 1-6, 1-7, 1-8, 2-4, 2-5, 2-6, 2-7, 2-8, 3-4, 3-5, 3-6, 3-7, 3-8, 4-5, 4-6, 4-7, 4-8, 5-7, 5-8, or 6-8. Particularly preferred embodimen invention are differentially spliced polynucleotides which encode polypeptides which function in cells, especially those which have a biological activity of cathepsin K, most especially those expressed in human cells.

Polynucleotides comprising exon-exon pairs may be a naturally occurring variant such as a naturally occurring splice variant, or it may be a variant that is not known to occur naturally. Such non-naturally occurring variants of the polynucleotide may be made by mutagenesis techniques, including those applied to polynucleotides, cells or organisms. Such non-naturally occurring variants of the polynucleotide may be made by modifying splice acceptor, donor and/or branch sites, or by expressing the gDNA in cells where it is not naturally expressed, or cell extracts made from such cells. Exon-exon pairs can be full, fused exons or can be fused fragments of exons with a splice junction present. Preferred exon-exon pairs comprising exon fragments may be made from at least two exons, one of which comprises an operable splice donor site and the other of which comprises an operable splice acceptor site and which both are operatively linked by an intron.

Particularly preferred embodiments in this respect, moreover, are polynucleotides which encode polypeptides which retain substantially the same biological function or activity as the mature polypeptide encoded by the cDNA of FIG. 2 [SEQ ID NO: 20] or the gDNA of the deposited clone.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as a hybridization probe for cDNA and genomic DNA to isolate full-length cDNAs and genomic clones encoding cathepsin K and to isolate cDNA and genomic clones of other genes that have a high sequence similarity to the human cathepsin K gene. Such probes generally will comprise at least 15 bases. Preferably, such probes will have at least 30 bases and may have at least 50 bases. Particularly preferred probes will have at least 30 bases and will have 50 bases or less.

For example, the coding region of the cathepsin K gene may be isolated by screening using the known DNA sequence to synthesize an oligonucleotide probe. A labeled oligonucleotide having a sequence complementary to that of a gene of the present invention is then used to screen a library of human cDNA, genomic DNA or mRNA to determine which members of the library the probe hybridizes to.

The polynucleotides and polypeptides of the present invention may be employed as research reagents and materials for discovery of treatments and diagnostics to human disease, as further discussed herein relating to polynucleotide assays, inter alia.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Deposited Materials

A deposit containing a human cathepsin K gDNA has been deposited with the American Type Culture Collection, as noted above. Also as noted above, the gDNA deposit is referred to herein as "the deposited clone" or as "the gDNA of the deposited clone."

The deposited clone was deposited with the American Type Culture Collection, 12301 Park Lawn Drive, Rockville, Md. 20852, USA, on Apr. 26, 1996, and assigned ATCC Deposit No. 98035.

The deposited material is a P1 cosmid that contains the full length cathepsin K gDNA, referred to as "P1SacB2CatK/P129" upon deposit.

The deposit has been made under the terms of the Budapest Treaty on the international recognition of the deposit of micro-organisms for purposes of patent procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. section 112.

The sequence of the polynucleotides contained in the deposited material, as well as the amino acid sequence of the polypeptide encoded thereby, are controlling in the event of any conflict with any description of sequences herein.

A license may be required to make, use or sell the deposited materials, and no such license is hereby granted.

Polypeptides

The present invention further relates to a human cathepsin K polypeptide which has the deduced amino acid sequence of FIG. 2 [SEQ ID NO: 20], which is encoded by an unspliced or differentially spliced hnRNA or MRNA transcribed from the sequence of FIG. 1 [SEQ ID NO: 1], or which has the amino acid sequence encoded by the deposited clone. Also provided are polypetides encoded by the cathepsin K gDNA comprising missense or nonsense mutations, or those polypeptides encoded by unspliced or partially spliced hnRNAs which still comprise at least one intron, particularly those polypeptides which are naturally found in cells, especially human cells. Frameshift mutations have been shown to be associated with disease (Hol, FA, et al. Journal of Medical Genetics, 1995, 32 (1), 52–56).

Preferred polypeptides provided by the invention are encoded by differentially spliced polynucleotides, particularly those polypeptides encoded by polynucleotides comprising any one or more of the following exon-exon pairs: 1-3, 1-4, 1-5, 1-6, 1-7, 1-8, 2-4, 2-5, 2-6, 2-7, 2-8, 3-4, 3-5, 3-6, 3-7, 3-8, 4-5, 4-6, 4-7, 4-8, 5-7, 5-8, or 6–8. Particularly preferred embodiments of the invention are polypeptides encoded by differentially spliced polynucleotides, which polypeptides function in cells, especially those which have a biological activity of cathepsin K, most especially those expressed in human cells.

Still further preferred embodiments of the invention are polypeptides encoded by polynucleotides comprising exon polynucleotide sequences, particularly polynucleotides comprising cathepsin K exon 1 [SEQ ID NO: 3], 2 [SEQ ID NO: 5], 3 [SEQ ID NO: 7], 4 [SEQ ID NO: 9], 5 [SEQ ID NO: 11], 6 [SEQ ID NO: 13], 7 [SEQ ID NO: 15] or 8 [SEQ ID NO: 17], having the exon polynucleotide sequence set out in FIGS. 1 [SEQ ID NO: 1] and 3 [SEQ ID NO: 2–19], or variants, close homologs, derivatives and analogs thereof, as described above, and polypeptides encoded by polynucleotides which are complementary to such polynucleotides. Other preferred embodiments of the invention are polypeptides encoded by polynucleotides comprising comprising cathepsin K exon exon 1 [SEQ ID NO: 3], 2 [SEQ ID NO: 5], 3 [SEQ ID NO: 7], 4 [SEQ ID NO: 9], 5 [SEQ ID NO: 11ID NO: 13], 7 [SEQ ID NO: 15] or 8 [SEQ ID NO: 17], operatively liked to the intron of a gene other then cathepsin K, or joined to an exon of another gene.

The invention also relates to fragments, analogs and derivatives of these polypeptides. The terms "fragment," "derivative" and "analog" when referring to the polypeptide of FIG. 2 [SEQ ID NO: 20], a polypeptide encoded by an unspliced or differentially spliced hnRNA or mRNA transcribed from the sequence of FIG. 1 [SEQ ID NO: 1], or that encoded by the deposited gDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments it is a recombinant polypeptide.

The fragment, derivative or analog of the polypeptide of FIG. 2 [SEQ ID NO: 20], or that encoded by an unspliced or differentially spliced hnRNA or mRNA transcribed from the sequence of FIG. 1 [SEQ ID NO: 1], or that encoded by the gDNA in the deposited clone may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of cathepsin K set out in FIG. 2 [SEQ ID NO: 20], variants, analogs, derivatives and fragments thereof, and variants, analogs and derivatives of the fragments. Alternatively, particularly preferred embodiments of the invention in this regard are polypeptides having the amino acid sequence of the cathepsin K of the gDNA in the deposited clone, variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gin, exchange of the basic residues Lys and Arg and replacements among the aromatic residues Phe, Tyr.

Further particularly preferred in this regard are variants, analogs, derivatives and fragments, and variants, analogs and derivatives of the fragments, having the amino acid sequence of the cathepsin K polypeptide of FIG. 2 [SEQ ID NO: 20] or of the gDNA in the deposited clone, in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the cathepsin K. Also especially preferred in this regard are conservative substitutions. Most highly preferred are polypeptides having the amino acid sequence of FIG. 2 [SEQ ID NO: 20] or the deposited clone without substitutions.

The polypeptides and polynucleotides of the present invention are preferably provided in an isolated form, and preferably are purified to homogeneity.

The polypeptides of the present invention include the polypeptide encoded by at least one of the exons of SEQ ID NO: 3, SEQ ID NO: 5, SEQ ID NO: 7, SEQ ID NO: 9, SEQ ID NO: 11, SEQ ID NO: 13, SEQ ID NO: 15 or SEQ ID NO: 17, (in particular the mature polypeptide) as well as polypeptides which have at least 70% similarity (preferably at least 70% identity) to the polypeptide encoded by at least one of the exons of SEQ ID NO: SEQ ID NO: 3, SEQ ID NO: 5, SEQ ID NO: 7, SEQ ID NO: 9, SEQ ID NO: 11, SEQ ID NO: 13, SEQ ID NO: 15 or SEQ ID NO: 17 and more preferably at least 90% similarity (more preferably at least 90% identity) to the polypeptide encoded by at least one of the exons of SEQ ID NO: SEQ ID NO: 3, SEQ ID NO: 5, SEQ ID NO: 7, SEQ ID NO: 9, SEQ ID NO: 11, SEQ ID NO: 13, SEQ ID NO: 15 or SEQ ID NO: 17 and still more preferably at least 95% similarity (still more preferably at least 95% identity) to the polypeptide encoded by at least one of the exons of SEQ ID NO: SEQ ID NO: 3, SEQ ID NO: 5, SEQ ID NO: 7, SEQ ID NO: 9, SEQ ID NO: 11, SEQ ID NO: 13, SEQ ID NO: 15 or SEQ ID NO: 17 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

Fragments

Also among preferred embodiments of this aspect of the present invention are polypeptides comprising fragments of cathepsin K, most particularly fragments of the cathepsin K having the amino acids encoded by the exons set out in FIG. 1 [SEQ ID NO: 1], or having the amino acid encoded by the exon sequence of the cathepsin K of the deposited clone, and exon fragments or variants and derivatives of the cathepsin K of FIG. 1 [SEQ ID NO: 1] or of the deposited clone.

In this regard a fragment is a polypeptide having an amino acid sequence that entirely is the same as part but not all of the amino acid sequence of the aforementioned cathepsin K polypeptides and variants or derivatives thereof.

Such fragments may be "free-standing," i.e., not part of or fused to other amino acids or polypeptides, such as, for example, an exon, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a cathepsin K polypeptide of the present comprised within a precursor polypeptide designed for expression in a host and having heterologous pre and pro-polypeptide regions fused to the amino terminus of the cathepsin K fragment and an additional region fused to the carboxyl terminus of the fragment. Therefore, fragments in one aspect of the meaning intended herein, refers to the portion or portions of a fusion polypeptide or fusion protein derived from cathepsin K.

As representative examples of polypeptide fragments of the invention, there may be mentioned those which are encoded by the polynucleotide sequence comprising cathepsin K exon 1, 2, 3, 4, 5, 6, 7 or 8, having the exon or intron 1,2,3,4,5,6 or 7 polynucleotide sequences respectively as set out in FIGS. 1 [SEQ ID NO: 1] and 3 [SEQ ID NO: 2–19], or variants, close homologs, derivatives and analogs thereof, as described above, and polypeptides encoded by polynucleotides which are complementary to such polynucleotides.

In this context about includes the particularly recited range and ranges larger or smaller by several, a few, 5, 4, 3, 2 or 1 amino acid at either extreme or at both extremes. For instance, about 65–90 amino acids in this context means a polypeptide fragment of 65 plus or minus several, a few, 5, 4, 3, 2 or 1 amino acids to 90 plus or minus several a few, 5, 4, 3, 2 or 1 amino acid residues, i.e., ranges as broad as 65 minus several amino acids to 90 plus several amino acids to as narrow as 65 plus several amino acids to 90 minus several amino acids.

Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions. Most highly preferred of all in this regard are fragments encoded by each of the exons of cathepsin K.

Among especially preferred fragments of the invention are truncation mutants of cathepsin K. Truncation mutants include cathepsin K polypeptides having the amino acid sequence encoded by the exons of FIG. 1 [SEQ ID NO: 1], or of the deposited clone, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out about also are preferred embodiments of truncation fragments, which are especially preferred among fragments generally.

Also preferred in this aspect of the invention are fragments characterized by structural or functional attributes of cathepsin K. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of cathepsin K.

Certain preferred regions include Garnier-Robson alpha-regions, beta-regions, turn-regions and coil-regions, Chou-Fasman alpha-regions, beta-regions and turn-regions, Kyte-Doolittle hydrophilic regions and hydrophilic regions, Eisenberg alpha and beta amphipathic regions, Karplus-Schulz flexible regions, Emini surface-forming regions and Jameson-Wolf high antigenic index regions.

Among highly preferred fragments in this regard are those that comprise regions of cathepsin K that combine several structural features, such as several of the features set out above. In this regard, the exon sequences of FIG. 1 [SEQ ID NO: 1], which all are characterized by encoding amino acid compositions highly characteristic of turn-regions, hydrophilic regions, flexible-regions, surface-forming regions, and high antigenic index-regions, are especially highly preferred regions. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of cathepsin K. Most highly preferred in this regard are fragments that have a chemical, biological, antigenic or other activity of cathepsin K, including those with a similar activity or an improved activity, or with a decreased undesirable activity.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspondent to the preferred fragments, as discussed above.

Other preferred polynucleotides are genetic elements of cathepsin K, including, but not being limited to, a polyadenylation region, enhancers, a promoter, a cap site introns, exons, and splice sites (references describing these elements include, Damel, J. et al. *Molecular Cell Biology*, second edition, W. H. Freeman, New York (1990); Watson, J. D., et al. *Molecular Biology of the Gene*, Benjamin/Cummings Pub., Menlo Park, Calif., (1987)).

Untranslated regions contain many elements important in regulating gene expression. Mutations and markers in these regions have also been associated with disease (Ozawa T, et al., European Journal of Immunogenetics, APR 1995, 22 (2), 163–169). A preferred embodiment of the invention is the 5' UTR, particularly the sequence set forth in FIG. 3(A) [SEQUENCE ID NO: 2]. Mutations and markers in the 5' UTR have been associated with disease (Carlock L, et al., Human Genetics, APR 1994, 93 (4), 457–459). A particularly preferred polynucleotide is an enhancer and promoter in the 5' UTR region of the cathepsin K gDNA. Enhancers are often found in the 5' UTR and upregulate gene expression (see Miller et al., Biotechniques 7:980–990 (1989) for a general reference on promoters). The enhancer of the present invention can be operatively fused to heterologous genes to upregulate gene expression. It is believed that the enhancer promoter will regulate tissue-specific gene expression, being particularly useful to express genes is osteoclast and leukocytes, particularly macrophages cells. A particularly preferred polynucleotide is the enhancer promoter having the sequence set forth in FIG. 3(A) [SEQUENCE ID NO: 2]. Transcription factors are often associated with the enhancer and promoter and act to modulate the function of these regions and binding sites for these factors have been described (Faisst, Steffen and Meyer, Silke, Nucleic Acids Research, Vol. 20, No. 1, pp. 3–26, 1991; Smale, Stephen T., Transcription:Mechanisms and Regulation, Raven Press, Ltd. pp. 63–81 (1994)). These sites bind such factors as, for example, Sp1, Ap1, and Ap3 which are involved in transcription initiation (Faisst, Steffen and Meyer, Silke, Nucleic Acids Research, Vol. 20, No. 1, pp. 3–26, 1991). Preferred canonical binding sites for transcription factors are underlined in FIG. 3(S) [SEQUENCE ID NO: 2]. The Pu Box in FIG. 3(S) [SEQUENCE ID NO: 2] has been described to be present in a macrophage gene, a cell in which cathepsin K is also found (Zhang, Dong-Er, Mol. and Cell. Biol., Vol. 14, No. 1, pp. 373–381 (1994)). The present invention provides a promoter region that is useful, among other things, for the mediation of tissue-specific expression in osteoclasts and leukocytes, particularly macrophages. A Pu box (AGGAA), present in the enhancer and promoter region has also been observed in a macrophage cell line (THP1). Pu boxes in the sequences in the invention are provided. These Pu boxes are believed to be active in the cathepsin K gene in macrophages. RT-PCR performed in THP1 cells, using cathepsin K sequence as a probe, showed expression. The promoter is particularly useful for the study of the control of cathepsin K gene expression, particularly as a region to be probed to diagnose disease. Vitamin D response elements have been found in the 5' UTR of known genes (Kahlen, Jean-Pierre and Carlberg, Carsten, Biochemical & Biophysical Research Communications, Vol. 202, No. 3, pp. 1366–1372 (1994); Darwish, Hisham and DeLuca, Hector, Critical Reviews in Eukaryotic Gene Expression, 3(2):89–116 (1993); Carlberg, Carsten, Eur. J. Biochem. 231, pp. 517–527 (1995); Ohyama, Yoshihiko, J. Biol. Chem., Vol. 269, No. 14, pp. 10545–10550 (1994)). Portions of vitamin D ("vD half sites") responsive elements and calcium ion responsive elements ("Ca half pairs") are present in the 3' UTR sequence as set forth in FIG. 3(S) [SEQUENCE ID NO: 2]. Such sites have been described (Katz, Ronald, W., Subauste, Jose, S., and Koenig, Ronald J., J. Biol. Chem., Vol. 270, No. 10, pp. 5238–5242 (1995)). Other half sites present in the sequence of the 5' UTR set forth in FIG. 3(A and S) [SEQUENCE ID NO: 2] include osteopontin/parathyroid hormone responsive element, calcitrol response element and osteocalcin half site (see, for example, Juge-Aubry, Cristiana, et al., J. Biol. Chem., Vol. 270, No. 30, pp. 18117–18122 (1995)). Promoter factor binding sites found in the promoter and enhancer region and provided in the invention are also found in cathepsin K introns. Estrogen response elements are also expected to be present in cathepsin K 5' UTR. Skilled artisans can readily find such elements using the methods provided herein.

A further preferred polynucleotide is a cap site located 49 base pairs upstream of the ATG start codon of the sequence set forth in (FIG. 2).

A further preferred embodiment of the invention is the promoter region of cathepsin K (FIG. 3(A) and (S) [SEQUENCE ID NO: 2]). Functional promoter region sequences have been described (Corden, J., et al., Science, 209, pp. 1406–1414 (1990)). A non-canonical promoter region in the sequence of cathepsin K set forth in FIGS. 3(A) [SEQUENCE ID NO: 2] and (S) [SEQUENCE ID NO: 2] comprises an A-T rich stretch at 19–27 base pairs upstream of the start codon ATG. Mutations in the TATA box region of promoters have been shown to be associated with disease (Peltoketo H, et al., Genomics, 1994, 23 (1), 250–252).

The 3' untranslated region of cathepsin K is a preferred polynucleotide of the invention, especially that polynucleotide set forth in FIG. 3(Q) [SEQUENCE ID NO: 18], especially that region set forth in FIG. 3(R) [SEQUENCE ID NO: 19]. Mutations in the 3' UTR have been associated with disease (Saito A, et al., Journal of the American Society of Nephrology, 1994, 4 (9), 1649–1653; Payne SJ, et al., Human Molecular Genetics, 1994, 3 (2), 390). The polyadenylation region set forth in FIG. 3(Q) [SEQUENCE ID NO: 18] is also a preferred polynucleotide of the 3' UTR. The polyadenylation region comprises two copies of the canonical polyadenylation hexanucleotide, AATAAA. The polyadenylation region can be used, for example, in expression vectors to mediate mRNA 3' end formation (see, for example Gil, A. et al., *Nature* 312:473–474 (London) (1984)).

Other particularly preferred polynucleotides of the invention are the splice sites, including, but not limited to the splice donors, splice acceptors and the splice branchpoint. Splice junctions formation is essential for the proper creation of an open reading frame (Mount, Stephen, M., Department of Molecular Biophysics and Biochemistry, Yale University, Sterling Hall of Medicine, New Haven, Conn., USA, IRL Press Limited, London, pp. 459–472 (1981)). Diseases associated with the improper formation of the splice junction are known. Particularly preferred splice junction polynucleotides are set forth in FIG. 4.

Introns comprise elements important in gene expression and in the formation of mature mRNA. Mutations and markers in introns have been shown to be associated with diseases (Peral, G. et al., Human Molecular Genetics, APR 1995, 4 (4), 569–574; Chrysogelos, S.A., Nucleic Acids Research, 1993, 21 (24), 5736–5741; Ameis, D., Journal of Lipid Research, 1995, 36 (2), 241–250). The splice junctions have also been shown to be associated with disease (Ameis D, et al., Journal of Lipid Research, FEB 1995, 36 (2), 241–250; Petrini JHJ, et al., Journal of Immunology, 1994, 152 (1), 176–183; Kleiman FE, et al., Human Genetics, 1994, 94 (3), 279–282). Alternative splicing and cryptic splice sites selection also have been shown to be associated with disease (Arakawa H, et al., Human Molecular Genetics, 1994, 3 (4), 565–568; Tieu PT, et al., Human Mutation, 1994, 3 (3), 333–336; Reale MA, et al., Cancer Research, 1994, 54 (16), 4493–4501). Introns may also comprise enhancer elements as part of their sequence.

Preferred embodiments of the invention are the cathepsin K introns, particularly those introns having the sequences set forth in FIG. 3 (C, E, G, I, K, M, and O) [SEQUENCE ID NO: 4, 6, 8, 10, 14, and 16]. Polymorphisms in the introns can serve as markers for disease following linkage analysis. Moreover, genetic analyses described herein can be used to locate mutations in the introns associated with and/or causing disease.

Another preferred embodiment is a cathepsin K intronic enhancer.

Intron 3 does not follow consensus splice junction GT/AG rule. This intron/exon boundaries was verified by sequencing of the P1 clone and the genomic DNA. GC/AG splice junctions though not common, have been described(Mount, Stephen, M., Department of Molecular Biophysics and Biochemistry, Yale University, Sterling Hall of Medicine, New Haven, Conn., USA, IRL Press Limited, London, pp. 459–472 (1981)).

Further preferred embodiments of the invention are the cathepsin K exons, particularly those exons having the sequences set forth in FIG. 3 (B, D, F, H, J, L, N, and P) [SEQUENCE ID NO: 3, 5, 7, 9, 11, 13, 15 and 17 respectively]. Polymorphisms in the exons can serve as markers for disease following linkage analysis. Moreover, genetic analyses described herein can be used to locate mutations in the exons associated with and/or causing disease.

Polynucleotide fragments of the invention can be used to create ribozymes that inhibit the expression of the cathepsin K gene. General methods for the construction of ribozyme constructs are known in the art (Stram Y, and Molad T, Virus Genes, 1995, 9 (2), 155–159). Skilled artisans can readily adapt these methods using the novel fragments of the invention to create novel ribozyme constructs. Preferred ribozyme constructs comprise sequences which are complementary to the transcribed control elements of the cathepsin K gene, particularly polynucleotides that are complementary to the 5' untranslated region, splice junctions, and 3' untranslated region, especially the polyadenylation region.

The fragments of the invention, particularly regions in the untranslated region, the promoter and introns are useful as diagnostic probes for disease, particularly bone disease, such as osteoporosis, and including, for example, Paget's disease, Gaucher's disease, CNS inflammation, Alzheimer's disease, hyperparathyroidism, bone degradation, metastatic tumors, rhemuatoid arthritis, osteoarthritis, periodontal disease and degradation of bone implants and bone protheses, particularly dental implants. Moreover, markers for disease can be located in regions of the cathepsin gene, particularly untranslated regions, which are useful with the diagnostic methods of the invention.

Vectors, Host cells, Expression

The present invention also relates to vectors which include polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate, polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. cited above, which is illustrative of the many laboratory manuals that detail these techniques.

In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsidated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skill, are set forth in great detail in Sambrook et al. cited elsewhere herein.

The DNA sequence in the expression vector is operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. It will be understood that numerous promoters not mentioned are suitable for use in this aspect of the invention are well known and readily may be employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, tetracycline, kanamycin, and ampicillin resistance genes for culturing *E. coli* and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as *E. coli*, streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Hosts for a great variety of expression constructs are well known, and those of skill will be enabled by the present disclosure readily to select a host for expressing a polypeptides in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available. Two such vectors are pKK232-8 and pCM7. Thus, promoters for expression of polynucleotides of the present invention include not only well known and readily available promoters, but also promoters that readily may be obtained by the foregoing technique, using a reporter gene.

A preferred embodiment of the invention are expression vectors comprising cathepsin K promoter sequences that function as a promoter. Such vector constructs may be used for targeted gene expression in cells which utilize the cathepsin K promoter, for example, osteoclasts and macrophages. Any gene of interest can be expressibly linked to the cathepsin K promoter and expressed in such cells which utilize the cathepsin K promoter. In this manner genes which immortalize primary eukaryotic cells, such as, for example, SV40 T-Antigen, may be expressibly linked cathepsin K promoter to immortalize cells, such as, for example, bone cells, including osteoclasts, and macrophages. Certain preferred vectors comprise cathepsin K promoter expressibly linked to a toxin gene, such as for example, ricin, and are useful in methods for the targeted killing of cell populations that utilize the cathepsin K promoter for gene expression. Certain other preferred vectors comprise cathepsin K promoter expressibly linked to a anti-cathepsin K ribozyme or antisense polynucleotide, which are useful in methods for such targeted killing.

Among known bacterial promoters suitable for expression of polynucleotides and polypeptides in accordance with the present invention are the E. coli lacI and lacZ promoters, the T3 and T7 promoters, the gpt promoter, the lambda PR, PL promoters and the trp promoter. Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Selection of appropriate vectors and promoters for expression in a host cell is a well known procedure and the requisite techniques for expression vector construction, introduction of the vector into the host and expression in the host are routine skills in the art.

The present invention also relates to host cells containing the above-described constructs discussed above. The host cell can be a higher eukaryotic cell, such as a mammalian cell or insect cell, or a lower eukaryotic cell, such as a yeast cell, or the host cell can be a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al. BASIC METHODS IN MOLECULAR BIOLOGY, (1986).

Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., MOLECULAR CLONING: A LABORATORY MANUAL, 2nd Ed., Cold Spring Harbor Laboratory Press, Cold Spring Harbor, N.Y. (1989).

Generally, recombinant expression vectors for yeast will include origins of replication, a promoter derived from a highly-expressed gene to direct transcription of a downstream structural sequence, and a selectable marker to permit isolation of vector containing cells after exposure to the vector. Among suitable promoters are those derived from the genes that encode glycolytic enzymes such as 3-phosphoglycerate kinase ("PGK"), a-factor, acid phosphatase, and heat shock proteins, among others. Selectable markers include the ampicillin resistance gene of E. coli and the trpl gene of S. cerevisiae.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, a region may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

Suitable prokaryotic hosts for propagation, maintenance or expression of polynucleotides and polypeptides in accordance with the invention include *Escherichia coli, Bacillus subtilis* and *Salmonella typhimurium*. Various species of Pseudomonas, Streptomyces, and Staphylococcus are suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, where the selected promoter is inducible it is induced by appropriate means (e.g., temperature shift or exposure to chemical inducer) and cells are cultured for an additional period.

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can be employed for expression, as well. Examples of mammalian expression systems include the COS-7 lines of monkey kidney fibroblast, described in Gluzman et al., Cell 23:175 (1981). Other cell lines capable of expressing a compatible vector include for example, the C 127, 3T3, CHO, HeLa, human kidney 293 and BHK cell lines.

Mammalian expression vectors will comprise an origin of replication, a suitable promoter and enhancer, and also any necessary ribosome binding sites, polyadenylation sites, splice donor and acceptor sites, transcriptional termination sequences, and 5' flanking non-transcribed sequences that are necessary for expression. In certain preferred embodiments in this regard DNA sequences derived from the SV40 splice sites, and the SV40 polyadenylation sites are used for required non-transcribed genetic elements of these types.

The cathepsin K polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Further Illustrative Aspects and Preferred Embodiments of the Invention

Cathepsin K polynucleotides and polypeptides may be used in accordance with the present invention for a variety of applications, particularly those that make use of the chemical and biological properties cathepsin K. Among these are applications in the detection and treatment of disease, particularly bone disease, such as osteoporosis, and including, for example, Paget's disease, Gaucher's disease, CNS inflammation, Alzheimer's disease, hyperparathyroidism, bone degradation, metastatic tumors, rhemuatoid arthritis, osteoarthritis, periodontal disease and degradation of bone implants and bone protheses, particularly dental implants. Additional applications relate to diagnosis and to treatment of disorders of cells, tissues and organisms. These aspects of the invention are illustrated further by the following discussion.

Polynucleotide Assays

This invention is also related to the use of the cathepsin K exons, introns, promoters and polynucleotides to detect complementary polynucleotides such as, for example, as a diagnostic reagent. Detection of a mutated form of cathepsin K associated with a dysfunction will provide a diagnostic tool that can add or define a diagnosis of a disease or susceptibility to a disease which results from under-expression, over-expression or altered expression of cathepsin K, such as, for example, osteoporosis, periodontal disease, Paget's disease, Gaucher's disease, CNS inflammation, Alzheimer's disease, hyperparathyroidism, and bone degradation, metastatic tumors, and degradation of bone implants and bone protheses, particularly dental implants.

Individuals carrying mutations in the human cathepsin K gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis (Saiki et al., Nature, 324:163–166 (1986)). Ligation-mediated amplification may also be used for amplification (Vollach, V., et al., *Nucl. Acids Res*. 22:2507 (1994). RNA or cDNA may also be used in the same ways. As an example, PCR primers complementary to the nucleic acid encoding cathepsin K can be used to identify and analyze cathepsin K expression and mutations. For example, deletions and insertions can be detected by a change in size of the amplified product in comparison to the normal genotype. Point mutations can be identified by hybridizing amplified DNA to radiolabeled cathepsin K RNA or alternatively, radiolabeled cathepsin K antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations also may be revealed by nuclease protection assays, such as RNase and S1 protection or the chemical cleavage method (e.g., Cotton et al., Proc. Natl. Acad. Sci., USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP"), SSCP and Southern blotting of genomic DNA.

In addition to more conventional gel-electrophoresis and DNA sequencing, mutations also can be detected by in situ analysis.

Chromosome Assays

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the gDNA herein disclosed is used to clone genomic DNA of a cathepsin K gene. This can be accomplished using a variety of well known techniques and libraries, which generally are available commercially. The genomic DNA then is used for in situ chromosome mapping using well known techniques for this purpose. Typically, in accordance with routine procedures for chromosome mapping, some trial and error may be necessary to identify a genomic probe that gives a good in situ hybridization signal.

In some cases, in addition, sequences can be mapped to chromosomes by preparing PCR primers (preferably 15–25 bp) from the gDNA. Computer analysis of the 3' untranslated region of the gene is used to rapidly select primers that do not span more than one exon in the genomic DNA complicate the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes (e.g., radiation hybrid panels) or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with gDNA as short as 50 to as long as 600. For a review of this technique, see Verma et al., HUMAN CHROMOSOMES: A MANUAL OF BASIC TECHNIQUES, Pergamon Press, New York (1988).

Once a sequence has been mapped to a precise chromosomal location, the physical position of the sequence on the chromosome can be correlated with genetic map data. Such data are found, for example, in V. McKusick, MENDELIAN INHERITANCE IN MAN, available on line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a gDNA precisely localized to a chromosomal region associated with the disease could be one of between 50 and 500 potential causative genes (This assumes 1 megabase mapping resolution and one gene per 20 kb).

Polypeptide Assays

The present invention also relates to a diagnostic assays such as quantitative and diagnostic assays for detecting levels of cathepsin K protein in cells, tissues and bodily fluids, including determination of normal and abnormal levels of polypeptide. Bodily fluids useful in the diagnostic methods of the invention include, for example, synovial fluid, cerebrospinal fluid, urine, serum, gingival fluid and lymph. Thus, for instance, a diagnostic assay in accordance with the invention for detecting over-expression of cathepsin K protein compared to normal control tissue samples may be used to detect the presence of disease, for example, osteoporosis, Paget's disease, Gaucher's disease, CNS inflammation, Alzheimer's disease, hyperparathyroidism, bone degradation, metastatic tumors, rhemuatoid arthritis, osteoarthritis, periodontal disease and degradation of bone implants and bone protheses, particularly dental implants. Assay techniques that can be used to determine levels of a protein, such as an immunoassay for cathepsin K protein of the present invention, in a sample derived from a host are well-known to those of skill in the art. Such assay methods include radioimmunoassays, competitive-binding assays, Western Blot analysis and ELISA assays. Among these ELISAs frequently are preferred. An ELISA assay initially comprises preparing an antibody specific to cathepsin K, preferably a monoclonal antibody. In addition a reporter antibody generally is prepared which binds to the monoclonal antibody. The reporter antibody is attached a detectable reagent such as radioactive, fluorescent or enzymatic reagent, in this example horseradish peroxidase enzyme.

To carry out an ELISA a sample is removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any cathepsin K proteins attached to the polystyrene dish. Unbound monoclonal antibody is washed out with buffer. The reporter antibody linked to horseradish peroxidase is placed in the dish resulting in binding of the reporter antibody to any monoclonal antibody bound to cathepsin K. Unattached reporter antibody is then washed out. Reagents for peroxidase activity, including a colorimetric substrate are then added to the dish. Immobilized peroxidase, linked to cathepsin K through the primary and secondary antibodies, produces a colored reaction product. The amount of color developed in a given time period indicates the amount of cathepsin K protein present in the sample. Quantitative results typically are obtained by reference to a standard curve.

A competition assay may be employed wherein antibodies specific to cathepsin K attached to a solid support and labeled cathepsin K and a sample derived from the host are passed over the solid support and the amount of label detected attached to the solid support can be correlated to a quantity of cathepsin K in the sample.

Antibodies

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of a Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous clonal cell line cultures can be used. Examples include the hybridoma technique (Kohler, G. and Milstein, C., Nature 256: 495–497 (1975), the trioma technique, the human B-cell hybridoma technique (Kozbor et al., Immunology Today 4: 72 (1983) and the EBV-hybridoma technique to produce human monoclonal antibodies (Cole et al., pg. 77–96 in MONOCLONAL ANTIBODIES AND CANCER THERAPY, Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express antibodies, including for example, humanized antibodies to immunogenic polypeptide products of this invention.

Thus, among others, such antibodies can be used to detect and treat diseases caused by or associated with mutant cathepsin K or abnormal cathepsin K levels, such as, osteoporosis, periodontal disease, Paget's disease, Gaucher's disease, CNS inflammation, Alzheimer's disease, hyperparathyroidism, bone degradation, metastatic tumors, and degradation of bone implants and bone protheses, particularly dental implants.

Immunization using polynucleotides of the inventions can be carried out using known methods to produce a cathepsin K-specific immune response.

Clinical Genomics

This invention provides methods to determine drug responsiveness of individuals having or suspected of having a cathepsin K gene mutation or cathepsin K gene expression abnormality, and also provides reagents to carry out such methods. Individuals may be grouped by their responsiveness to a given compound, particularly drugs, used to treat diseases caused by or associated with a mutation of cathepsin K gene or cathepsin K gene expression. Such individuals may be further grouped by detecting different gene mutations or gene expression level variants. In this manner specific gene mutations and gene expression variants can be readily associated with a certain degree of responsiveness to a compound by an individual). Methods and reagents provided herein can be used to group compound responsiveness by detecting cathepsin K gene mutations and cathepsin K gene expression variants. Other methods for grouping individuals by compound responsivess are known to skilled artisans and can be adapted to use the polypetides and polynucleotides of the invention.

The invention also provides algorithms useful in conjunction with a device or embodied in a composition matter which are useful for the diagnosis of diseases caused by or associated with cathepsin K or mutants or variants thereof. Preferred algorithms are provided for disease stratification and staging.

Cathepsin K Binding Molecules and Assays

This invention also provides a method for identification of molecules, such as receptor molecules, that bind cathepsin K or fragments of cathepsin K of the invention. Genes encoding proteins that bind cathepsin K, such as receptor proteins, can be identified by numerous methods known to those of skill in the art, for example, ligand panning and FACS sorting. Such methods are described in many laboratory manuals such as, for instance, Coligan et al., Current Protocols in Immunology 1(2): Chapter 5 (1991).

For instance, expression cloning may be employed for this purpose. To this end polyadenylated RNA is prepared from a cell responsive to cathepsin K, a cDNA library is created from this RNA, the library is divided into pools and the pools are transfected individually into cells that are not responsive to cathepsin K. The transfected cells then are exposed to labeled cathepsin K. (Cathepsin K can be labeled by a variety of well-known techniques including standard methods of radio-iodination or inclusion of a recognition site for a site-specific protein kinase.) Following exposure, the cells are fixed and binding of cathepsin K, or a molecule which binds to cathepsin K, is determined. These procedures conveniently are carried out on glass slides.

Pools are identified of cDNA that produced cathepsin K-binding cells. Sub-pools are prepared from these positives, transfected into host cells and screened as described above. Using an iterative sub-pooling and re-screening process, one or more single clones that encode the putative binding molecule or substrate, such as cell matrix, bone matrix or a receptor molecule, and the any of the same can be isolated.

Alternatively a labeled ligand can be photoaffinity linked to a cell extract, such as a membrane or a membrane extract, prepared from cells that express a molecule that it binds, such as a receptor molecule. Cross-linked material is resolved by polyacrylamide gel electrophoresis ("PAGE") and exposed to X-ray film. The labeled complex containing the ligand-receptor can be excised, resolved into peptide fragments, and subjected to protein microsequencing. The amino acid sequence obtained from microsequencing can be used to design unique or degenerate oligonucleotide probes to screen cDNA libraries to identify genes encoding the putative receptor molecule.

Polypeptides of the invention also can be used to assess cathepsin K binding capacity of cathepsin K binding molecules, such as receptor molecules, in cells or in cell-free preparations.

Agonists and Antagonists—Assays and Molecules

The invention also provides a method of screening compounds to identify those which enhance or block the action of cathepsin K in or on cells, such as its interaction with cathepsin K-binding molecules such as receptor and enzymatic substrate molecules. An agonist is a compound which increases the natural biological functions of cathepsin K, while antagonists decrease or eliminate such functions.

For example, a cellular compartment, such as a membrane, vacuole, inclusion or a preparation of any thereof, such as a membrane-preparation, may be prepared from a cell that expresses a molecule that binds cathepsin K, such as a molecule of a signaling or regulatory pathway modulated by cathepsin K. The preparation is incubated with labeled cathepsin K in the absence or the presence of a candidate molecule which may be a cathepsin K agonist or antagonist. The ability of the candidate molecule to bind the binding molecule, such as a substrate, is reflected in decreased binding of the labeled ligand. Molecules which bind gratuitously, i.e., without inducing the effects of cathepsin K on binding the cathepsin K binding molecule, are most likely to be good antagonists. Molecules that bind well and elicit effects that are the same as or closely related to cathepsin K are agonists.

Cathepsin K-like effects of potential agonists and antagonists may by measured, for instance, by determining activity of a second messenger system following interaction of the candidate molecule with a cell or appropriate cell preparation, and comparing the effect with that of cathepsin K or molecules that elicit the same effects as cathepsin K. Second messenger systems that may be useful in this regard include but are not limited to AMP guanylate cyclase, ion channel, phosphoinositide hydrolysis second messenger systems, or compounds which signal the binding of a potential agonists and antagonists to cathepsin K or its substrate.

Another example of an assay for cathepsin K antagonists is a competitive assay that combines cathepsin K and a potential antagonist with enzymatic substrate or substrate analogs under appropriate conditions for a competitive inhibition assay. Cathepsin K can be labeled, such as by radioactivity, such that the number of cathepsin K molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing cathepsin K-induced activities, thereby preventing the action of cathepsin K by excluding cathepsin K from binding.

Potential antagonists include a small molecule which binds to and occupies the binding site of the polypeptide thereby preventing binding to cellular binding molecules, such as receptor molecules, such that normal biological activity is prevented. Examples of small molecules include but are not limited to small organic molecules, peptides or peptide-like molecules.

Other potential antagonists include antisense molecules. Antisense technology can be used to control gene expression through antisense DNA or RNA or through triple-helix formation. Antisense techniques are discussed, for example, in—Okano, J. Neurochem. 56: 560 (1991); OLIGODEOXY-NUCLEOTIDES AS ANTISENSE INHIBITORS OF GENE EXPRESSION, CRC Press, Boca Raton, Fla. (1988). Triple helix formation is discussed in, for instance Lee et al., Nucleic Acids Research 6:3073 (1979); Cooney et al., Science 241: 456 (1988); and Dervan et al., Science 251:1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of cathepsin K. The antisense RNA oligonucleotide hybridizes to the mRNA in vivo and blocks translation of the mRNA molecule into cathepsin K polypeptide. The oligonucleotides described above can also be delivered to cells such that the antisense RNA or DNA may be expressed in vivo to inhibit production of cathepsin K.

The antagonists may be employed in a composition with a pharmaceutically acceptable carrier, e.g., as hereinafter described.

The antagonists may be employed for instance to treat diseases caused by or associated with mutant cathepsin K or abnormal cathepsin K levels, such as, osteoporosis, Paget's disease, Gaucher's disease, CNS inflammation, Alzheimer's disease, hyperparathyroidism, bone degradation, metastatic tumors, rhemuatoid arthritis, osteoarthritis, periodontal disease and degradation of bone implants and bone protheses, particularly dental implants.

Compositions

The invention also relates to compositions comprising the ploynucleotides or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal, intraarticular, or intradermal routes among others.

The pharmaceutical compositions generally are administered in an amount effective for treatment or prophylaxis of a specific indication or indications. In general, the compositions are administered in an amount of at least about 10 mg/kg body weight. Preferably, in most cases, dose is from about 10 mg/kg to about 1 mg/kg body weight, daily. It will be appreciated that optimum dosage will be determined by standard methods for each treatment modality and indication, taking into account the indication, its severity, route of administration, complicating conditions and the like.

Gene Therapy

The cathepsin K polynucleotides, polypeptides, agonists and antagonists that are polypeptides may be employed in accordance with the present invention by expression of such polypeptides in vivo, in treatment modalities often referred to as "gene therapy." Thus, for example, cells from a patient may be engineered with a polynucleotide, such as a DNA or RNA, encoding a polypeptide ex vivo, and the engineered cells then can be provided to a patient to be treated with the polypeptide. For example, cells may be engineered ex vivo by the use of a retroviral plasmid vector containing RNA encoding a polypeptide of the present invention. Such methods are well-known in the art and their use in the present invention will be apparent from the teachings herein.

Cells from a patient may also be engineered with a polynucleotide, such as a ribozyme that has been constructed, using well known methods, to inhibit the gene expression of Cathepsin K. Other constructs may also be engineered into a patient's cells to contains antisense stretches of cathepsin K sequence, using well known methods. Such antisense constructs will inhibit Cathepsin K expression in the patient.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct then may be isolated and introduced into a packaging cell that is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Such vectors well include one or more promoters for expressing the polypeptide. Suitable promoters which may be employed include, but are not limited to, cathepsin K promoter, a retroviral LTR, an SV40 promoter, and the human cytomegalovirus (CMV) promoter described in Miller et al., Biotechniques 7: 980–990 (1989), or any other promoter (e.g., cellular promoters such as eukaryotic cellular promoters including, but not limited to, the histone, RNA polymerase III, and alpha-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the rous sarcoma virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the alpha-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Ψ-2, Ψ-AM, PA12, T19-14X, VT-19-17-H2, YCRE, YCRIP, GP+E-86, GP+envAm12, and DAN cell lines as described in Miller, A., Human Gene Therapy 1:5–14 (1990). The vector may be transduced into the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles then may be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

EXAMPLES

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

Certain terms used herein are explained in the foregoing glossary.

An N used herein in a nucleotide sequence refers to an unknown nucleotide or nucleotides.

All examples were or may be carried out using standard techniques, which are well known and routine to those of skill in the art, except where otherwise described in detail. Routine molecular biology techniques of the following examples can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989), herein referred to as "Sambrook."

All parts or amounts set out in the following examples are by weight, unless otherwise specified.

Unless otherwise stated size separation of fragments in the examples below was carried out using standard techniques of agarose and polyacrylamide gel electrophoresis ("PAGE") in Sambrook and numerous other references such as, for instance, by Goeddel et al., Nucleic Acids Res. 8:4057 (1980).

Unless described otherwise, ligations were accomplished using standard buffers, incubation temperatures and times, approximately equimolar amounts of the DNA fragments to be ligated and approximately 10 units of T4 DNA ligase ("ligase") per 0.5 µg of DNA.

Example 1

Isolation and Sequencing of Human Cathepsin K Genomic Clone cDNA as disclosed in U.S. Pat. No. 5,501,969, was used to isolate the gDNA clone from a gDNA library (Clontech) according to the following method. Primers to adjacent exons (6 of the 7 exons) were prepared. The sequence of these primers is underlined in FIG. 2. PCR was performed using standard methods well known in the art. Amplified fragments were cloned into a TA vector (Clontech) and the clones were sequenced by an automated sequencer (Applied BioSystems Model 373) by established methods well known in the art using forward and reverse sequencing primers. The sequence of all internal introns were obtained. 5' and 3' terminal intron sequences were obtained as follows. 5' end primers were designed to obtain sequence for the first intron (see underlined primer in FIG. 2), using these primers 2 P1 clones were obtained (Genome Systems Inc.). Both clones were full length. PCR was used to confirm the sequence of internal intron-exon boundary junctions (see Example 2). Primers derived from sequence at the 5' end of the P1 clones was used to "walk" and sequence along the clone, in a stepwise fashion, using new primers at each sequence step, by routine methods known in the art. Purification of P1 clones was carried out as set forth in Example 1(d). "Walking" and sequencing was performed in both directions to confirm cathepsin K gDNA sequence. PCR was again performed using proofreading Taq polymerase (PCR Ultima, Perkin Elmer).

A transcription start site was obtained using a 5' RACE kit (Gibco BRL) and the protocol supplied therewith. This site was also confirmed using an RNASe protection assay kit (Hybspeed, RPA Ambion). Example 1 (a)–(d) provide further specifics concerning cloning and sequencing of cathepsin K (a) DNA sequencing of intron-exon boundaries Intron-Exon Boundaries Intron 1

Intron 1 was identified by utilization of 5' RACE (Gibco BRL) technique to determine 5' UTR sequence from which primer could be designed to PCR from exon 1 to exon 2. (intron 1 starts prior to ATG so PCR may not be readily employed based on cDNA sequence available.) Intron 1 was amplified by PCR on human genomic DNA (Clontech) and cloned into PCRII vector and sequenced as described in Example 1.

Intron 2

Intron 2 was identified by PCR on human genomic DNA from primers designed in exon 2 to exon 3. PCR product was cloned and sequenced using standard methods.

Intron 3

Intron 3 was identified by PCR on human genomic DNA from primers designed in exon 3 to exon 4. PCR product was cloned and sequenced using standard methods.

Intron 4

Intron 4 was identified by PCR on human genomic DNA from primers designed in exon 4 to exon 5. PCR product was cloned and sequenced using standard methods.

Introns 5 & 6

Introns 5 and 6 were identified by PCR on human genomic DNA from primers designed in exon 5 to exon 7. PCR product was cloned and sequenced using standard methods confirming presence of both introns.

Intron 7

Intron 7 was identified by PCR on human genomic DNA from primers designed in exon 7 to exon 8. PCR product was cloned and sequenced using standard methods.

All introns that were identified by PCR on human genomic DNA were confirmed by PCR of the same regions on P1 clone A (see (b) below) clone (Genome Systems, Inc.)

(b) DNA sequencing of 5' and 3' untranslated region (UTR)

5' and 3' untranslated regions were isolated from a single P1 clone (Genome Systems Inc.). This P1 clone has been identified herein as "P1 clone A." Sequence was obtained by direct sequence walking up and down the P1 clone with gene specific primers derived from confirmed cDNA sequence using standard methods. These regions were then cloned via PCR and confirmed by sequence analysis using standard methods. The 5' UTR was additionally amplified by PCR using proofreading Taq Polymerase Ultima in accordance with manufacturer instructions and cloned to eliminate sequence ambiguities. 5' and 3' UTR were further confirmed by PCR on human genomic DNA using standard methods.

(c) DNA sequencing of mRNA Cap Site & size of exon 1

An mRNA Cap Site was determined to be about 48 bp upstream of the start codon based on 5' RACE sequencing. Ribonuclease Protection Assay confirmed a protected fragment of about 48 bp in size indicating that the start site from transcription resides about 48 bp upstream of ATG (start codon). Putative transcription factors have been identified by analysis of sequence with database transcription factor sequence information and these are set forth in FIG. 3(S) [SEQUENCE ID NO: 2]. The 1.1 kb 5' UTR fragment was cloned into pCAT expression vectors to further analyze the promoter sequence region.

(d) P1 DNA preparation

P1 clone A colonies were streaked out on Kanamycin LB plates. A single colony was picked and grown O/N in 20 mls with 25 µg/ml of kanamycin. 500 mls of media (25 µg/ml kanamycin) was inoculated with 16 mls of the O/N culture and grown for 10 hours. Cells were pelleted by centrifugation and resuspended in 10 mls of Qiagen P1 Solution. 10 mls of Qiagen P2 Solution was added and incubated at room temp. for 5 min. 10 mls of Qiagen P3 Solution was added and the mixture left on ice for 15 min. The sample was spun at 10,000 g for 15 min. The supernatant was removed and extracted with phenol. The supernatant was then re-extracted with chloroform. The DNA was precipitated following addition of NaOAc pH 5.2 and 1.1 volumes of isopropanol. The DNA was pelleted by centrifugation for 15 min. at 10,000 g and washed with 70% ethanol. To clean up the DNA for sequencing, 250µl of DNA (about 50 µg) was added to 65 µl 30% PEG in 1.5M NaCl. 8.5 µl of 3M NaCl was added and the mixture incubated on ice for 30 min. The sample was spun at 12,000 g for 10 min. The supernatant was discarded and the pellet dissolved in 200 µl distilled water. The DNA was then extracted with chloroform, vortexed and spun at 10,000 g for 1 min. The aqueous layer was removed and the DNA precipitated with 40 µl of NaOAc pH 5.2 and 1 ml of ethanol. The sample was spun at 12,000 g for 30 min. The DNA was washed with 1 ml of 70% ethanol and resuspended on distilled water. Prior to sequencing, the DNA was denatured with 0.1 volumes of 2M NaOH and 2 mM EDTA and incubated at 37° C. for 30 min. The mixture was neutralized with 0.1 volume of 3M NaOAc pH 5.2 and precipitated with 2.5 volumes of ethanol. The denatured DNA was resuspended in distilled water at a concentration of 1 µg/µl 6 µg/µl were used in each sequencing reaction (ABI) using TaqFS.

Example 2

Chromosomal Mapping of Cathepsin K

Purified P1 DNA was used for FISH analysis (Genome Systems, Inc.) to map to specific chromosome. Prior results done showed by use of 2 PCR somatic cell hybrid panels that the gene mapped to Chromosome 1. FISH analysis confirmed mapping to chromosome 1 and also further mapped the gene to 1q21. This is the same locus as is known for cathepsin-S.

Example 3

Expression of Cathepsin K in COS Cells

CAT Assays pCAT-CatK, which contains the 1100 bp putative CatK promoter, upstream of the CAT reporter gene was transfected into COS cells by the DEAE-dextran procedure. Transfections were done on COS cells in 100 mm dishes and 5 µg of DNA was used. As controls, pCAT basic, which contains no promoter or enhancer, and pCAT control, which contains the SV40 promoter and enhancer, were also transferred separately. 72 hours after transfection, extracts were made by freeze-thaw and equal amounts of extract protein were used in both 1-hour and overnight CAT assays. No activity was detected in untransfected COS cells. pCAT-CatK showed a 1.4–1.6 fold increase of CAT expression relative to pCAT basic after subtraction of background from untransfected cells. Since it is possible that higher levels of activation may be obtained in the presence of various inducers, activation of the CatK promoter by adding exogenous 1,25 di-hydroxy vitamin D3 is believed to occur. Vitamin D has been shown by others to activate transcription of osteocalcin, osteopontin, calcitonin and P450 promoters through interaction with the vitamin D receptor and the vitamin D response element(s) found in these various promoters. The ability of vitamin D to transactivate these promoters is believed thought to play a role in the control of bone formation and resorption. Similar experiments can be performed to assess estrogen responsiveness which is also believed thought to play a role in the control of bone formation and resorption.

Example 4

Gene Therapeutic Expression of Human Cathepsin K

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted—the chunks of tissue remain fixed to the bottom of the flask—and fresh media is added (e.g., Ham's F12 media, with 10% FBS, penicillin and streptomycin). The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

A vector for gene therapy is digested with restriction enzymes for cloning a fragment to be expressed. The digested vector is treated with calf intestinal phosphatase to prevent self-ligation. The dephosphorylated, linear vector is fractionated on an agarose gel and purified.

Cathepsin K gDNA capable of expressing active cathepsin K, is isolated. Preferred constructs use the cathepsin K promoter for cell type-specific gene expression. The ends of the fragment are modified, if necessary, for cloning into the vector. For instance, 5' overhanging may be treated with DNA polymerase to create blunt ends. 3' overhanging ends may be removed using S1 nuclease. Linkers may be ligated to blunt ends with T4 DNA ligase.

Equal quantities of the Moloney murine leukemia virus linear backbone and the cathepsin K fragment are mixed together and joined using T4 DNA ligase. The ligation mixture is used to transform *E. Coli* and the bacteria are then plated on agar-containing kanamycin. Kanamycin phenotype and restriction analysis confirm that the vector has the properly inserted gene.

Packaging cells are grown in tissue culture to confluent density in Dulbecco's Modified Eagles Medium (DMEM) with 10% calf serum (CS), penicillin and streptomycin. The vector containing the cathepsin K gene is introduced into the packaging cells by standard techniques. Infectious viral particles containing the cathepsin K gene are collected from the packaging cells, which now are called producer cells.

Fresh media is added to the producer cells, and after an appropriate incubation period media is harvested from the plates of confluent producer cells. The media, containing the infectious viral particles, is filtered through a Millipore filter to remove detached producer cells. The filtered media then is used to infect fibroblast cells. Media is removed from a sub-confluent plate of fibroblasts and quickly replaced with the filtered media. Polybrene (Aldrich) may be included in the media to facilitate transduction. After appropriate incubation, the media is removed and replaced with fresh media. If the titer of virus is high, then virtually all fibroblasts will be infected and no selection is required. If the titer is low, then it is necessary to use a retroviral vector that has a selectable marker, such as neo or his, to select out transduced cells for expansion.

Engineered fibroblasts then may be injected into humans or animals, including for example, rats and mice, either alone or after having been grown to confluence on microcarrier beads, such as cytodex 3 beads. The injected fibroblasts produce cathepsin K product, and the biological actions of the protein are conveyed to the host.

It will be clear that the invention may be practiced otherwise than as particularly described in the foregoing description and examples.

Numerous modifications and variations of the present invention are possible in light of the above teachings and, therefore, are within the scope of the appended claims.

---

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
        ( A ) LENGTH: 13674 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

```
GCTTTGGCTC  CCAAAGGCCT  GGGATTACAG  GCGTGAACCA  CTGCGCCTAG  CCTGTTAGCA      60
GCTCTTAAAA  TCCAGAGGCA  TAAGCCTGTA  TTTTTGAGGG  TTTATGCATG  GAATCCAGCT     120
AGAAACTGAG  TCTATTACAG  ATCCCATTTA  TTATCCTTTC  TATTCCAAGA  AGCCTTTTTT     180
TCTCCTTCCC  CACATCTGTT  TATGGAAGAA  AATGAAGTTT  GGGGTGTGGT  TTGAGGAATC     240
AGCTAGATTC  TTATGATCTG  TCACATGCTT  GGATGTTGGG  GAAGCATTTG  GAGAAGCTCA     300
TGTGACTTGT  CCTAGATTGG  GGATTTTAAT  TGAGACAGAT  GATGTTTATC  GGGCATCCCA     360
CCACCTGAGA  GTTTTAGCAA  CAGAGTCACA  TGTGAGTCCA  TCAGAACTTA  CGGCATTGAT     420
TCAAGTGCTG  TCATAAATAA  CCAGGACTGC  TGTTTTTGGT  TACTTTTAAA  GACAGTTTCA     480
TCTGGACTTT  CTGGGCATAT  CCTCCTTCAG  CAAAACCACA  TTAGGCTGGG  AAAACTATTC     540
TGCCTGGAAG  TAATGACAAC  TTGCAACCAA  CAAGCTTATA  AAAATACAAA  GAATTCTGGA     600
GCCTATGGCT  TCCATTACAT  TATTCTTTTA  TAGCCTTTTA  TGTTCATTAC  CGCATCCCAG     660
AGGTGAGAGT  CAGACACAAA  TATGAAAATA  GGTTTCAATG  TTGGAGAGGT  AAATCCTAAC     720
AGGAAAGGGG  TAGGAAAAGA  TATAATCCCC  CAATATTAAA  ATAAAGATAT  TGAAGAAGAA     780
GGATGGGAGA  GACTAGGGCT  GTGTCCTTCC  TTTTACTCAC  CAAAAGAGAA  AGTAAGCTCC     840
TATTTGAGTC  AATAGATATT  GAGGTCTTGT  TATTTGCCAC  CAAAGACAGT  CTTGTGAGAC     900
TAAATAGCTA  GTAATTCCCT  ACCCTGGCAC  ACATGCTGCA  TACACACAGA  AACACTGCAA     960
ATCCACTGCC  TCCTTCCCTC  CTCCCTACCC  TTCCTTCTCT  CAGCATTTCT  ATCCCGCCT    1020
CCTCCTCTTA  CCCAAATTTT  CCAGCCGATC  ACTGGAGCTG  ACTTCCGCAA  TCCCGATGGA   1080
ATAAATCTAG  CACCCCTGAT  GGTGTGCCCA  CACTTTGCTG  CCGAAACGAA  GCCAGACAAC   1140
AGATTTCCAT  CAGCAGGTAA  CGTTTGCAAC  TTCCTAGATC  TTTTAGCTTT  TCATTCCTGT   1200
CAATTCTCTG  AGTATTAGGG  ATGTAGTGAC  TTGAGGATCA  CAATAAACTT  TTAGCCTCTG   1260
CAGATGAAAA  CAGAGATGCA  CTTCTTAGGT  CATTCCCTGG  CTAAATAAAA  TCTGCCTGGA   1320
```

-continued

```
AATCTGTAGA  ATTCCTTGTA  TGATTTATAT  ATATACATAC  ATGATTGTTA  GTAAAAGCAA   1380
AGTATATAGG  GAATCATTTC  CCCATCCTTC  AAGAGTGGCC  TTTCTGCAGT  GTTTTCTACT   1440
TTGGCCAACA  AGGATCAAAA  CGGTTAACTC  CTTAGTGAGG  AGGAGGAGAG  TGGTATGGGG   1500
AGGTAGTAGC  TCAGTGCTTC  CTGTTCACTG  AGACATCTCA  AAGCCCTTAA  CACTCTAGTT   1560
TTTAAATGTC  CTACTGGACA  TTTTGCCAGT  TTGCAAAATT  ACATGTAAAT  GGACTATAAG   1620
CAATTGTGTA  AGCCATATGT  CATGCTGCAG  GCTGCAAATT  GTTCTTAAAA  TGGAGGATTT   1680
GTAATTAAGA  AAGCCAATGC  AAGAAATGAG  TGAAGCTAAC  TAGAGTAAAC  TTATGAAAAG   1740
CTGTGAATTT  CATCATCATA  GAACATTGCT  TTTCAGTCTG  AACATTCTTC  TAACAAACCT   1800
TGGATCTGAG  GCTTCTTGTC  CTTTGCGGCA  GCCACAGTGG  GTTTTGTTG   TTAGGGGAAA   1860
ATAAAAAACC  TTGCCCGCAG  CATCTGGTTA  AGATTAGGGC  AGTTTCCTGC  CTAAGGAGGG   1920
AAGGGAGAGA  AAAAGGAAGA  AGAAATGCAT  AAGGAGAATG  AGGAGATATA  CAATGTCTCA   1980
GAAAACAGGA  AACATTGTCC  TATTTTCCCT  TGTCCTCTTC  TGACAAGATC  TGGGAAAGTA   2040
CCAGAATTTA  GGCACGAAAG  AGAAGAACGC  CTCGAAGAAA  TGATCAGGAA  GCAAAACTTA   2100
GACGGAAATC  TCTCCTTTGT  GTATTCTGAA  CCCCACTACC  ACCTTGCTAT  TTGTCTGTCT   2160
CCAAGCCTGC  TAGGGACCCT  GGAGGAAACG  CACTGAGCCC  ATTCTGATTG  TCCAGTTTCT   2220
ATCCCCCATT  TCTGGTTGTG  TACGTGTGTG  TGTGTGTGTG  TGTGTGTGTG  TGTGTGTGTG   2280
TGTGTGTGAG  AGAGAGAGAG  ACAGAGAGAG  AAACAGAGAG  AGTGTGTGTT  GCCTAAATCT   2340
CCCGAGAGAG  AGAGAGAGAG  AGAGAGAGAG  AGAGAGAGAG  AGAGAGAGAG  AGAAAAGAGA  GAAATGGCTA   2400
AATCCCCCTA  GATCAAAGTC  CTTGGAACCA  GATGTACCAG  CATCCTATCT  AAACACAGGC   2460
CCCTCCTGAC  TATCATTGTT  TTATCACCCT  TTTTCCGTCT  ACCTTTCTCT  TCCTCATAAA   2520
GCCTAGTTTT  CCTCTGTTTC  CCTGCCAAAT  GGAAGAGTTT  TCCCTAACTA  CATTCTTCTG   2580
CAGGATGTGG  GGGCTCAAGG  TTCTGCTGCT  ACCTGTGGTG  AGCTTGCTC   TGTACCCTGA   2640
GGAGATACTG  GACACCCACT  GGGAGCTATG  GAAGAAGACC  CACAGGAAGC  AATATAACAA   2700
CAAGGTGCCT  GGGGTCCTGG  AGGGGGCATG  GCAGGAAGGC  TGAGACCTGA  GCTCTCTCAT   2760
CTTAGCTTCC  AGACTCCCTT  CTTCAATCCA  AATGCTTTAT  TCCAAGCAAA  TCAGTCCCTC   2820
TTCCCTAACT  CATGTTAACA  TACGGTTTTC  ATTCCTATGC  TTCAATCATC  CTCTTGTCAA   2880
ACTTGTATTC  CTTCCCTTTG  GTTTTATAAG  TGTGTAACAT  TCCTCTTTTG  GGAAGAGTCC   2940
CAAGATTAAT  GCTGTTAATC  CATAAGCAAT  TTTTCTGTCT  CTCCAGAGCT  TGTGTGGTTG   3000
TTTACATATT  ATCTCTCTTC  TTGCAGGCTC  TTAATTCCAT  GGTTAGTTCC  CCAACTAAAC   3060
TGTAAACTTT  TATGATTGTG  AGTTCCTTT   ATTCTCCTAA  AACCCTTCAC  AATATTACAT   3120
ATGAACTGTA  GACAGTCTAT  ACAAGTACTG  ACTATGCTTT  GTTTAGGTGG  ATGAAATCTC   3180
TCGGCGTTTA  ATTTGGGAAA  AAAACCTGAA  GTATATTTCC  ATCCATAACC  TTGAGGCTTC   3240
TCTTGGTGTC  CATACATATG  AACTGGCTAT  GAACCACCTG  GGGGACATGG  CAAGTATAGC   3300
TTCAGCTCCT  GTCCCACCTG  CACCATTTGC  TTTAGTTCCC  TGCTGATGCC  TGGCCTCTTT   3360
CTTCTTTGTC  TTAGACCAGT  GAAGAGGTGG  TTCAGAAGAT  GACTGGACTC  AAAGTACCCC   3420
TGTCTCATTC  CCGCAGTAAT  GACACCCTTT  ATATCCCAGA  ATGGGAAGGT  AGAGCCCCAG   3480
ACTCTGTCGA  CTATCGAAAG  AAAGGATATG  TTACTCCTGT  CAAAAATCAG  GTACTCTCCT   3540
TTCTTCTGGG  TGTGCATATG  TAATCTGGCA  TGACCTTTTC  CTTTTTCTGC  TGCTTTGTTC   3600
TTGAGGTGAA  AGGGCACCAG  GAAAAGAGGG  CAAGGAATTA  AGGTACATCT  CCCCATTCCC   3660
ATTCTGTTAT  TTAACCTCAT  TTGTTTCTGT  ACATTTGGGT  TGTTTCTGGT  TTTTCTTTTT   3720
```

```
CTTTTCCCTT TTTTTTTTTT TTTTTTTTTT GAGATAGAGT CTCACTCTGT CGCCCAGGAT    3780
GGAGTGCAGT GGTGCAATCT TGGCTCACTG CAACCTACAC CTCCCGGGTT CAAGCGATTC    3840
TCCTGCCTCA GCCTCCTGAG TAGCTGAGAT TACAGGCACG CGCCACTACG CCTGGCTAAT    3900
TTTTCTATTT TTATAGAGAT GCGTTTTCAC CATGTTGGCC AGGCTGGTCT TGAACTGACC    3960
TCAGGTGATC CACCTGCCTC AGCCTCCCAA AGTGCTGGGA TTAGAGTCAT GAGCCATCGC    4020
GGCCTGGTTT TTCTTTATTA CAAATAGTGT TGCAATAAGC ACCCTTGTGC ATATGTTTTT    4080
GTGCACATGT ACAAATATTT ATGCAAAATA AGTCCTAAAA TTGGAATTGT TAGGTCACAA    4140
ATAATCCTTT CCCCCCCCCC AAATTTTTTT TTTTTTTTTG AGACAGCGTC TCTGTCACCC    4200
AGGCTGGAGT CCAGTGGCGC AATCATGGCT CACTGCAGCC TCAACGTCTC AGGCTCAAGT    4260
GATTCTCCAA CCTCAGCCTC CCTAGTAGCT GGGAATTAGA AGCACATGCC ACCACACCCA    4320
GCTAATTTTA AAAAATTTTT TGTTAGAGAC AGGGTTTTGC CATGCTACCC AAGCTGGTCT    4380
CAAATTCCTG GGCTCAAGCA ATCTGCCCGC TTCGGCCTCC CAAAGTGCTA GGATTACAGA    4440
CATGAGCCAC CATGCCCAGC CCAAAAAAGT TTTTGCAATC TTACATTCTT ACTAGCATGA    4500
GAATGTCAGT TTTTTCACAA CCCAAACAAC ACAGGATTGT ATCAGCAAGA TAAACAATTG    4560
ATTTAACGTT CATTTAACAA ACACTTTTTG ACCCCCAGAA CCTACCAGAT GCAGTGTTAG    4620
GCAGCAGAGA CTCAAGATGA CTAAGCACACA ACCTGTGTCC TCAGGAAATC TCAATCTAAA   4680
AAAATAGAAC AGGAAAGAAA GAAAAATCTA CAATCTAGCT GCACAAACAA TAATAGCTAA    4740
TACTTTTTGA GATTTTATTG TTTGTCAGGA ACTTCTTAAC TCTTTACATG AGTTTAAATA    4800
TTTAATCCCT TATAACAATA TTTTATGCAT AGAGAAACTG AGACACAGGC AAATTTAGTA    4860
ACTTACCCGG GGTCACATAG CTACTGGGTG GCAAAGTCAG GGTTAGCTCC CAGGACAAAT    4920
GCCTCCACAG CTGGTACTGT GCTCTGCTTT ACTGTAGCTA ATAGTAAAAA TGGTAGCAAA    4980
AATCAATAGC AGTAGAACAG TGCAACAGAT ATTAAGCGGA AGAGGAAGAC TCACAACAAT    5040
GACAACATTT GTGCTGAAAT TTTTAAGAAC ACATGGAATT TCCTTCAGCC GGGTAGAGAG    5100
AAGATATAGA AATGTAAACA CCAAAGATTC ATAGTTTCTC TGTATCCCTT TCAGGGTCAG    5160
TGTGGTTCCT GTTGGGCTTT TAGCTCTGTG GGTGCCCTGG AGGGCCAACT CAAGAAGAAA    5220
ACTGGCAAAC TCTTAAATCT GAGTCCCCAG AACCTAGTGG ATTGTGTGTC TGAGAATGAT    5280
GGCTGTGGAG GGGGCTACAT GACCAATGCC TTCCAATATG TGCAGAAGAA CCGGGGTATT    5340
GACTCTGAAG ATGCCTACCC ATATGTGGGA CAGGTGAGAT TGCTCCACAC AATTATACAG    5400
CTCTGTTGGC TCCTCCTTCC CCAGCATGAT GTTTTGTACT GGAAACAATT CCAGAAATAC    5460
TGTTTTCTGT TATCCTATCC TGCTTTCTTG ATGGAATAAT TCCCACAGA AGGCCAAGAA     5520
GATTTCCACA ATCTGGGGGA ATTTAGGGAG CTTAAGCTAC TATAGCTCCT ATTTGCATCT    5580
CTGCCATGGA GAGAAAACAG AGGCTAGGCT ACCTACCCCA TAGACTTCCG AGCTGGGTTC    5640
TATAACCCTC TGCTCAATTC CTCACTCCCA CAACAAACCC ACAAACCCAC CATGCTATTT    5700
TCACAAATTG TGTGGCTTTA TTTTATATGA TCTCAGTGTG AGTTTTCAGA ACATTTCAGC    5760
AAATTATGTA AGTTTACATG CTAACATCTA TAAAATGAGA GAAAAACAA GTTGCTTCAT     5820
ATAAGAGATA AGGGATTAAC TCAGTTCCTC CTGCATGATC CTCTAGTCAT AGGAAGGAAA    5880
TCATATCTGA AAGGGAGGCA ACCTGAGGGG TTTTTATAC ACATAGGGCT GGGTCTGATA     5940
GACAATATAA TGTAGGGCCT TCACAACAGA AACCTCTGAA ACAGGGACAG CAAGTTTGAG    6000
AATAAAAATG ATGGCTACTG TGTTCTAAGC CGTGTCCTTA GTGCATTTTT TCTTTTTCTT    6060
TTTTTCATTT AATCTCATAA CAACTCTGTT AGGTAGACTT ATCTTGAATG TATAGGTGAG    6120
```

```
GAAATGGACA  CTTAAGGAGA  TAAGACAGTA  TAATTCATAC  CACTAGTATG  TAACAATGTA    6180

AGATGTATCT  ACCAGGGATG  TTTATCTTCT  GCAAACATTC  CTAGGTATAT  CTCCCATGCA    6240

CATGTGCAAG  AATTTCTTAC  TAGGATATAA  TGCCTTGGAA  CTGAATTGTC  TGGGTCTTAG    6300

GGTATGTCTG  TCTTCAACTT  TACTACACAA  TGTCAAATTG  TTTGCCAAAA  TATTTGGAAA    6360

AATTTATACC  TGCAATGTGT  AAGAAATCCC  CTTCAATCAC  CTTTTTATCA  GTATGTTTAT    6420

CTGGCCATTT  GCATTTCTTC  TTCAGTGAAT  TAACTGTTTT  TATCTCTTGC  TCATTTGTTT    6480

TTCTTTTTAT  TTTTTTGAAA  TAGGGTCTTA  CTCTGTTGCC  CAAGGCTGGA  GTGTGGTGAT    6540

ACAGTCATAG  CTCACTGCAG  CCTCCACTTC  CGGGCTCAAG  CAATCCTCTC  GCCTCAGCCT    6600

CCCAAATAGC  TAGGATATAG  GTGCATGCCA  TCATGCCCAC  CAATTTCAAA  AAACCTTTGA    6660

AATTTTTTTT  TTGTAAAAGC  TAGGCATGGT  GGCTCATGCC  TGTAATCCCA  GCACTTTGGG    6720

AGGCTGAGGT  GGGGURCNTN  UDAGGATCGC  TTGAGCCCAG  GAATTGGAGG  TCGGCCTGAT    6780

ACAACATAGC  AAGACCTCAT  CTCTACAGAA  AAAATTTTTA  AAAGTAGCCA  GGTATGATGG    6840

CGTGCATAGT  TCTAGCTACT  CCGGAAGCTG  GTTGGGAGGA  CAACTTGAGC  CTGGGAGTTC    6900

AAGGCTGCTG  TGAACTGTGA  TCATGTCACT  GCTCTAGC    CTGGGTGACA  GAGTGAGACC    6960

CTGTCCCCAA  AAACAACAAC  CGTTTTTTTT  GGTAGAGACA  TTGTCTCGCT  ATGTTGCCAA    7020

GGCTAGTCTC  AAACTCCTGG  GCTCAAGCAA  TCCTCCCACC  TCCCAAAGTG  CTGGGATTAT    7080

AGATGTAAGC  CACCATGCCT  GGCCTACCCT  TTTTTTTTT   TTTTGAAATG  GAAGTTTTGC    7140

TTTTGTCACC  TAGGCTTGAG  TGCAGTGGCG  CGATCTTGGC  TCACTGCAAC  CTCCACCTCC    7200

TGGATTCAAG  CAATTCTCCT  GCCTCAGCCT  CCTGAATAGC  TGGGATTATA  GGCACCCGCA    7260

ACCACGCCCG  GCTAGTTTTT  GTATTTTAG   TACAGACAGG  GTTTCACCAT  GTTGGCCAGC    7320

TGGTCTTGAA  CCCCTGACCT  CAGGTGGTCC  GCCCGCCTCG  GCCTCCCAAA  ATGCTGGGAT    7380

TAAAAGTGTG  AGCCACCATG  CCCCACCCCT  TACTCATTTT  TAATTGGATT  GTTTTTCTC    7440

TTTCTTAGCG  ATTCTTAAAA  GTTTAAAGAG  AATATTTGGA  TACAATACTA  TGTATTTAAA    7500

AGTTGAGGTC  TGTCTTTCCA  TTCTTCTCAC  GATGTCTTTC  AATCTAGAAA  AGTTAATTTT    7560

AATAGGCCTG  GCGCGGTGGC  TCACGCTTGT  AATCCCAGCA  CTTTGGGAGG  CTGAGATGGG    7620

TGGATCACAA  GGTCAGGAGA  TGAAGACCAT  CCTGGCTAAC  ATGGGTGAAA  CCCTGTTTCT    7680

ACTAAAAATA  CAAAAAAATT  AGCTGGGCGT  GGTGGCAGGT  GCCTGTAGTT  CCAGCTACTC    7740

GGGAGGCTGA  GGCAGGAGAA  TGGCGTGAAC  CCGGGAGGTG  GAGCTTGCAG  TGAGCCGAGA    7800

TTGCACCACT  GCACTCCAGC  CTGGGCAACT  GAGCAAGACT  GCGTTTCAAA  AAAAAAAAA    7860

GTTAATTTTA  ATATAGTAAA  ATTAGTAAAA  GGATTAATTT  TCCCTTTGCA  ATTTTTGTAA    7920

TGTGTTTTAT  TCGTTTATGA  ATGGAGAAAG  GTAAGAAAAA  ATAAAATTTA  AAAAGAAGA    7980

GATGTGGCCA  GGTACGGTGG  CTCACACCTA  TAATCCCAGT  AGTTTGGGAG  GCTGAGGCAG    8040

GCAGATCACT  TGAGGTCAGG  AGTTTGAGAC  CAGCTGGGAT  AACATGGTGA  AACCCCATCT    8100

CTACTAAAAA  TACAAAAATT  AGCCAGGTGT  GATTGCGCAC  GCTTGTAATC  CCAGCAGGCT    8160

GAGGCAGGAG  AATTGCTCGA  ACTCAGGAGG  CAGAGGTTGC  AGTGAGCCAA  GATCATGCCA    8220

TTGCACTCCA  GCCTGGGTAA  CAGAGACTCT  GTTTCAAAAA  AATAAAAGA   TAAAAAGGA    8280

AGAGATCTGA  TAGGGCGGCC  AGATAAACAT  TTTAAGGGG   ATGGTATTAT  AAGTTTGTTC    8340

CCAGCATAAT  GCCAGGTTAT  TCTGACTTTA  AAGTATCATC  ACATAATATC  TTTTTGAGTC    8400

AATTTCCAAG  ATATTCTGTT  TCACTTGTAA  TTCTGTGTAA  TTTTTGGCAC  CAGGAGGCAT    8460

CAGGGATTTG  GAGCACATGG  CAGAAACAAA  GGCATCTTGA  AAAATATCAA  GGCAGTAGAC    8520
```

```
CACTGTAATC  TTAAAATGGC  ATATCAAATG  CTGCTATTGC  TGTTAATATT  TAGATAATGT   8580
TAGATAATGT  ATTTTTTTAG  AGGGTATCTC  ACTATCTTGC  ACAGGCTGGA  GTAGAGTGGC   8640
TATTCACAGC  ATGATCACAG  TACACTAAAG  GCTCAAACTC  CTGGGCACAA  ACAATCCTCC   8700
TGCCTCAGCC  TGCTGAGTAG  TAGATAATAA  GTTCTTGTGG  ATGCAACCTT  AGGGTTCTGA   8760
AGGGGTAGTC  TGTAGGAAAA  TGAATTGCTG  AAAAGAATAC  ACCACCTTAA  CATGGGCTAT   8820
TATTCGATTC  CATAATTGTG  GCTTGCCAAT  GAAACATTGC  TAACTACCTG  TAAAATATAG   8880
TGTTGGAAGT  CATAGGCTAA  ATTGCTAAGT  TCTTTAATCT  ATTTTAGTGT  CTTGTTATGT   8940
ACTTTTATAT  TTTGTCTTTG  ATGAGAGCAC  AAGGATCACA  CCAGTTCCCC  TGATATAGGT   9000
GCAGAGGGCC  CAGGTCTTCC  CTCTAGCTAA  GCCTTGGCCT  TGGCCTCCTA  CCCACACAGC   9060
AGCTGGTGCC  TTCCTGCCCC  CTGAGGCTAA  TACATACTAT  GTGGCCAGAA  GATGGTTTAT   9120
GCTTTTTAAA  AAAATCTTAT  TTCAGAAATC  TTTCCCTACT  GTTTTCCTCC  CACATTTATG   9180
TCTTAAAACA  CCTGTAGGGG  ATTTTTTTT   TTTTTTTTT   TTTGAGATGG  AGTCTCGCTC   9240
TCGCCCAGGC  TGGAGTGCAA  TGGCGCGATC  TTGGCTCACT  GCAAGGTCTG  CCTCCCAGGT   9300
TCACGCCATT  CTCCTGCCTC  AGCCTCCCCA  GTAGCTGGGA  CTACAGGCGC  CCGCTACCAC   9360
GCCTGGCTAA  TTTTTTTGCA  TTTTTAGTAG  AGACAGGGTT  TCACTGTTAG  CCAGGATGGT   9420
CTCGATCTCC  TGACCTCGTG  ATCCACCCTC  CTCAGCCTCC  AAAGTGCTGG  GATTAACAGG   9480
CATGGAGCCC  CACCGCACTG  GCCTGTATTT  GTGAGGAAGA  ACAGACCCTC  TTTAGAAGCC   9540
CTAGACTGCT  GCCTCTGTTA  GTTCACTGGC  ATCACTCAAA  ATATTGGTTG  AGTTTCTTAC   9600
TCACTGAGTT  GGTTTTTATG  TGTGGTGGAA  GGCGGGAATC  CTCTTTTCAT  ATTCGTTCTC   9660
ATTGCCTATT  GCTTTGTCCT  AGTCCTATTA  CAATCTTGTT  TCTTCCAGGA  AGAGAGTTGT   9720
ATGTACAACC  CAACAGGCAA  GGCAGCTAAA  TGCAGAGGGT  ACAGAGAGAT  CCCCGAGGGG   9780
AATGAGAAAG  CCCTGAAGAG  GGCAGTGGCC  CGAGTGGGAC  CTGTCTCTGT  GGCCATTGAT   9840
GCAAGCCTGA  CCTCCTTCCA  GTTTTACAGC  AAAGGTAAGA  AGCTGCTGAT  CCTATACAGC   9900
ACTGTCTTTT  ATGATACAAA  CTTGATGGTT  TCTCGAAGGA  CCTTGGGTAT  TTTCAGTACT   9960
TAGTTTTTGT  ATTCACATGG  AGGTGGCCAG  AGAGAAATTA  ACAACTGCTG  CAGTATGGAG  10020
CAGCATCTCT  GTGGTAAACC  CTCCTGACAC  GGATGGAATT  CTTCAAACAG  TCTCCTAGAC  10080
TGGGAGATCC  CACAGGGTGA  CCCTTGGATT  GCATAGAGCC  TCACGCTGGT  AGTTTGTATT  10140
CTAGGTGTGT  ATTATGATGA  AAGCTGCAAT  AGCGATAATC  TGAACCATGC  GGTTTTGGCA  10200
GTGGGATATG  GAATCCAGAA  GGGAAACAAG  CACTGGATAA  TTAAAAACAG  GTAATGATGG  10260
GAACACTACT  TTTGTTATTC  AGTCACCCTT  TTAACACTCA  ACCTCACCTC  CAGCTTCCCG  10320
ATATTCCTTT  CTCTGTCCCA  AATCAAGAAA  AAATTATCTC  AGAGTTCTCA  CTTCTATCTT  10380
CTCAGTCAGA  GGCTCTTAAT  TCTCAGTCTG  ACACTTAATG  GCCAGTGTGT  TAGTCCATTT  10440
TGCATTGCCA  CAAAAGAATA  CCCGAGACTG  GGTAGTTTAT  AAAGAAACGA  GGTTTGTTTG  10500
GCTATACAAA  GCGTGGCACT  AGTATCTGCT  CAGCCTCTGA  TGAGGCCTCA  GAGCTTTTAC  10560
TCATGGCAGA  AGGCAAAAGA  GGGAGCAGGC  ATGTCACATA  GTGAGAGAGG  GAGCAAGAGA  10620
GAGAGGGAGG  TGCCGACTCT  TTAAAGAACC  AGCTCTTGCA  TGAACTAATA  GAGTGAGAAC  10680
TCACTCATCA  CCAAGGCGAT  GGCACCAAGC  CATTCCATGA  GGAATCCACT  CTCATAACCC  10740
AAACACCTCC  CACTATGCCC  CACCTCCCAC  ATTGGGGATC  ACATTTCAGC  ATGAGACTGG  10800
GAGGGGACAC  ACATCCAAAC  CATATCCGCC  AGACAATAGT  GCTCAATTAT  GTGCTGGGCA  10860
GATGCTCCCT  GTGTGCAAGG  TGCTTAGTGA  CATACATAAA  CCAACGAGCA  GATGACACCT  10920
```

```
TCAGTGAGCT  CAGAGCCCAA  TAAGACAGAC  CTAACTAACC  ATGAGATAAA  GCAGTACAAA  10980
GAACCAGCAG  GAGCTTTGGA  ATTACGTATT  TTTACTTTCT  TTTGTCTCTA  ATGTGATCAG  11040
TTTCTTAGAT  GGTTTCCATT  AGCAATCTGT  CTTTAACAGT  AGGGGAGCAG  CGTTAAAGGT  11100
TTAATATTCC  TTTTGAACAG  TTTTTTTCCT  TCAAAATACA  CTTAAGATAC  ACGTATATAA  11160
GAACTTGCCA  AAGATTGTGA  AGAGAAACAT  TTTTTAGAAA  TAAGATATAA  ACAAAAAAAG  11220
TTAGTGTTAC  TTTCCTATGT  TGGGGAACAA  AGAAAACTCC  AGGGTACCTT  GCTTCCCATT  11280
TCTCTTTAGC  ACCTTGTGAC  TTTTGGGGAG  GGGCAGATTG  ATAACAATTA  TAGTTTTCCT  11340
TTCCTGGCTG  ATCACCATTA  ACCTGGCAGC  AGCACTGGCT  AAATCTCCTG  TCCTTAGTGC  11400
CCTCCAAGGA  GCAGGAGCCC  TAGACTCTGG  GTCGCTGACA  GACTCACGCA  GTGGTGTTGT  11460
TCAAACCTGA  AGCAACTTTT  TATATCACAG  TTCCAACTCA  AGGTGAACCT  GAGCATCTTC  11520
CCAAGTCTCC  CACAGCTTCT  GTCCTGTGTT  GTCCCTTCTC  TTGACTCCCA  GGTCCAAGCA  11580
CTTACCCTGT  TCTTTCATGA  TCAGGTACCA  TGTGTGGAGA  TAGCTTCCAA  GAGAGCTGGG  11640
AGGAAGAAAG  GACACACCCG  GGCAGGATCA  GGAACACTGG  GGGCCCCTGG  AGAAGGGGAG  11700
AGTGGGGGAG  GGTACAGGTT  TTAAATAAAA  TGTGTTGGTA  ATTAGAGAAT  GCTGGTTGG   11760
GGAAAGAGGT  CTGAAAACAA  TTCAGGAAGA  TAAACAAGAC  AATCTCTCCT  CTCTCCTCTT  11820
TCTCACGTCG  TCTCTCTTGT  CTTCTAGTCT  CGCTACTCAT  TTCCTTAGTA  ATCTCATCCA  11880
CTCTCATAGT  TTCATCCATC  TCTCCTATGG  GGTTTACCCC  CAAATCAAGA  TCACCAGCTT  11940
CAGCCTCCTT  CTTATGCTCT  AAACTCACAT  TTTCAAGATT  AATATTCCCC  AAATACAGCT  12000
CTGATCATAT  CACTCTCCCA  CTCAAAATCC  CTCACTGGCT  CCTCACGATG  ATGGGTCACA  12060
GAGTAAAGGT  GAAGCTTTTT  AACCTTGCAG  TAAAGGTAAT  TCAACCTGAT  CTCAATCTGC  12120
CTTTCCAGAC  ATCTCTCCCA  CTACACCCTG  TTAGGCACAC  TGCTTTTCAG  CTACATGATC  12180
CTAACAGTGC  CCCACACTTT  CCTGCCTCTG  TTGTTCATTT  CACACCCTTC  CACTGGCATC  12240
CCCTTCCCAC  AGGTCGAAAT  TCTACTTAGC  CTTTTGGCTC  AGCTCAAATG  CCACCTCTTA  12300
CATCAAGCCT  CTAAGATTCT  CTTGATCAGA  AGGAATCTTT  CCCTCCTTTG  ATACCTACAG  12360
TATTATGCCT  TCTCCCTATT  TCTTGACTTT  AAACTCTTTA  AAGTTAAAAA  ACATCATATT  12420
CATTTTTGTG  TACCATCAGT  ACCTCGCACA  ATACTCAGTA  AATATTTTAA  TGAATAAATA  12480
AACTGAGAGT  ACTAAGTATT  TTTCTTGATT  GGTCTTACAG  CTGGGGAGAA  AACTGGGGAA  12540
ACAAAGGATA  TATCCTCATG  GCTCGAAATA  AGAACAACGC  CTGTGGCATT  GCCAACCTGG  12600
CCAGCTTCCC  CAAGATGTGA  CTCCAGCCAG  CCCAAATCCA  TCCTGCTCTT  CCATTTCCTT  12660
CCACGATGGT  GCAGTGTAAC  GATGCACTTT  GGAAGGGAGT  TGGTGTGCTA  TTTTTGAAGC  12720
AGATGTGGTG  ATACTGAGAT  TGTCTGTTCA  GTTTCCCCAT  TTGTTTGTGC  TTCAAATGAT  12780
CCTTCCTACT  TTGCTTCTCT  CCACCCATGA  CCTTTTTCCA  CTGTGGCCAT  CAGGACTTTC  12840
CCCTGACAGC  TGTGTACTCT  TAGGCTAAGA  GATGTGACTA  CAGCCTGCCC  CTGACTGTGT  12900
TGTCCCAGGG  CTGATGCTGT  ACAGGTACAG  GCTGGAGATT  TTCACATAGG  TTAGATTCTC  12960
ATTCACGGGA  CTAGTTAGCT  TTAAGCACCC  TAGAGGACTA  GGGTAATCTG  ACTTCTCACT  13020
TCCTAAGTTC  CCTTCTATAT  CCTCAAGGTA  GAAATGTCTA  TGTTTTCTAC  TCCAATTCAT  13080
AAATCTATTC  ATAAGTCTTT  GGTACAAGTT  TACATGATAA  AAAGAAATGT  GATTTGTCTT  13140
CCCTTCTTTG  CACTTTTGAA  ATAAAGTATT  TATCTCCTGT  CTACAGTTTA  ATAAATAGCA  13200
TCTAGTACAC  ATTCATTTTG  TGTTGGATAC  TGTGTTAGGT  GCTGGAGGAA  AAAAGATGAA  13260
TAGAACATCT  TCTATGTACT  TGATGCGCTC  ACAGTCTGGT  TGTAGAGACT  GTCACATAAA  13320
```

| | | | | | | |
|---|---|---|---|---|---|---|
| CATTTCATCC | CAATTCATTT | ATTTGTTCAT | TCCTTCAGCC | AATATATATT | GAGTTCTTAC | 13380 |
| TCTGTGCCAA | GAACTGTACT | ACATTTCTGG | GATTAAGTGG | ATATAAGGAG | ATCTCAGTGT | 13440 |
| TTAATCTGCC | TGAGGGAGA | CTAAATTAAG | TGACATGGAA | ACTTGGGTCT | TGAAAAACAT | 13500 |
| TTTAAGGTTA | TTTTTTCTTT | TCTCTCTCTC | TCGCTCTGTC | TTTCTCTCTC | TTTCGTCAGG | 13560 |
| GTCTCCCTCT | GTTGCCAGG | CTGGAGTCAG | TGGCACTCAT | AGCTCACTGC | AGCCTTGATC | 13620 |
| TCCTGGGCTC | AAGAGTTCTT | CCCACCTCAG | TCTCCTAAGT | AGCTTGGACT | ACGG | 13674 |

( 2 ) INFORMATION FOR SEQ ID NO:2:

( i ) SEQUENCE CHARACTERISTICS:
        ( A ) LENGTH: 1108 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:2:

| | | | | | | |
|---|---|---|---|---|---|---|
| GCTTTGGCTC | CCAAAGGCCT | GGGATTACAG | GCGTGAACCA | CTGCGCCTAG | CCTGTTAGCA | 60 |
| GCTCTTAAAA | TCCAGAGGCA | TAAGCCTGTA | TTTTTGAGGG | TTTATGCATG | GAATCCAGCT | 120 |
| AGAAACTGAG | TCTATTACAG | ATCCCATTTA | TTATCCTTTC | TATTCCAAGA | AGCCTTTTTT | 180 |
| TCTCCTTCCC | CACATCTGTT | TATGGAAGAA | AATGAAGTTT | GGGGTGTGGT | TTGAGGAATC | 240 |
| AGCTAGATTC | TTATGATCTG | TCACATGCTT | GGATGTTGGG | GAAGCATTTG | GAGAAGCTCA | 300 |
| TGTGACTTGT | CCTAGATTGG | GGATTTTAAT | TGAGACAGAT | GATGTTTATC | GGGCATCCCA | 360 |
| CCACCTGAGA | GTTTTAGCAA | CAGAGTCACA | TGTGAGTCCA | TCAGAACTTA | CGGCATTGAT | 420 |
| TCAAGTGCTG | TCATAAATAA | CCAGGACTGC | TGTTTTTGGT | TACTTTTAAA | GACAGTTTCA | 480 |
| TCTGGACTTT | CTGGGCATAT | CCTCCTTCAG | CAAAACCACA | TTAGGCTGGG | AAAACTATTC | 540 |
| TGCCTGGAAG | TAATGACAAC | TTGCAACCAA | CAAGCTTATA | AAAATACAAA | GAATTCTGGA | 600 |
| GCCTATGGCT | TCCATTACAT | TATTCTTTTA | TAGCCTTTTA | TGTTCATTAC | CGCATCCCAG | 660 |
| AGGTGAGAGT | CAGACACAAA | TATGAAAATA | GGTTTCAATG | TTGGAGAGGT | AAATCCTAAC | 720 |
| AGGAAAGGGG | TAGGAAAAGA | TATAATCCCC | CAATATTAAA | ATAAAGATAT | TGAAGAAGAA | 780 |
| GGATGGGAGA | GACTAGGGCT | GTGTCCTTCC | TTTTACTCAC | CAAAAGAGAA | AGTAAGCTCC | 840 |
| TATTTGAGTC | AATAGATATT | GAGGTCTTGT | TATTTGCCAC | CAAAGACAGT | CTTGTGAGAC | 900 |
| TAAATAGCTA | GTAATTCCCT | ACCCTGGCAC | ACATGCTGCA | TACACACAGA | AACACTGCAA | 960 |
| ATCCACTGCC | TCCTTCCCTC | CTCCCTACCC | TTCCTTCTCT | CAGCATTTCT | ATCCCCGCCT | 1020 |
| CCTCCTCTTA | CCCAAATTTT | CCAGCCGATC | ACTGGAGCTG | ACTTCCGCAA | TCCCGATGGA | 1080 |
| ATAAATCTAG | CACCCCTGAT | GGTGTGCC | | | | 1108 |

( 2 ) INFORMATION FOR SEQ ID NO:3:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:3:

| CACACTTTGC | TGCCGAAACG | AAGCCAGACA | ACAGATTTCC | ATCAGCAG | | 4 8 |
|---|---|---|---|---|---|---|

( 2 ) INFORMATION FOR SEQ ID NO:4:

( i ) SEQUENCE CHARACTERISTICS:
        ( A ) LENGTH: 1427 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:4:

| GTAACGTTTG | CAACTTCCTA | GATCTTTTAG | CTTTTCATTC | CTGTCAATTC | TCTGAGTATT | 6 0 |
|---|---|---|---|---|---|---|
| AGGGATGTAG | TGACTTGAGG | ATCACAATAA | ACTTTTAGCC | TCTGCAGATG | AAAACAGAGA | 1 2 0 |
| TGCACTTCTT | AGGTCATTCC | CTGGCTAAAT | AAAATCTGCC | TGGAAATCTG | TAGAATTCCT | 1 8 0 |
| TGTATGATTT | ATATATATAC | ATACATGATT | GTTAGTAAAA | GCAAAGTATA | TAGGGAATCA | 2 4 0 |
| TTTCCCCATC | CTTCAAGAGT | GGCCTTTCTG | CAGTGTTTTC | TACTTTGGCC | AACAAGGATC | 3 0 0 |
| AAAACGGTTA | ACTCCTTAGT | GAGGAGGAGG | AGAGTGGTAT | GGGGAGGTAG | TAGCTCAGTG | 3 6 0 |
| CTTCCTGTTC | ACTGAGACAT | CTCAAAGCCC | TTAACACTCT | AGTTTTAAA | TGTCCTACTG | 4 2 0 |
| GACATTTGC | CAGTTTGCAA | AATTACATGT | AAATGGACTA | TAAGCAATTG | TGTAAGCCAT | 4 8 0 |
| ATGTCATGCT | GCAGGCTGCA | AATTGTTCTT | AAAATGGAGG | ATTTGTAATT | AAGAAAGCCA | 5 4 0 |
| ATGCAAGAAA | TGAGTGAAGC | TAACTAGAGT | AAACTTATGA | AAAGCTGTGA | ATTTCATCAT | 6 0 0 |
| CATAGAACAT | TGCTTTTCAG | TCTGAACATT | CTTCTAACAA | ACCTTGGATC | TGAGGCTTCT | 6 6 0 |
| TGTCCTTTGC | GGCAGCCACA | GTGGGTTTTT | GTTGTTAGGG | GAAAATAAAA | AACCTTGCCC | 7 2 0 |
| GCAGCATCTG | GTTAAGATTA | GGGCAGTTTC | CTGCCTAAGG | AGGGAAGGGA | GAGAAAAGG | 7 8 0 |
| AAGAAGAAAT | GCATAAGGAG | AATGAGGAGA | TATACAATGT | CTCAGAAAAC | AGGAAACATT | 8 4 0 |
| GTCCTATTTT | CCCTTGTCCT | CTTCTGACAA | GATCTGGGAA | AGTACCAGAA | TTTAGGCACG | 9 0 0 |
| AAAGAGAAGA | ACGCCTCGAA | GAAATGATCA | GGAAGCAAAA | CTTAGACGGA | AATCTCTCCT | 9 6 0 |
| TTGTGTATTC | TGAACCCCAC | TACCACCTTG | CTATTTGTCT | GTCTCCAAGC | CTGCTAGGGA | 1 0 2 0 |
| CCCTGGAGGA | AACGCACTGA | GCCCATTCTG | ATTGTCCAGT | TTCTATCCCC | CATTTCTGGT | 1 0 8 0 |
| TGTGTACGTG | TGTGTGTGTG | TGTGTGTGTG | TGTGTGTGTG | TGTGTGTGTG | TGAGAGAGAG | 1 1 4 0 |
| AGAGACAGAG | AGAGAAACAG | AGAGAGTGTG | TGTTGCCTAA | ATCTCCCGAG | AGAGAGAG | 1 2 0 0 |
| AGAGAGAG | AGAGAGAGAG | AGAGAGAAAA | GAGAGAAATG | GCTAAATCCC | CCTAGATCAA | 1 2 6 0 |
| AGTCCTTGGA | ACCAGATGTA | CCAGCATCCT | ATCTAAACAC | AGGCCCCTCC | TGACTATCAT | 1 3 2 0 |
| TGTTTTATCA | CCCTTTTTCC | GTCTACCTTT | CTCTTCCTCA | TAAAGCCTAG | TTTTCCTCTG | 1 3 8 0 |

TTTCCCTGCC AAATGGAAGA GTTTTCCCTA ACTACATTCT TCTGCAG        1427

( 2 ) INFORMATION FOR SEQ ID NO:5:

( i ) SEQUENCE CHARACTERISTICS:
        ( A ) LENGTH: 121 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:5:

GATGTGGGGG CTCAAGGTTC TGCTGCTACC TGTGGTGAGC TTTGCTCTGT ACCCTGAGGA        60
GATACTGGAC ACCCACTGGG AGCTATGGAA GAAGACCCAC AGGAAGCAAT ATAACAACAA        120
G        121

( 2 ) INFORMATION FOR SEQ ID NO:6:

( i ) SEQUENCE CHARACTERISTICS:
        ( A ) LENGTH: 462 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:6:

GTGCCTGGGG TCCTGGAGGG GGCATGGCAG GAAGGCTGAG ACCTGAGCTC TCTCATCTTA        60
GCTTCCAGAC TCCCTTCTTC AATCCAAATG CTTTATTCCA AGCAAATCAG TCCCTCTTCC        120
CTAACTCATG TTAACATACG GTTTTCATTC CTATGCTTCA ATCATCCTCT TGTCAAACTT        180
GTATTCCTTC CCTTTGGTTT TATAAGTGTG TAACATTCCT CTTTTGGGAA GAGTCCCAAG        240
ATTAATGCTG TTAATCCATA AGCAATTTTT CTGTCTCTCC AGAGCTTGTG TGGTTGTTTA        300
CATATTATCT CTCTTCTTGC AGGCTCTTAA TTCCATGGTT AGTTCCCCAA CTAAACTGTA        360
AACTTTTATG ATTGTGAGTT TCCTTTATTC TCCTAAAACC CTTCACAATA TTACATATGA        420
ACTGTAGACA GTCTATACAA GTACTGACTA TGCTTTGTTT AG        462

( 2 ) INFORMATION FOR SEQ ID NO:7:

( i ) SEQUENCE CHARACTERISTICS:
        ( A ) LENGTH: 123 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:7:

| | | | | | |
|---|---|---|---|---|---|
| GTGGATGAAA | TCTCTCGGCG | TTTAATTTGG | GAAAAAAACC | TGAAGTATAT | TTCCATCCAT | 60 |
| AACCTTGAGG | CTTCTCTTGG | TGTCCATACA | TATGAACTGG | CTATGAACCA | CCTGGGGGAC | 120 |
| ATG | | | | | | 123 |

( 2 ) INFORMATION FOR SEQ ID NO:8:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:8:

| | | | | | |
|---|---|---|---|---|---|
| GCAAGTATAG | CTTCAGCTCC | TGTCCCACCT | GCACCATTTG | CTTTAGTTCC | CTGCTGATGC | 60 |
| CTGGCCTCTT | TCTTCTTTGT | CTTAG | | | | 85 |

( 2 ) INFORMATION FOR SEQ ID NO:9:

( i ) SEQUENCE CHARACTERISTICS:
        ( A ) LENGTH: 156 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:9:

| | | | | | |
|---|---|---|---|---|---|
| ACCAGTGAAG | AGGTGGTTCA | GAAGATGACT | GGACTCAAAG | TACCCCTGTC | TCATTCCCGC | 60 |
| AGTAATGACA | CCCTTTATAT | CCCAGAATGG | GAAGGTAGAG | CCCCAGACTC | TGTCGACTAT | 120 |
| CGAAAGAAAG | GATATGTTAC | TCCTGTCAAA | AATCAG | | | 156 |

( 2 ) INFORMATION FOR SEQ ID NO:10:

( i ) SEQUENCE CHARACTERISTICS:
        ( A ) LENGTH: 1624 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO (v) FRAGMENT TYPE:

(vi) ORIGINAL SOURCE:

(xi) SEQUENCE DESCRIPTION: SEQ ID NO:10:

```
GTACTCTCCT TTCTTCTGGG TGTGCATATG TAATCTGGCA TGACCTTTTC CTTTTTCTGC      60
TGCTTTGTTC TTGAGGTGAA AGGGCACCAG GAAAAGAGGG CAAGGAATTA AGGTACATCT     120
CCCCATTCCC ATTCTGTTAT TTAACCTCAT TTGTTTCTGT ACATTGGGT TGTTTCTGGT      180
TTTTCTTTTT CTTTTCCCTT TTTTTTTTT TTTTTTTTT GAGATAGAGT CTCACTCTGT       240
CGCCCAGGAT GGAGTGCAGT GGTGCAATCT TGGCTCACTG CAACCTACAC CTCCCGGGTT     300
CAAGCGATTC TCCTGCCTCA GCCTCCTGAG TAGCTGAGAT TACAGGCACG CGCCACTACG     360
CCTGGCTAAT TTTTCTATTT TTATAGAGAT GCGTTTTCAC CATGTTGGCC AGGCTGGTCT     420
TGAACTGACC TCAGGTGATC CACCTGCCTC AGCCTCCAA AGTGCTGGGA TTAGAGTCAT      480
GAGCCATCGC GGCCTGGTTT TTCTTTATTA CAAATAGTGT TGCAATAAGC ACCCTTGTGC     540
ATATGTTTTT GTGCACATGT ACAAATATTT ATGCAAAATA AGTCCTAAAA TTGGAATTGT     600
TAGGTCACAA ATAATCCTTT CCCCCCCCCC AAATTTTTT TTTTTTTTG AGACAGCGTC       660
TCTGTCACCC AGGCTGGAGT CCAGTGGCGC AATCATGGCT CACTGCAGCC TCAACGTCTC     720
AGGCTCAAGT GATTCTCCAA CCTCAGCCTC CTAGTAGCT GGGAATTAGA AGCACATGCC      780
ACCACACCCA GCTAATTTTA AAAATTTTT TGTTAGAGAC AGGGTTTTGC CATGCTACCC      840
AAGCTGGTCT CAAATTCCTG GGCTCAAGCA ATCTGCCCGC TTCGGCCTCC CAAAGTGCTA     900
GGATTACAGA CATGAGCCAC CATGCCCAGC CCAAAAAAGT TTTTGCAATC TTACATTCTT     960
ACTAGCATGA GAATGTCAGT TTTTTCACAA CCCAAACAAC ACAGGATTGT ATCAGCAAGA    1020
TAAACAATTG ATTTAACGTT CATTTAACAA ACACTTTTTG ACCCCAGAA CCTACCAGAT     1080
GCAGTGTTAG GCAGCAGAGA CTCAAGATGA CTAAGACACA ACCTGTGTCC TCAGGAAATC    1140
TCAATCTAAA AAAATAGAAC AGGAAAGAAA GAAAAATCTA CAATCTAGCT GCACAAACAA    1200
TAATAGCTAA TACTTTTTGA GATTTTATTG TTTGTCAGGA ACTTCTTAAC TCTTTACATG    1260
AGTTTAAATA TTTAATCCCT TATAACAATA TTTTATGCAT AGAGAAACTG AGACACAGGC    1320
AAATTTAGTA ACTTACCCGG GGTCACATAG CTACTGGGTG GCAAAGTCAG GGTTAGCTCC    1380
CAGGACAAAT GCCTCCACAG CTGGTACTGT GCTCTGCTTT ACTGTAGCTA ATAGTAAAAA    1440
TGGTAGCAAA AATCAATAGC AGTAGAACAG TGCAACAGAT ATTAAGCGGA AGAGGAAGAC    1500
TCACAACAAT GACAACATTT GTGCTGAAAT TTTTAAGAAC ACATGGAATT TCCTTCAGCC    1560
GGGTAGAGAG AAGATATAGA AATGTAAACA CCAAAGATTC ATAGTTTCTC TGTATCCCTT    1620
TCAG                                                                 1624
```

(2) INFORMATION FOR SEQ ID NO:11:

(i) SEQUENCE CHARACTERISTICS:
        (A) LENGTH: 219 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

( v i ) ORIGINAL SOURCE:

( x i ) SEQUENCE DESCRIPTION: SEQ ID NO:11:

| GGTCAGTGTG | GTTCCTGTTG | GGCTTTTAGC | TCTGTGGGTG | CCCTGGAGGG | CCAACTCAAG | 60 |
| AAGAAAACTG | GCAAACTCTT | AAATCTGAGT | CCCCAGAACC | TAGTGGATTG | TGTGTCTGAG | 120 |
| AATGATGGCT | GTGGAGGGGG | CTACATGACC | AATGCCTTCC | AATATGTGCA | GAAGAACCGG | 180 |
| GGTATTGACT | CTGAAGATGC | CTACCCATAT | GTGGGACAG | | | 219 |

( 2 ) INFORMATION FOR SEQ ID NO:12:

( i ) SEQUENCE CHARACTERISTICS:
( A ) LENGTH: 4326 base pairs
( B ) TYPE: nucleic acid
( C ) STRANDEDNESS: single
( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:12:

| GTGAGATTGC | TCCACACAAT | TATACAGCTC | TGTTGGCTCC | TCCTTCCCCA | GCATGATGTT | 60 |
| TTGTACTGGA | AACAATTCCA | GAAATACTGT | TTTCTGTTAT | CCTATCCTGC | TTTCTTGATG | 120 |
| GAATAATTTC | CCACAGAAGG | CCAAGAAGAT | TTCCACAATC | TGGGGAATT | TAGGGAGCTT | 180 |
| AAGCTACTAT | AGCTCCTATT | TGCATCTCTG | CCATGGAGAG | AAAACAGAGG | CTAGGCTACC | 240 |
| TACCCCATAG | ACTTCCGAGC | TGGGTTCTAT | AACCCTCTGC | TCAATTCCTC | ACTCCCACAA | 300 |
| CAAACCCACA | AACCCACCAT | GCTATTTTCA | CAAATTGTGT | GGCTTTATTT | TATATGATCT | 360 |
| CAGTGTGAGT | TTTCAGAACA | TTTCAGCAAA | TTATGTAAGT | TTACATGCTA | ACATCTATAA | 420 |
| AATGAGAGAA | AAAACAAGTT | GCTTCATATA | AGAGATAAGG | GATTAACTCA | GTTCCTCCTG | 480 |
| CATGATCCTC | TAGTCATAGG | AAGGAAATCA | TATCTGAAAG | GGAGGCAACC | TGAGGGGTTT | 540 |
| TTTATACACA | TAGGGCTGGG | TCTGATAGAC | AATATAATGT | AGGGCTTCA | CAACAGAAAC | 600 |
| CTCTGAAACA | GGGACAGCAA | GTTTGAGAAT | AAAAATGATG | GCTACTGTGT | TCTAAGCCGT | 660 |
| GTCCTTAGTG | CATTTTTTCT | TTTTCTTTTT | TTCATTTAAT | CTCATAACAA | CTCTGTTAGG | 720 |
| TAGACTTATC | TTGAATGTAT | AGGTGAGGAA | ATGGACACTT | AAGGAGATAA | GACAGTATAA | 780 |
| TTCATACCAC | TAGTATGTAA | CAATGTAAGA | TGTATCTACC | AGGGATGTTT | ATCTTCTGCA | 840 |
| AACATTCCTA | GGTATATCTC | CCATGCACAT | GTGCAAGAAT | TTCTTACTAG | GATATAATGC | 900 |
| CTTGGAACTG | AATTGTCTGG | GTCTTAGGGT | ATGTCTGTCT | TCAACTTTAC | TACACAATGT | 960 |
| CAAATTGTTT | GCCAAAATAT | TTGGAAAAAT | TTATACCTGC | AATGTGTAAG | AAATCCCCTT | 1020 |
| CAATCACCTT | TTTATCAGTA | TGTTTATCTG | GCCATTTGCA | TTTCTTCTTC | AGTGAATTAA | 1080 |
| CTGTTTTTAT | CTCTTGCTCA | TTTGTTTTTC | TTTTTATTTT | TTTGAAATAG | GGTCTTACTC | 1140 |
| TGTTGCCCAA | GGCTGGAGTG | TGGTGATACA | GTCATAGCTC | ACTGCAGCCT | CCACTTCCGG | 1200 |
| GCTCAAGCAA | TCCTCTCGCC | TCAGCCTCCC | AAATAGCTAG | GATATAGGTG | CATGCCATCA | 1260 |
| TGCCCACCAA | TTTCAAAAAA | CCTTTGAAAT | TTTTTTTTG | TAAAAGCTAG | GCATGGTGGC | 1320 |
| TCATGCCTGT | AATCCCAGCA | CTTTGGGAGG | CTGAGGTGGG | AGGATCGCTT | GAGCCCAGGA | 1380 |
| ATTGGAGGTC | GGCCTGATAC | AACATAGCAA | GACCTCATCT | CTACAGAAAA | AATTTTTAAA | 1440 |

| | | | | | |
|---|---|---|---|---|---|
| AGTAGCCAGG | TATGATGGCG | TGCATAGTTC | TAGCTACTCC | GGAAGCTGGT | TGGGAGGACA | 1500 |
| ACTTGAGCCT | GGGAGTTCAA | GGCTGCTGTG | AACTGTGATC | ATGTCACTGC | TCTCTAGCCT | 1560 |
| GGGTGACAGA | GTGAGACCCT | GTCCCCAAAA | ACAACAACCG | TTTTTTTTGG | TAGAGACATT | 1620 |
| GTCTCGCTAT | GTTGCCAAGG | CTAGTCTCAA | ACTCCTGGGC | TCAAGCAATC | CTCCCACCTC | 1680 |
| CCAAAGTGCT | GGGATTATAG | ATGTAAGCCA | CCATGCCTGG | CCTACCCTTT | TTTTTTTTT | 1740 |
| TTGAAATGGA | AGTTTTGCTT | TTGTCACCTA | GGCTTGAGTG | CAGTGGCGCG | ATCTTGGCTC | 1800 |
| ACTGCAACCT | CCACCTCCTG | GATTCAAGCA | ATTCTCCTGC | CTCAGCCTCC | TGAATAGCTG | 1860 |
| GGATTATAGG | CACCCGCAAC | CACGCCCGGC | TAGTTTTGT | ATTTTAGTA | CAGACAGGGT | 1920 |
| TTCACCATGT | TGGCCAGCTG | GTCTTGAACC | CCTGACCTCA | GGTGGTCCGC | CCGCCTCGGC | 1980 |
| CTCCCAAAAT | GCTGGGATTA | AAAGTGTGAG | CCACCATGCC | CCACCCCTTA | CTCATTTTTA | 2040 |
| ATTGGATTGT | TTTTTCTCTT | TCTTAGCGAT | TCTTAAAAGT | TTAAAGAGAA | TATTTGGATA | 2100 |
| CAATACTATG | TATTTAAAAG | TTGAGGTCTG | TCTTTCCATT | CTTCTCACGA | TGTCTTTCAA | 2160 |
| TCTAGAAAAG | TTAATTTTAA | TAGGCCTGGC | GCGGTGGCTC | ACGCTTGTAA | TCCCAGCACT | 2220 |
| TTGGGAGGCT | GAGATGGGTG | GATCACAAGG | TCAGGAGATG | AAGACCATCC | TGGCTAACAT | 2280 |
| GGGTGAAACC | CTGTTTCTAC | TAAAAATACA | AAAAATTAG | CTGGGCGTGG | TGGCAGGTGC | 2340 |
| CTGTAGTTCC | AGCTACTCGG | GAGGCTGAGG | CAGGAGAATG | GCGTGAACCC | GGGAGGTGGA | 2400 |
| GCTTGCAGTG | AGCCGAGATT | GCACCACTGC | ACTCCAGCCT | GGGCAACTGA | GCAAGACTGC | 2460 |
| GTTTCAAAAA | AAAAAAAAGT | TAATTTTAAT | ATAGTAAAAT | TAGTAAAAGG | ATTAATTTTC | 2520 |
| CCTTTGCAAT | TTTTGTAATG | TGTTTTATTC | GTTTATGAAT | GGAGAAAGGT | AAGAAAAAAT | 2580 |
| AAAATTTAAA | AAAGAAGAGA | TGTGGCCAGG | TACGGTGGCT | CACACCTATA | ATCCCAGTAG | 2640 |
| TTTGGGAGGC | TGAGGCAGGC | AGATCACTTG | AGGTCAGGAG | TTTGAGACCA | GCTGGGATAA | 2700 |
| CATGGTGAAA | CCCCATCTCT | ACTAAAAATA | CAAAAATTAG | CCAGGTGTGA | TTGCGCACGC | 2760 |
| TTGTAATCCC | AGCAGGCTGA | GGCAGGAGAA | TTGCTCGAAC | TCAGGAGGCA | GAGGTTGCAG | 2820 |
| TGAGCCAAGA | TCATGCCATT | GCACTCCAGC | CTGGGTAACA | GAGACTCTGT | TCAAAAAAA | 2880 |
| TAAAAAGATA | AAAAAGGAAG | AGATCTGATA | GGGCGGCCAG | ATAAACATTT | TAAAGGGGAT | 2940 |
| GGTATTATAA | GTTTGTTCCC | AGCATAATGC | CAGGTTATTC | TGACTTTAAA | GTATCATCAC | 3000 |
| ATAATATCTT | TTTGAGTCAA | TTTCCAAGAT | ATTCTGTTTC | ACTTGTAATT | CTGTGTAATT | 3060 |
| TTTGGCACCA | GGAGGCATCA | GGGATTTGGA | GCACATGGCA | GAAACAAAGG | CATCTTGAAA | 3120 |
| AATATCAAGG | CAGTAGACCA | CTGTAATCTT | AAAATGGCAT | ATCAAATGCT | GCTATTGCTG | 3180 |
| TTAATATTTA | GATAATGTTA | GATAATGTAT | TTTTTAGAG | GGTATCTCAC | TATCTTGCAC | 3240 |
| AGGCTGGAGT | AGAGTGGCTA | TTCACAGCAT | GATCACAGTA | CACTAAAGGC | TCAAACTCCT | 3300 |
| GGGCACAAAC | AATCCTCCTG | CCTCAGCCTG | CTGAGTAGTA | GATAATAAGT | TCTTGTGGAT | 3360 |
| GCAACCTTAG | GGTTCTGAAG | GGGTAGTCTG | TAGGAAAATG | AATTGCTGAA | AAGAATACAC | 3420 |
| CACCTTAACA | TGGGCTATTA | TTCGATTCCA | TAATTGTGGC | TTGCCAATGA | AACATTGCTA | 3480 |
| ACTACCTGTA | AAATATAGTG | TTGGAAGTCA | TAGGCTAAAT | TGCTAAGTTC | TTTAATCTAT | 3540 |
| TTTAGTGTCT | TGTTATGTAC | TTTTATATTT | TGTCTTTGAT | GAGAGCACAA | GGATCACACC | 3600 |
| AGTTCCCCTG | ATATAGGTGC | AGAGGGCCCA | GGTCTTCCCT | CTAGCTAAGC | CTTGGCCTTG | 3660 |
| GCCTCCTACC | CACACAGCAG | CTGGTGCCTT | CCTGCCCCCT | GAGGCTAATA | CATACTATGT | 3720 |
| GGCCAGAAGA | TGGTTTATGC | TTTTTAAAAA | AATCTTATTT | CAGAAATCTT | TCCCTACTGT | 3780 |
| TTTCCTCCCA | CATTTATGTC | TTAAAACACC | TGTAGGGGAT | TTTTTTTTTT | TTTTTTTTT | 3840 |

```
TGAGATGGAG  TCTCGCTCTC  GCCCAGGCTG  GAGTGCAATG  GCGCGATCTT  GGCTCACTGC    3 9 0 0

AAGGTCTGCC  TCCCAGGTTC  ACGCCATTCT  CCTGCCTCAG  CCTCCCCAGT  AGCTGGGACT    3 9 6 0

ACAGGCGCCC  GCTACCACGC  CTGGCTAATT  TTTTTGCATT  TTTAGTAGAG  ACAGGGTTTC    4 0 2 0

ACTGTTAGCC  AGGATGGTCT  CGATCTCCTG  ACCTCGTGAT  CCACCCTCCT  CAGCCTCCAA    4 0 8 0

AGTGCTGGGA  TTAACAGGCA  TGGAGCCCCA  CCGCACTGGC  CTGTATTTGT  GAGGAAGAAC    4 1 4 0

AGACCCTCTT  TAGAAGCCCT  AGACTGCTGC  CTCTGTTAGT  TCACTGGCAT  CACTCAAAAT    4 2 0 0

ATTGGTTGAG  TTTCTTACTC  ACTGAGTTGG  TTTTTATGTG  TGGTGGAAGG  CGGGAATCCT    4 2 6 0

CTTTTCATAT  TCGTTCTCAT  TGCCTATTGC  TTTGTCCTAG  TCCTATTACA  ATCTTGTTTC    4 3 2 0

TTCCAG                                                                   4 3 2 6
```

( 2 ) INFORMATION FOR SEQ ID NO:13:

( i ) SEQUENCE CHARACTERISTICS:
          ( A ) LENGTH: 166 base pairs
          ( B ) TYPE: nucleic acid
          ( C ) STRANDEDNESS: single
          ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:13:

```
GAAGAGAGTT  GTATGTACAA  CCCAACAGGC  AAGGCAGCTA  AATGCAGAGG  GTACAGAGAG      6 0

ATCCCCGAGG  GGAATGAGAA  AGCCCTGAAG  AGGGCAGTGG  CCCGAGTGGG  ACCTGTCTCT    1 2 0

GTGGCCATTG  ATGCAAGCCT  GACCTCCTTC  CAGTTTTACA  GCAAAG                   1 6 6
```

( 2 ) INFORMATION FOR SEQ ID NO:14:

( i ) SEQUENCE CHARACTERISTICS:
          ( A ) LENGTH: 270 base pairs
          ( B ) TYPE: nucleic acid
          ( C ) STRANDEDNESS: single
          ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:14:

```
GTAAGAAGCT  GCTGATCCTA  TACAGCACTG  TCTTTTATGA  TACAAACTTG  ATGGTTTCTC      6 0

GAAGGACCTT  GGGTATTTTC  AGTACTTAGT  TTTTGTATTC  ACATGGAGGT  GGCCAGAGAG    1 2 0

AAATTAACAA  CTGCTGCAGT  ATGGAGCAGC  ATCTCTGTGG  TAAACCCTCC  TGACACGGAT    1 8 0

GGAATTCTTC  AAACAGTCTC  CTAGACTGGG  AGATCCCACA  GGGTGACCCT  TGGATTGCAT    2 4 0

AGAGCCTCAC  GCTGGTAGTT  TGTATTCTAG                                       2 7 0
```

( 2 ) INFORMATION FOR SEQ ID NO:15:

( i ) SEQUENCE CHARACTERISTICS:
    ( A ) LENGTH: 106 base pairs
    ( B ) TYPE: nucleic acid
    ( C ) STRANDEDNESS: single
    ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:15:

| GTGTGTATTA | TGATGAAAGC | TGCAATAGCG | ATAATCTGAA | CCATGCGGTT | TTGGCAGTGG | 60 |
| GATATGGAAT | CCAGAAGGGA | AACAAGCACT | GGATAATTAA | AAACAG | | 106 |

( 2 ) INFORMATION FOR SEQ ID NO:16:

( i ) SEQUENCE CHARACTERISTICS:
    ( A ) LENGTH: 2270 base pairs
    ( B ) TYPE: nucleic acid
    ( C ) STRANDEDNESS: single
    ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:16:

| GTAATGATGG | GAACACTACT | TTTGTTATTC | AGTCACCCTT | TTAACACTCA | ACCTCACCTC | 60 |
| CAGCTTCCCG | ATATTCCTTT | CTCTGTCCCA | AATCAAGAAA | AAATTATCTC | AGAGTTCTCA | 120 |
| CTTCTATCTT | CTCAGTCAGA | GGCTCTTAAT | TCTCAGTCTG | ACACTTAATG | GCCAGTGTGT | 180 |
| TAGTCCATTT | TGCATTGCCA | CAAAAGAATA | CCCGAGACTG | GGTAGTTTAT | AAAGAAACGA | 240 |
| GGTTTGTTTG | GCTATACAAA | GCGTGGCACT | AGTATCTGCT | CAGCCTCTGA | TGAGGCCTCA | 300 |
| GAGCTTTTAC | TCATGGCAGA | AGGCAAAAGA | GGGAGCAGGC | ATGTCACATA | GTGAGAGAGG | 360 |
| GAGCAAGAGA | GAGAGGGAGG | TGCCGACTCT | TTAAAGAACC | AGCTCTTGCA | TGAACTAATA | 420 |
| GAGTGAGAAC | TCACTCATCA | CCAAGGCGAT | GGCACCAAGC | CATTCCATGA | GGAATCCACT | 480 |
| CTCATAACCC | AAACACCTCC | CACTATGCCC | CACCTCCCAC | ATTGGGGATC | ACATTTCAGC | 540 |
| ATGAGACTGG | GAGGGACAC | ACATCCAAAC | CATATCCGCC | AGACAATAGT | GCTCAATTAT | 600 |
| GTGCTGGGCA | GATGCTCCCT | GTGTGCAAGG | TGCTTAGTGA | CATACATAAA | CCAACGAGCA | 660 |
| GATGACACCT | TCAGTGAGCT | CAGAGCCCAA | TAAGACAGAC | CTAACTAACC | ATGAGATAAA | 720 |
| GCAGTACAAA | GAACCAGCAG | GAGCTTTGGA | ATTACGTATT | TTTACTTTCT | TTTGTCTCTA | 780 |
| ATGTGATCAG | TTTCTTAGAT | GGTTTCCATT | AGCAATCTGT | CTTTAACAGT | AGGGGAGCAG | 840 |
| CGTTAAAGGT | TTAATATTCC | TTTTGAACAG | TTTTTTTCCT | TCAAAATACA | CTTAAGATAC | 900 |
| ACGTATATAA | GAACTTGCCA | AAGATTGTGA | AGAGAAACAT | TTTTAGAAA | TAAGATATAA | 960 |
| ACAAAAAAAG | TTAGTGTTAC | TTTCCTATGT | TGGGAACAA | AGAAAACTCC | AGGGTACCTT | 1020 |
| GCTTCCCATT | TCTCTTTAGC | ACCTTGTGAC | TTTTGGGGAG | GGGCAGATTG | ATAACAATTA | 1080 |
| TAGTTTTCCT | TTCCTGGCTG | ATCACCATTA | ACCTGGCAGC | AGCACTGGCT | AAATCTCCTG | 1140 |

| TCCTTAGTGC | CCTCCAAGGA | GCAGGAGCCC | TAGACTCTGG | GTCGCTGACA | GACTCACGCA | 1200 |
| GTGGTGTTGT | TCAAACCTGA | AGCAACTTTT | TATATCACAG | TTCCAACTCA | AGGTGAACCT | 1260 |
| GAGCATCTTC | CCAAGTCTCC | CACAGCTTCT | GTCCTGTGTT | GTCCCTTCTC | TTGACTCCCA | 1320 |
| GGTCCAAGCA | CTTACCCTGT | TCTTTCATGA | TCAGGTACCA | TGTGTGGAGA | TAGCTTCCAA | 1380 |
| GAGAGCTGGG | AGGAAGAAAG | GACACACCCG | GGCAGGATCA | GGAACACTGG | GGGCCCCTGG | 1440 |
| AGAAGGGGAG | AGTGGGGGAG | GGTACAGGTT | TTAAATAAAA | TGTGTTGGTA | ATTAGAGAAT | 1500 |
| TGCTGGTTGG | GGAAAGAGGT | CTGAAAACAA | TTCAGGAAGA | TAAACAAGAC | AATCTCTCCT | 1560 |
| CTCTCCTCTT | TCTCACGTCG | TCTCTCTTGT | CTTCTAGTCT | CGCTACTCAT | TTCCTTAGTA | 1620 |
| ATCTCATCCA | CTCTCATAGT | TTCATCCATC | TCTCCTATGG | GGTTTACCCC | CAAATCAAGA | 1680 |
| TCACCAGCTT | CAGCCTCCTT | CTTATGCTCT | AAACTCACAT | TTTCAAGATT | AATATTCCCC | 1740 |
| AAATACAGCT | CTGATCATAT | CACTCTCCCA | CTCAAAATCC | CTCACTGGCT | CCTCACGATG | 1800 |
| ATGGGTCACA | GAGTAAAGGT | GAAGCTTTTT | AACCTTGCAG | TAAAGGTAAT | TCAACCTGAT | 1860 |
| CTCAATCTGC | CTTTCCAGAC | ATCTCTCCCA | CTACACCCTG | TTAGGCACAC | TGCTTTTCAG | 1920 |
| CTACATGATC | CTAACAGTGC | CCCACACTTT | CCTGCCTCTG | TTGTTCATTT | CACACCCTTC | 1980 |
| CACTGGCATC | CCCTTCCCAC | AGGTCGAAAT | TCTACTTAGC | CTTTTGGCTC | AGCTCAAATG | 2040 |
| CCACCTCTTA | CATCAAGCCT | CTAAGATTCT | CTTGATCAGA | AGGAATCTTT | CCCTCCTTTG | 2100 |
| ATACCTACAG | TATTATGCCT | TCTCCCTATT | TCTTGACTTT | AAACTCTTTA | AAGTTAAAAA | 2160 |
| ACATCATATT | CATTTTTGTG | TACCATCAGT | ACCTCGCACA | ATACTCAGTA | AATATTTTAA | 2220 |
| TGAATAAATA | AACTGAGAGT | ACTAAGTATT | TTTCTTGATT | GGTCTTACAG | | 2270 |

( 2 ) INFORMATION FOR SEQ ID NO:17:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:17:

| CTGGGGAGAA | AACTGGGGAA | ACAAAGGATA | TATCCTCATG | GCTCGAAATA | AGAACAACGC | 60 |
| CTGTGGCATT | GCCAACCTGG | CCAGCTTCCC | CAAGATG | | | 97 |

( 2 ) INFORMATION FOR SEQ ID NO:18:

( i ) SEQUENCE CHARACTERISTICS:
        ( A ) LENGTH: 598 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:18:

| | | | | | | |
|---|---|---|---|---|---|---|
| TGACTCCAGC | CAGCCCAAAT | CCATCCTGCT | CTTCCATTTC | CTTCCACGAT | GGTGCAGTGT | 60 |
| AACGATGCAC | TTTGGAAGGG | AGTTGGTGTG | CTATTTTGA | AGCAGATGTG | GTGATACTGA | 120 |
| GATTGTCTGT | TCAGTTTCCC | CATTTGTTTG | TGCTTCAAAT | GATCCTTCCT | ACTTTGCTTC | 180 |
| TCTCCACCCA | TGACCTTTTT | CCACTGTGGC | CATCAGGACT | TTCCCCTGAC | AGCTGTGTAC | 240 |
| TCTTAGGCTA | AGAGATGTGA | CTACAGCCTG | CCCCTGACTG | TGTTGTCCCA | GGGCTGATGC | 300 |
| TGTACAGGTA | CAGGCTGGAG | ATTTTCACAT | AGGTTAGATT | CTCATTCACG | GGACTAGTTA | 360 |
| GCTTTAAGCA | CCCTAGAGGA | CTAGGGTAAT | CTGACTTCTC | ACTTCCTAAG | TTCCCTTCTA | 420 |
| TATCCTCAAG | GTAGAAATGT | CTATGTTTC | TACTCCAATT | CATAAATCTA | TTCATAAGTC | 480 |
| TTTGGTACAA | GTTTACATGA | TAAAAGAAA | TGTGATTTGT | CTTCCCTTCT | TTGCACTTTT | 540 |
| GAAATAAAGT | ATTTATCTCC | TGTCTACAGT | TTAATAAATA | GCATCTAGTA | CACATTCA | 598 |

( 2 ) INFORMATION FOR SEQ ID NO:19:

( i ) SEQUENCE CHARACTERISTICS:
        ( A ) LENGTH: 459 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:19:

| | | | | | | |
|---|---|---|---|---|---|---|
| TTTTGTGTTG | GATACTGTGT | TAGGTGCTGG | AGGAAAAAAG | ATGAATAGAA | CATCTTCTAT | 60 |
| GTACTTCATG | CGCTCACAGT | CTGGTTGTAG | AGACTGTCAC | ATAAACATTT | CATCCCAATT | 120 |
| CATTTATTTG | TTCATTCCTT | CAGCCAATAT | ATATTGAGTT | CTTACTCTGT | GCCAAGAACT | 180 |
| GTACTACATT | TCTGGGATTA | AGTGGATATA | AGGAGATCTC | AGTGTTTAAT | CTGCCTGAGG | 240 |
| GGAGACTAAA | TTAAGTGACA | TGGAAACTTG | GGTCTTGAAA | AACATTTTAA | GGTTATTTTT | 300 |
| TCTTTTCTCT | CTCTCTCGCT | CTGTCTTTCT | CTCTCTTTCG | TCAGGGTCTC | CCTCTGTTGC | 360 |
| CCAGGCTGGA | GTCAGTGGCA | CTCATAGCTC | ACTGCAGCCT | TGATCTCCTG | GGCTCAAGAG | 420 |
| TTCTTCCCAC | CTCAGTCTCC | TAAGTAGCTT | GGACTACGG | | | 459 |

( 2 ) INFORMATION FOR SEQ ID NO:20:

( i ) SEQUENCE CHARACTERISTICS:
        ( A ) LENGTH: 329 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:20:

| Met | Trp | Gly | Leu | Lys | Val | Leu | Leu | Pro | Val | Val | Ser | Phe | Ala | Leu |
|---|---|---|---|---|---|---|---|---|---|---|---|---|---|---|
| 1 | | | | 5 | | | | 10 | | | | | 15 | |

| Tyr | Pro | Glu | Glu | Ile | Leu | Asp | Thr | His | Trp | Glu | Leu | Trp | Lys | Lys | Thr |
|---|---|---|---|---|---|---|---|---|---|---|---|---|---|---|---|
| | | | 20 | | | | | 25 | | | | | 30 | | |

| His | Arg | Lys | Gln | Tyr | Asn | Asn | Lys | Val | Asp | Glu | Ile | Ser | Arg | Arg | Leu |
|---|---|---|---|---|---|---|---|---|---|---|---|---|---|---|---|
| | | 35 | | | | | 40 | | | | | 45 | | | |

| Ile | Trp | Glu | Lys | Asn | Leu | Lys | Tyr | Ile | Ser | Ile | His | Asn | Leu | Glu | Ala |
|---|---|---|---|---|---|---|---|---|---|---|---|---|---|---|---|
| | 50 | | | | | 55 | | | | | 60 | | | | |

| Ser | Leu | Gly | Val | His | Thr | Tyr | Glu | Leu | Ala | Met | Asn | His | Leu | Gly | Asp |
|---|---|---|---|---|---|---|---|---|---|---|---|---|---|---|---|
| 65 | | | | | 70 | | | | | 75 | | | | | 80 |

| Met | Thr | Ser | Glu | Glu | Val | Val | Gln | Lys | Met | Thr | Gly | Leu | Lys | Val | Pro |
|---|---|---|---|---|---|---|---|---|---|---|---|---|---|---|---|
| | | | | 85 | | | | | 90 | | | | | 95 | |

| Leu | Ser | His | Ser | Arg | Ser | Asn | Asp | Thr | Leu | Tyr | Ile | Pro | Glu | Trp | Glu |
|---|---|---|---|---|---|---|---|---|---|---|---|---|---|---|---|
| | | | 100 | | | | | 105 | | | | | 110 | | |

| Gly | Arg | Ala | Pro | Asp | Ser | Val | Asp | Tyr | Arg | Lys | Lys | Gly | Tyr | Val | Thr |
|---|---|---|---|---|---|---|---|---|---|---|---|---|---|---|---|
| | | | 115 | | | | | 120 | | | | | 125 | | |

| Pro | Val | Lys | Asn | Gln | Gly | Gln | Cys | Gly | Ser | Cys | Trp | Ala | Phe | Ser | Ser |
|---|---|---|---|---|---|---|---|---|---|---|---|---|---|---|---|
| | 130 | | | | | 135 | | | | | 140 | | | | |

| Val | Gly | Ala | Leu | Glu | Gly | Gln | Leu | Lys | Lys | Lys | Thr | Gly | Lys | Leu | Leu |
|---|---|---|---|---|---|---|---|---|---|---|---|---|---|---|---|
| 145 | | | | | 150 | | | | | 155 | | | | | 160 |

| Asn | Leu | Ser | Pro | Gln | Asn | Leu | Val | Asp | Cys | Val | Ser | Glu | Asn | Asp | Gly |
|---|---|---|---|---|---|---|---|---|---|---|---|---|---|---|---|
| | | | | 165 | | | | | 170 | | | | | 175 | |

| Cys | Gly | Gly | Gly | Tyr | Met | Thr | Asn | Ala | Phe | Gln | Tyr | Val | Gln | Lys | Asn |
|---|---|---|---|---|---|---|---|---|---|---|---|---|---|---|---|
| | | | 180 | | | | | 185 | | | | | 190 | | |

| Arg | Gly | Ile | Asp | Ser | Glu | Asp | Ala | Tyr | Pro | Tyr | Val | Gly | Gln | Glu | Glu |
|---|---|---|---|---|---|---|---|---|---|---|---|---|---|---|---|
| | | | 195 | | | | | 200 | | | | | 205 | | |

| Ser | Cys | Met | Tyr | Asn | Pro | Thr | Gly | Lys | Ala | Ala | Lys | Cys | Arg | Gly | Tyr |
|---|---|---|---|---|---|---|---|---|---|---|---|---|---|---|---|
| | 210 | | | | | 215 | | | | | 220 | | | | |

| Arg | Glu | Ile | Pro | Glu | Gly | Asn | Glu | Lys | Ala | Leu | Lys | Arg | Ala | Val | Ala |
|---|---|---|---|---|---|---|---|---|---|---|---|---|---|---|---|
| 225 | | | | | 230 | | | | | 235 | | | | | 240 |

| Arg | Val | Gly | Pro | Val | Ser | Val | Ala | Ile | Asp | Ala | Ser | Leu | Thr | Ser | Phe |
|---|---|---|---|---|---|---|---|---|---|---|---|---|---|---|---|
| | | | | 245 | | | | | 250 | | | | | 255 | |

| Gln | Phe | Tyr | Ser | Lys | Gly | Val | Tyr | Tyr | Asp | Glu | Ser | Cys | Asn | Ser | Asp |
|---|---|---|---|---|---|---|---|---|---|---|---|---|---|---|---|
| | | | 260 | | | | | 265 | | | | | 270 | | |

| Asn | Leu | Asn | His | Ala | Val | Leu | Ala | Val | Gly | Tyr | Gly | Ile | Gln | Lys | Gly |
|---|---|---|---|---|---|---|---|---|---|---|---|---|---|---|---|
| | | 275 | | | | | 280 | | | | | 285 | | | |

| Asn | Lys | His | Trp | Ile | Ile | Lys | Asn | Ser | Trp | Gly | Glu | Asn | Trp | Gly | Asn |
|---|---|---|---|---|---|---|---|---|---|---|---|---|---|---|---|
| | 290 | | | | | 295 | | | | | 300 | | | | |

| Lys | Gly | Tyr | Ile | Leu | Met | Ala | Arg | Asn | Lys | Asn | Asn | Ala | Cys | Gly | Ile |
|---|---|---|---|---|---|---|---|---|---|---|---|---|---|---|---|
| 305 | | | | | 310 | | | | | 315 | | | | | 320 |

| Ala | Asn | Leu | Ala | Ser | Phe | Pro | Lys | Met |
|---|---|---|---|---|---|---|---|---|
| | | | | 325 | | | | |

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO (v) FRAGMENT TYPE:

(vi) ORIGINAL SOURCE:

(xi) SEQUENCE DESCRIPTION: SEQ ID NO:21:

CCGAAACGAA GCCAGACAAC 20

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:22:

GCTCACCACA GGTAGCAGCA G 21

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:23:

CTGCTGCTAC CTGTGGTGAG C 21

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:24:

CCCAAATTAA ACGCCGAGAG 20

(2) INFORMATION FOR SEQ ID NO:25:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:25:

CTCTCGGCGT TTAATTTGGG 20

( 2 ) INFORMATION FOR SEQ ID NO:26:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:26:

GGTACTTTGA GTCCAGTCAT C 21

( 2 ) INFORMATION FOR SEQ ID NO:27:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:27:

CCAGACTCTG TCGACTATCG 20

( 2 ) INFORMATION FOR SEQ ID NO:28:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:28:

CACATATGGG TAGGCATCTT C 21

( 2 ) INFORMATION FOR SEQ ID NO:29:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:29:

GAAGATGCCT ACCCATATGT G 21

( 2 ) INFORMATION FOR SEQ ID NO:30:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:30:

GTTACATTAT CGCTATTGCA C 21

( 2 ) INFORMATION FOR SEQ ID NO:31:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:31:

GCAAAGGTGT GTATTATGAT G 21

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:32:

GCCGTTGTTC TTATTTCGAG C       21

What is claimed is:

1. An isolated polynucleotide comprising a polynucleotide which is at least 80% identical to the sequence in SEQ ID NO: 1, in which identity is calculated using FASTA and parameters are set so to provide largest match between the two sequences tested.

2. An isolated polynucleotide of claim 1 comprising a polynucleotide which is at least 90% identical to the sequence in SEQ ID NO: 1, in which identity is calculated using FASTA and parameters are set so to provide largest match between the two sequences tested.

3. An isolated polynucleotide of claim 1 comprising a polynucleotide which is at least 95% identical to the sequence in SEQ ID NO: 1, in which identity is calculated using FASTA and parameters are set so to provide largest match between the two sequences tested.

4. An isolated polynucleotide of claim 1 comprising a polynucleotide which is at least 97% identical to the sequence in SEQ ID NO: 1, in which identity is calculated using FASTA and parameters are set so to provide largest match between the two sequences tested.

5. An expression vector comprising cis-acting control elements effective for expression in a host cell of an operatively linked polynucleotide according to claim 1, said expression vector further comprises a polynucleotide of claim 1.

6. An expression vector according to claim 5, wherein said control elements are effective for inducible expression of said polynucleotide in said host cell.

7. A process for producing cells capable of producing a polypeptide comprising transfecting or transforming a host cell with the expression vector of claim 5.

8. A host cell transformed or transfected with the vector of claim 5.

9. A process for producing a polypeptide comprising culturing the host cell of claim 1 under conditions sufficient for the production of said polypeptide and recovering the polypeptide from the culture.

10. An expression vector comprising a polynucleotide of claim 1 capable of producing a polypeptide when said expression vector is present in a compatible host cell.

11. A process for producing a recombinant host cell comprising transforming or transfecting a cell with the expression vector of claim 10 such the host cell, under appropriate culture conditions, produces a polypeptide.

12. A recombinant host cell produced by the process of claim 11.

13. A process for producing a polypeptide comprising culturing a host cell of claim 12 under conditions sufficient for the production of said polypeptide and recovering the polypeptide from the culture.

14. An isolated polynucleotide comprising a polynucleotide which is at least 80% identical to the human gDNA in ATCC Deposit No.: 98035, in which identity is calculated using FASTA and parameters are set so to provide largest match between the two sequences tested.

15. An isolated polynucleotide of claim 14 comprising a polynucleotide which is at least 90% identical to the human gDNA in ATCC Deposit No.:98035, in which identity is calculated using FASTA and parameters are set so to provide largest match between the two sequences tested.

16. An isolated polynucleotide of claim 14 comprising a polynucleotide which is at least 95% identical to the human gDNA in ATCC Deposit No.:98035, in which identity is calculated using FASTA and parameters are set so to provide largest match between the two sequences tested.

17. An isolated polynucleotide of claim 14 comprising a polynucleotide which is at least 97% identical to the human gDNA in ATCC Deposit No.:98035, in which identity is calculated using FASTA and parameters are set so to provide largest match between the two sequences tested.

18. An isolated polynucleotide comprising the polynucleotide which is contained in the human gDNA contained in ATCC Deposit No.: 98035.

19. An isolated polynucleotide comprising the polynucleotide of SEQ ID NO: 1.

20. An isolated polynucleotide selected from the group consisting of:
    (a) the polynucleotide of SEQ ID NO: 3;
    (b) the polynucleotide of SEQ ID NO: 5;
    (c) the polynucleotide of SEQ ID NO: 7;
    (d) the polynucleotide of SEQ ID NO: 9;
    (e) the polynucleotide of SEQ ID NO: 11;
    (f) the polynucleotide of SEQ ID NO: 13;
    (g) the polynucleotide of SEQ ID NO: 15; and
    (h) the polynucleotide of SEQ ID NO: 17.

21. An isolated polynucleotide comprising a polynucleotide selected from the group consisting of:
    (a) a polynucleotide of SEQ ID NO: 2;
    (b) a polynucleotide of SEQ ID NO: 4;
    (c) a polynucleotide of SEQ ID NO: 6;

(d) a polynucleotide of SEQ ID NO: 8;
(e) a polynucleotide of SEQ ID NO: 10;
(f) a polynucleotide of SEQ ID NO: 12;
(g) a polynucleotide of SEQ ID NO: 14;
(h) a polynucleotide of SEQ ID NO: 16;
(i) a polynucleotide of SEQ ID NO: 18; and
(j) a polynucleotide of SEQ ID NO: 19.

22. A polynucleotide which is complementary to any of the polynucleotide of claims 1, 20, 14, 18, and 2–21.

* * * * *